US006500851B2

(12) United States Patent
Beight et al.

(10) Patent No.: US 6,500,851 B2
(45) Date of Patent: Dec. 31, 2002

(54) ANTITHROMBOTIC AGENTS

(75) Inventors: Douglas Wade Beight, Indianapolis, IN (US); Trelia Joyce Craft, Indianapolis, IN (US); Jeffry Bernard Franciskovich, Indianapolis, IN (US); Theodore Goodson, Jr., Indianapolis, IN (US); Steven Edward Hall, Chapel Hill, NC (US); David Kent Herron, Indianapolis, IN (US); Valentine Joseph Klimkowski, Carmel, IN (US); Jeffrey Alan Kyle, Fishers, IN (US); John Joseph Masters, Fishers, IN (US); David Mendel, Indianapolis, IN (US); Guy Milot, Chapel Hill, NC (US); Jason Scott Sawyer, Indianapolis, IN (US); Robert Theodore Shuman, Sedona, AZ (US); Gerald Floyd Smith, Indianapolis, IN (US); Anne Louise Tebbe, Indianapolis, IN (US); Jennifer Marie Tinsley, Martinsville, IN (US); Leonard Crayton Weir, Raleigh, NC (US); James Howard Wikel, Greenwood, IN (US); Michael Robert Wiley, Indianapolis, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 4 days.

(21) Appl. No.: 10/082,453

(22) Filed: Feb. 22, 2002

(65) Prior Publication Data

US 2002/0173518 A1 Nov. 21, 2002

Related U.S. Application Data

(62) Division of application No. 09/445,969, filed as application No. PCT/US98/13416 on Jun. 26, 1998, now Pat. No. 6,372,759.
(60) Provisional application No. 60/050,888, filed on Jun. 26, 1997.

(51) Int. Cl.[7] .................. A61K 31/416; A61K 31/4545; A61K 31/404; C07D 231/56; C07D 409/12; A61P 7/02
(52) U.S. Cl. .................. 514/406; 514/318; 514/338; 514/339; 514/359; 514/394; 514/405; 514/419; 546/193; 546/194; 546/198; 546/199; 548/304.4; 548/362.5; 548/469; 548/494; 548/261
(58) Field of Search .................. 548/362.5, 304.4, 548/469, 494, 261; 546/194, 198, 193, 199; 514/406, 318, 359, 394, 405, 419

(56) References Cited

U.S. PATENT DOCUMENTS 4,256,901 A    3/1981  Gangneux

| 4,978,787 A | 12/1990 | Haga et al. |
| 5,492,895 A | 2/1996 | Vlasuk |
| 5,569,768 A | 10/1996 | Boyd et al. |
| 5,576,343 A | 11/1996 | Nagahara et al. |
| 5,721,214 A | 2/1998 | Marlow |
| 6,140,351 A * | 10/2000 | Arnaiz ........................ 514/336 |
| 6,313,151 B1 | 11/2001 | Beight et al. |
| 6,314,122 B1 | 11/2001 | Beight et al. |
| 6,372,759 B1 | 4/2002 | Beight et al. |
| 6,380,221 B1 * | 4/2002 | Arnaiz ........................ 514/337 |
| 2002/0049234 A1 | 4/2002 | Beight et al. |

FOREIGN PATENT DOCUMENTS

| WO | WO 98/57951 | 12/1998 |
| WO | WO 99/00121 | 1/1999 |
| WO | WO 99/00126 | 1/1999 |
| WO | WO 99/00127 | 1/1999 |
| WO | WO 99/32477 | 7/1999 |
| WO | WO 99/48878 | 9/1999 |
| WO | WO 00/39092 | 7/2000 |
| WO | WO 00/39111 | 7/2000 |
| WO | WO 00/39117 | 7/2000 |
| WO | WO 00/39118 | 7/2000 |
| WO | WO 2002/28535 | * 4/2002 |

OTHER PUBLICATIONS

U.S. patent application Ser. No. 08/994,284, publication date Dec. 1997, Priority for WO99/32477.
U.S. patent application Ser. No. 09/187,459, publication date Nov. 1998, Priority for WO99/32477.
U.S. patent application Ser. No. 09/961,164, publication date Sep. 2001, Divisional of AJ.
U.S. patent application Ser. No. 10/082,429, publication date Feb. 2002, Divisional of AL.
U.S. patent application Ser. No. 09/967,054, publication Sep. 2001, Divisional of AN.
U.S. patent application Ser. No. 09/445,970, publication May 2000, 371 of BD.
Wallis, R.B. Inhibitors of Coagulation Factor Xa: From Macromolecular Beginnings to Small Molecules. Current Opinion in Therapeutic Patents. 1993, vol. 3, No. 8, pp. 1173–1179.
Edmunds, Jeremy J. and Rapundalo, Stephen T., (Doherty, Annette M. Section Editor). *Annual Reports in Medicinal Chemistry*, (1996), 31, 51–60.
Myers, H. V., et al., *Molecular Diversity*, (1995), 1, 13–20.
Kaiser B and Hauptmann J. Cardiovacular Drug Reviews. 12 (3), 1994, pp. 225–236.
Current Pharmaceutical Design, 1996, 2., "Factor Xa Inhibitors," Kunitada, Satoshi, et al., pp. 531–542.

* cited by examiner

Primary Examiner—Evelyn Mei Huang
(74) Attorney, Agent, or Firm—Thomas E. Jackson

(57) ABSTRACT

This application relates to a compound of formula I (or a prodrug thereof or a pharmaceutically acceptable salt of the compound or prodrug thereof) as defined herein, pharmaceutical compositions thereof, and its use as an inhibitor of factor Xa, as well as a process for its preparation and intermediates therefor.

23 Claims, No Drawings

ANTITHROMBOTIC AGENTS

This application is a divisional of application Ser. No. 09/445,969, filed Mar. 20, 2000 now U.S. Pat. No. 6,372,759 (PCT/US98/13416, international filing date Jun. 26, 1998), the entire disclosure of which herein is incorporated by reference, and claims the benefit of U.S. Provisional Application No. 60/050,888, filed Jun. 26, 1997.

This invention relates to antithrombotic bicyclic heterocycles which demonstrate activity as inhibitors of factor Xa and, accordingly, which are useful anticoagulants in mammals. In particular it relates to bicyclic heterocycles having high anticoagulant activity, and antithrombotic activity. Thus, this invention relates to new inhibitors of factor Xa, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Jeremy J. Edmunds and Stephen T. Rapundalo (Annette M. Doherty, Section Editor), *Annual Reports in Medicinal Chemistry*, (1996), 31, 51–60.

Although the heparins and coumarins are effective anticoagulants, no commercial drug has yet emerged from the small synthetic molecules; and despite the continuing promise for this class of compounds, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent inhibitors of factor Xa which may have high bioavailability following oral administration.

According to the invention there is provided a method of inhibiting factor Xa comprising using an effective amount of a factor Xa inhibiting compound of formula I

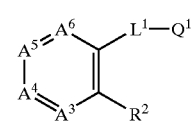

wherein $A^3, A^4, A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein $R^3$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

one of $R^4$ and $R^5$ is hydrogen, methyl, halo, trifluoromethyl, nitro, amino(imino)methyl, amino(hydroxyimino)methyl, $R^fO$—, $R^fO_2C$—, $R^fO_2C$—$CH_2$—, $R^fO_2C$—$CH_2$—O—, 3-methoxycarbonyl-1-oxopropyl, $R^gNH$— or bis(methylsulfonyl)amino;

the other of $R^4$ and $R^5$ is hydrogen, halo or methyl; and $R^6$ is hydrogen, fluoro, hydroxy, [(1–2C)alkyl]carbonyloxy (which may bear an ω-carboxy substituent), benzoyloxy (which may bear one or more halo, hydroxy, methoxy or methyl substituents), methyl or methoxy;

in which $R^f$ is hydrogen, (1–4C)alkyl or benzyl; $R^g$ is hydrogen, acetyl, trifluoroacetyl, phenylalanyl, 2-(t-butoxycarbonylamino)-4-methylsulfinyl-1-oxobutyl or $R^hSO_h$— (wherein h is 1 or 2); and $R^h$ is (1–4C)alkyl, trifluoromethyl, phenyl, 3,5-dimethylisoxazol-4-yl or dimethylamino; or two adjacent residues selected from $R^3$, $R^4$, $R^5$ and $R^6$ together form a benz ring; and the other two are each hydrogen; or $A^3, A^4, A^5$ and $A^6$, together with the two carbons to which they are attached, complete a substituted heteroaromatic ring in which (a) one of $A^3, A^4, A^5$ and $A^6$ is N, and each of the others is $CR^3$, $CR^4$, $CR^5$ or $CR^6$, respectively;

(b) two adjacent residues of $A^3, A^4, A^5$ and $A^6$ together form S, and each of the others is $CR^3$, $CR^4$, $CR^5$ or $CR^6$, respectively;

(c) two non-adjacent residues of $A^3, A^4, A^5$ and $A^6$ are each N, and each of the others is $CR^3$, $CR^4$, $CR^5$ or $CR^6$, respectively; or (d) $A^3$ and $A^4$ together form a fused benz ring, and $A^5$ and $A^6$ together form —NH—;

wherein each of $R^3$, $R^4$, $R^5$ and $R^6$ is hydrogen, or one or two of $R^3$, $R^4$, $R^5$ and $R^6$ is independently chloro, bromo or methyl and the others are hydrogen;

$L^1$ is —NH—CO— or —CO—NH— such that —$L^1$—$Q^1$ is —NH—CO—$Q^1$ or —CO—NH—$Q^1$;

$Q^1$ is

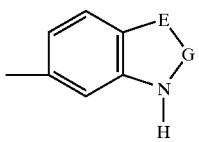

wherein
—E—G—NH— is —CH$_2$—CH$_2$—NH—, —C(R$^a$)=CH—NH—, —C(R$^a$)=N—NH—, —N=CH—NH— or —N=N—NH— in which R$^a$ is hydrogen, fluoro, chloro, bromo or methyl;

$R^2$ is —L$^{2A}$—Q$^{2A}$, —L$^{2B}$—Q$^{2B}$, —L$^{2C}$—Q$^{2C}$ or —L$^{2D}$—Q$^{2D}$ wherein $L^{2A}$ is a direct bond; and
$Q^{2A}$ is

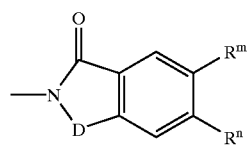

in which
D is carbonyl or —CHR$^k$— in which R$^k$ is hydrogen, hydroxy, (1–6C)alkoxy or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

$L^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$O—Q$^{2B}$ or —O—CH$_2$—Q$^{2B}$; and $Q^{2B}$ is

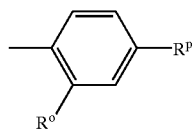

in which
R$^o$ is hydrogen, halo, (1–6C)alkyl, (1–4C)alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxo, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl;

$L^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —L$^{2C}$—Q$^{2C}$ is —NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—, —NR$^w$—CH$_2$—, —O—, —O—CH$_2$— or —S—CH$_2$—; Y is —NR$^w$—CH$_2$— or —O—CH$_2$—; each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and $Q^{2C}$ is 1-(4-pyridyl)piperidin-4-yl, 1-(4-pyridyl)-piperidin-3-yl or 1-(4-pyridyl)pyrrolidin-3-yl in which the pyridyl may bear a substituent at its 2-position selected from cyano, aminomethyl, carboxy, hydroxymethyl and (1–2C)alkyl;

$L^{2D}$ is —NH—CO— such that —L$^{2D}$—Q$^{2D}$ is —NH—CO—Q$^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl or 3,4-didehydropiperidin-4-yl (either one bearing a substituent at the 1-position selected from methylsulfonyl, phenylsulfonyl, (1–5C) alkyl, (4–7C)cycloalkyl, tetrahydropyran-4-yl, 4-thiacyclohexyl and —CH$_2$—R$^z$ in which R$^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent);

or a prodrug of the compound of formula I;
or a pharmaceutically acceptable salt of the compound of formula I or prodrug thereof.

A particular factor X$^a$ inhibiting compound of formula I is one wherein $A^3, A^4, A^5$ and $A^6$, together with the two carbons to which they are attached, complete a substituted benzene in which A$^3$ is CR$^3$, A$^4$ is CR$^4$, A$^5$ is CR$^5$, and A$^6$ is CR$^6$; wherein $R^3$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

one of R$^4$ and R$^5$ is hydrogen, methyl, halo, trifluoromethyl, nitro, amino(imino)methyl, amino (hydroxyimino)methyl, R$^f$O—, R$^f$O$_2$C—, R$^f$O$_2$C—CH$_2$—, R$^f$O$_2$C—CH$_2$—O—, 3-methoxycarbonyl-1-oxopropyl, R$^g$NH— or bis(methylsulfonyl)amino;

the other of R$^4$ and R$^5$ is hydrogen, halo or methyl; and

R$^6$ is hydrogen, hydroxy, [(1–2C)alkyl]carbonyloxy (which may bear an ω-carboxy substituent), benzoyloxy (which may bear one or more halo, hydroxy, methoxy or methyl substituents), methyl or methoxy;

in which R$^f$ is hydrogen, (1–4C)alkyl or benzyl; R$^g$ is hydrogen, acetyl, trifluoroacetyl, phenylalanyl, 2-(t-butoxycarbonylamino)-4-methylsulfinyl-1-oxobutyl or R$^h$SO$_2$—; and R$^h$ is (1–4C)alkyl, trifluoromethyl, phenyl, 3,5-dimethylisoxazol-4-yl or dimethylamino; or two adjacent residues selected from R$^3$, R$^4$, R$^5$ and R$^6$ together form a benz ring; and the other two are each hydrogen; or $A^3, A^4, A^5$ and $A^6$, together with the two carbons to which they are attached, complete a substituted heteroaromatic ring in which (a) one of A$^3$, A$^4$, A$^5$ and A$^6$ is N, and each of the others is CR$^3$, CR$^4$, CR$^5$ or CR$^6$, respectively;

(b) two adjacent residues of A$^3$, A$^4$, A$^5$ and A$^6$ together form S, and each of the others is CR$^3$, CR$^4$, CR$^5$ or CR$^6$, respectively;

(c) two non-adjacent residues of $A^3$, $A^4$, $A^5$ and $A^6$ are each N, and each of the others is $CR^3$, $CR^4$, $CR^5$ or $CR^6$, respectively; or (d) $A^3$ and $A^4$ together form a fused benz ring, and $A^5$ and $A^6$ together form —NH—;

wherein
each of $R^3$, $R^4$, $R^5$ and $R^6$ is hydrogen, or one or two of $R^3$, $R^4$, $R^5$ and $R^6$ is independently chloro, bromo or methyl and the others are hydrogen;

$L^1$ is —NH—CO— or —CO—NH— such that —$L^1$—$Q^1$ is —NH—CO—$Q^1$ or —CO—NH—$Q^1$;

$Q^1$ is

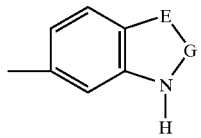

wherein —E—G—NH— is —$CH_2$—$CH_2$—NH—, —C($R^a$)=CH—NH—, —C($R^a$)=N—NH—, —N=CH—NH— or —N=N—NH— in which $R^a$ is hydrogen, fluoro, chloro, bromo or methyl;

$R^2$ is —$L^{2A}$—$Q^{2A}$, —$L^{2B}$—$Q^{2B}$, —$L^{2C}$—$Q^{2C}$ or —$L^{2D}$—$Q^{2D}$ wherein $L^{2A}$ is a direct bond; and
$Q^{2A}$ is

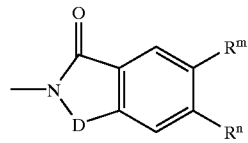

in which
D is carbonyl or —$CHR^k$— in which $R^k$ is hydrogen, hydroxy, (1–6C)alkoxy or —$CH_2$—$R^j$ in which $R^j$ is carboxy, [(1–4C)alkoxy]carbonyl or carbamoyl which may bear one or two (1–2C)alkyl substituents on the nitrogen; and one of $R^m$ and $R^n$ is hydrogen and the other is amino, bromo, (1–4C)alkyl or (1–4C)alkoxy, or $R^m$ and $R^n$ together form a benz ring;

$L^{2B}$ is —NH—CO—, —O—CO—, —$CH_2$—O— or —O—$CH_2$— such that —$L_{2B}$—$Q^{2B}$ is —NH—CO—$Q^{2B}$, —O—CO—$Q^{2B}$, —$CH_2$—O—$Q^{2B}$ or —O—$CH_2$—$Q^{2B}$; and $Q^{2B}$ is

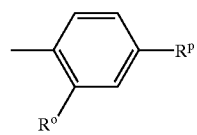

in which
$R^o$ is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —S(O)$_q$— (wherein q is 0, 1 or 2), or —$NR^r$— (wherein $R^r$ is hydrogen or methyl); and $R^q$ is (1–6C)alkyl, phenyl, 3-pyridyl or 4-pyridyl;

$L^{2C}$ is —$NR^v$—CO—X—, —$NR^v$—CS—Y—, —$CH_2$—CO—$NR^w$—$CH_2$—, —O—CO—, —O—$CH_2$—, —S—$CH_2$— or —$CH_2$—$NR^x$—$CH_2$— such that —$L^{2C}$—$Q^{2C}$ is —$NR^v$—CO—X—$Q^{2C}$, —$NR^v$—CS—Y—$Q^{2C}$, —$CH_2$—CO—$NR^w$—$CH_2$—$Q^{2C}$, —O—CO—$Q^{2C}$, —O—$CH_2$—$Q^{2C}$, —S—$CH_2$—$Q^{2C}$ or —$CH_2$—$NR^x$—$CH_2$—$Q^{2C}$ in which X is —$(CH_2)_x$— (wherein x is 0, 1 or 2), —$NR^w$—$CH_2$—, —O—$CH_2$— or —S—$CH_2$—; Y is —$NR^w$—$CH_2$— or —O—$CH_2$—; each of $R^v$ and $R^w$ is independently hydrogen, benzyl or (1–6C)alkyl which is not branched at the α-position; and $R^x$ is hydrogen, benzyloxycarbonyl or [(1–4C)alkoxy]carbonyl; and $Q^{2C}$ is 1-(4-pyridyl)piperidin-4-yl in which the pyridyl may bear a substituent at its 2-position selected from cyano, aminomethyl, carboxy, hydroxymethyl and (1–2C)alkyl;

$L^{2D}$ is —NH—CO— such that —$L^{2D}$—$Q^{2D}$ is —NH—CO—$Q^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —$CH_2$—$R^z$ in which $R^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent;

or a prodrug of the compound of formula I;
or a pharmaceutically acceptable salt of the compound of formula I or prodrug thereof.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In general, the factor Xa inhibiting compounds of formula I are believed to be novel and, thus, to constitute an additional aspect of the invention. Thus, according to the invention there is provided a novel compound of formula I (or a pharmaceutically acceptable salt thereof) according to any of the definitions herein of a compound of formula I, provided that the compound is not one which is not novel.

A pharmaceutically acceptable salt of an antithrombotic agent of the instant invention includes one which is an acid-addition salt made from a basic compound of formula I and an acid which provides a pharmaceutically acceptable anion, as well as a salt which is made from an acidic compound of formula I and a base which provides a pharmaceutically acceptable cation. Thus, a salt of a novel compound of formula I as provided herein made with an acid or base which affords a pharmaceutically acceptable counterion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted. When two adjacent residues form a (fused) benz ring, they form a cis,cis-buta-1,3-dien-1,4-diyl divalent radical.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–2C)alkyl is methyl or ethyl, and more particularly is methyl; for (1–4C)alkyl is methyl, ethyl, propyl, isopropyl, butyl, isobutyl, or t-butyl, and more particularly is methyl, isopropyl, butyl or t-butyl; for (1–6C)alkyl is methyl, ethyl, propyl, butyl, pentyl or hexyl, and more particularly is methyl, butyl, or hexyl. A particular value for halo is bromo or chloro, and more particularly is chloro.

A particular compound of formula I is one of formula Ia

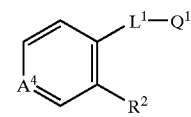

wherein $A^4$, $L^1$, $Q^1$ and $R^2$ have any of the values defined herein.

A particular value for $Q^1$ is 6-indolyl or 6-indazolyl.

A particular value for $R^2$ is, for example, (4-t-butylbenzoyl)amino, (4-methoxybenzoyl)amino, or [1-(4-pyridyl)-piperidin-4-yl]methoxycarbonylamino.

One particular compound of formula I as described herein is one in which L1—$Q^1$ is —NH—CO—$Q^1$.

Another particular compound of formula I as described herein is one in which L1—$Q^1$ is —CO—NH—$Q^1$.

A prodrug of a compound of formula I may be one formed in a conventional manner with a functional group of the compound, such as with an amino, hydroxy or carboxy group.

A compound of formula I may be prepared by processes which include processes known in the chemical art for the production of any known compounds of formula I or of structurally analogous compounds or by a novel process described herein. A process for the preparation of a novel compound of formula I (or a pharmaceutically acceptable salt thereof), novel processes for the preparation of a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a novel compound of formula I (or a pharmaceutically acceptable salt thereof) as provided in any of the above descriptions which is selected from any of those described in the examples, including the following.

(A) For a compound of formula I in which the linkage of $R^2$ to the ring terminates in —NH—CO—, —$NR^v$—CO— or —$NR^v$—CS—, acylating an amine of formula II,

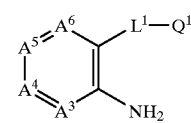

or a corresponding amine in which the nitrogen bears the group $R^v$, using a corresponding acid which terminates with the group HO—CO— or HO—CS—, or an activated derivative thereof. Typical activated derivatives include the acid halides, activated esters, including 4-nitrophenyl esters and those derived from coupling reagents, as well as (when the product is a urea or thiourea) isocyanates and isothiocyanates. It may be preferred to deprotonate the amine using a strong base in anhydrous conditions for the acylation reaction.

(B) For a compound of formula I in which —$L^1$—$Q^1$ is —NH—CO—$Q^1$, acylating an amine of formula III

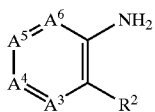

using an acid of formula HO—CO—$Q^1$, or an activated derivative thereof.

(C) For a compound of formula I in which —$L^1$—$Q^1$ is —CO—NH—$Q^1$ and $R^2$ is of the form —NH—CO—$Q^2_1$, acylating an amine of formula $H_2N$—$Q^1$ using a [1,3] oxazine of formula IV,

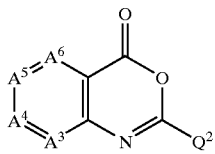

wherein $Q^2$ represents, for example, $Q^{2B}$, $Q^{2C}$ or $Q^{2D}$.

(D) For a compound of formula I in which $R^2$ is —$L^{2A}$—$Q^{2A}$ and D is carbonyl, diacylating a compound of formula II using an anhydride of formula V.

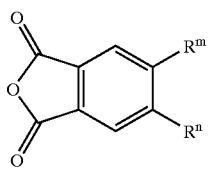

(E) For a compound of formula I in which $R^2$ is —O—CO—$Q^{2B}$, acylating an alcohol of formula VI

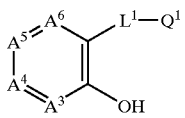

using an acid of formula HO—CO—$Q^{2B}$, or an activated derivative thereof.

(F) For a compound of formula I is which —E—G—NH— is —$CH_2$—$CH_2$—NH—, reducing the double bond of a corresponding compound of formula I in which —E—G—NH— is —CH=CH—NH—.

(G) For a compound of formula I in which $R^4$ or $R^5$ is amino, reducing the nitro group of a corresponding compound of formula I in which $R^4$ or $R^5$ is nitro.

(H) For a compound of formula I in which $R^4$ or $R^5$ is methylsulfonylamino, substituting the amino group of a corresponding compound of formula I in which $R^4$ or $R^5$ is amino using an activated derivative of methanesulfonic acid.

(I) For a compound of formula I in which $R^4$ or $R^5$ is bis(methylsulfonyl)amino, substituting the methylsulfonylamino group of a corresponding compound of formula I in which $R^4$ or $R^5$ is methylsulfonylamino.

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

A novel intermediate or starting material compound such as, for example, a novel compound of formula II, III, IV or VI, etc., provides a further aspect of the invention.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which $R^4$ is hydroxy, but in which the corresponding substituent is —$OP^p$ in place of hydroxy, wherein $P^p$ is a phenol protecting group other than (1–4C)alkyl or benzyl. Phenol protecting groups are well known in the art, for example as described in T. W. Greene and P. G. M. Wuts, "Protecting Groups in Organic Synthesis" (1991). Further, $P^p$ may denote a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluene sulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of formula I which bears an acidic moiety, such as a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II, III, IV or VI discussed above.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient;* Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

$$\text{Enzyme} + I \rightleftharpoons \text{Enzyme} - I$$

$$\text{Kass} = \frac{[\text{Enzyme} - I]}{[(\text{Enzyme}) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 $\mu$L buffer (0.03 M Tris, 0.15 M NaCl pH 7) in each well, followed by 25 $\mu$L of inhibitor solution (in 100% methanol, or in 50% v:v aqueous methanol) and 25 $\mu$L enzyme solution; within two minutes, 150 $\mu$L aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA; 5.9 nM human thrombin or 1.4 nM bovine trypsin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.81 mM HD-Ile-Pro-Arg-pNA; and 0.37 nM urokinase is used with 0.30 mM pyro-gfsGlu-Gly-Arg-pNA.

Kass is calculated for a range of concentrations of test compounds and the mean value reported in units of liter per mole. In general, a factor Xa inhibiting compound of formula I of the instant invention exhibits a Kass of 0.1 to $0.5 \times 10^6$ L/mole or much greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.,* 185, 1–11 (1980; and Smith, et al., *Biochemistry,* 11, 2958–2967, (1972). Human fibrinogen (98 percent pure/ plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 $\mu$L thrombin (73 NIH unit/mL) to 100 $\mu$L human plasma which contains 0.0229 $\mu$Ci 125-iodine labeled fibrinogen. Clot lysis is studied by overlaying the clots with 50 $\mu$L of urokinase or streptokinase (50, 100, or 1000 unit/mL) and incubating for 20 hours at room temperature. After incubation the tubes are centrifuged in a Beckman Microfuge. 25 $\mu$L of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 $\mu$g/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varion) cartridges for sample preparation and a methanol/30 nM ammonium acetate buffer (pH 4) gradient optimized for each compound. % Oral bioavailability is calculated by the following equation:

$$\% \text{Oral bioavailability} = \frac{AUC\ po}{AUC\ iv} \times \frac{Dose\ iv}{Dose\ po} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100 μA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40 μL sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of p<0.05. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
aq=aqueous
Bn or Bzl=benzyl
Boc=t-butyloxycarbonyl
Bu=butyl
n-BuLi=butyllithium
Calc=calculated
conc=concentrated
DCC=dicyclohexylcarbodiimide
DMAP=4-dimethylaminopyridine
DMF=dimethylformamide
DMSO=dimethylsulfoxide EDC=1-(3-dimethylaminopropyl)-3-ethyl-carbodiimide hydrochloride
eq=(molar) equivalent
Et=ethyl
EtOAc=ethyl acetate
Et₃N=triethylamine
Et₂O=diethyl ether
EtOH=ethanol
FAB=Fast Atom Bombardment (Mass Spectroscopy)
FD-MS=field desorption mass spectrum
FIA-MS=flow injection analysis mass spectrum
Hex=hexanes
HOAt=1-hydroxy-7-azabenzotriazole
HOBT=1-hydroxybenzotriazole
HPLC=High Performance Liquid Chromatography
HRMS=high resolution mass spectrum
i-PrOH=isopropanol
IR=Infrared Spectrum
IS-MS=ion spray mass spectrum
Me=methyl
MeI=methyl iodide
MeOH=methanol
NBS=N-bromosuccinimide
NMR=Nuclear Magnetic Resonance
Ph=phenyl
i-Pr=isopropyl
RPHPLC=Reversed Phase High Performance Liquid Chromatography
satd=saturated
SiO₂=silica gel
TBS=tert-butyldimethylsilyl
TFA=trifluoroacetic acid
THF=tetrahydrofuran
TIPS=triisopropylsilyl
TLC=thin layer chromatography
tosyl=p-toluenesulfonyl
triflic acid=trifluoromethanesulfonic acid Unless otherwise stated, pH adjustments and work up are with aqueous acid or base solutions. ¹H-NMR indicates a satisfactory NMR spectrum was obtained for the compound described. IR indicates a satisfactory infra red spectrum was obtained for the compound described.

For consistency and clarity, a number of compounds are named as substituted diamine derivatives.

The following conditions were used for reverse phase HPLC analysis and purification in some of the compounds described in the examples below.
Solvents: A 0.05% conc. HCl in water, B=acetonitrile
Column: Vydac C18—5×25 cm
Method A: 10 mL/min; 80/20 (A/B) through 50/50 (A/B), linear gradient over 120 min.
Method B: 10 mL/min; 90/10 (A/B) through 40/60 (A/B), linear gradient over 180 min.

EXAMPLE 1

Preparation of 2-[(4-t-Butylbenzoyl)amino]-N-(6-indazolyl)benzamide

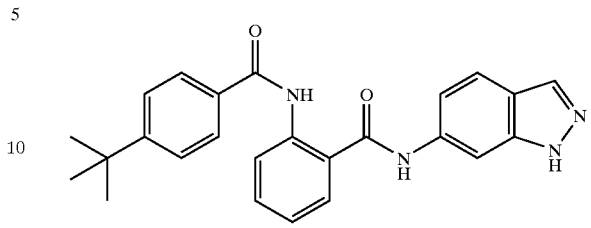

A) 1-Boc-6-nitroindazole

To a stirring solution of 6-nitroindazole (5 g, 31 mmol) in dichloromethane (100 mL) and DMF (10 mL), was added di-t-butyl dicarbonate (13 g, 61 mmol) followed by DMAP (3.7 g, 31 mmol). After stirring 16 h, the solvent was removed by rotary evaporation and the residue was dissolved in ethyl acetate (300 mL) and washed with 1 M citric acid, brine, satd aq NaHCO₃ and again with brine. The organic phase was then dried with MgSO₄, filtered and concentrated in vacuo. The solid was suspended in ether with vigorous stirring and filtered, then washed again with ether and dried in vacuo to give 7.1 g (88%) of white solid.
¹H-NMR
FD-MS, m/e 263 (M⁺)
Analysis for $C_{12}H_{13}N_3O_4$: Calc: C, 54.75; H, 4.98; N, 15.96; Found: C, 54.72; H, 4.96; N, 16.01.

B) 1-Boc-6-aminoindazole

To a stirring solution of 1-Boc-6-nitroindazole (2.5 g, 9.5 mmol) in ethyl acetate (75 mL) under nitrogen was added 10% Pd/C (500 mg). The mixture was placed under vacuum and the atmosphere was replaced with hydrogen (1 atm). After stirring for 12 h, the hydrogen balloon was removed and diatomaceous earth was added. The mixture was then filtered over a pad of diatomaceous earth and the solvent was removed by rotary evaporation to give 2.17 g (98%) of light pink solid.
¹H-NMR
FD-MS, m/e 233 (M⁺)
Analysis for $C_{12}H_{15}N_3O_2$: Calc: C, 61.79; H, 6.48; N, 18.01; Found: C, 61.49; H, 6.39; N, 17.94.

C) N-(1-Boc-6-indazolyl)-2-nitrobenzamide

To a stirring solution of 1-Boc-6-aminoindazole (1.5 g, 6.4 mmol) in dichloromethane (25 mL) was added pyridine (1.55 mL, 19.2 mmol) followed by 2-nitrobenzoyl chloride (1 mL, 7.1 mmol). After stirring for 12 h, the solvent was removed by rotary evaporation and the residue was partitioned between ethyl acetate (250 mL) and water (250 mL). The aqueous phase was separated and the organic phase was washed with 1 M citric acid, brine, satd aq NaHCO₃, and brine. The organic phase was then dried with MgSO₄, filtered and concentrated in vacuo to give 2.64 g of off-white solid.
¹H-NMR
FD-MS, m/e 382 (M⁺)
Analysis for $C_{19}H_{18}N_4O_5 \cdot 0.3H_2O$: Calc: C, 58.85; H, 4.83; N, 14.44; Found: C, 58.82; H, 4.77; N, 14.29.

D) 2-Amino-N-(1-Boc-6-indazolyl)benzamide

Using methods substantially equivalent to those described in Example 1-B, 2-amino-N-(1-Boc-6-indazolyl)benzamide (0.92 g, 100%) was prepared from N-(1-Boc-6-indazolyl)-2-nitrobenzamide.
¹H-NMR
FD-MS, m/e 352 (M⁺)

Analysis for $C_{19}H_{20}N_4O_3 \cdot 0.8H_2O$: Calc: C, 62.22; H, 5.94; N, 15.27; Found: C, 62.35; H, 6.03; N, 14.94.

E) 2-[(4-t-Butylbenzoyl)amino]-N-(1-Boc-indazol-6-yl)benzamide

Using methods substantially equivalent to those described in Example 1-C, using 4-t-butylbenzoyl chloride, 2-[(4-t-butylbenzoyl)amino]-N-(1-Boc-6-indazolyl)benzamide (318 mg, 79%) was prepared from 2-amino-N-(1-Boc-6-indazolyl)benzamide.

$^1$H-NMR

FD-MS, m/e 512 (M$^+$)

Analysis for $C_{30}H_{32}N_4O_4$: Calc: C, 70.29; H, 6.29; N, 10.93; Found: C, 70.55; H, 6.33; N, 11.02.

F) 2-[(4-t-Butylbenzoyl)amino]-N-(6-indazolyl)benzamide

To a stirring solution of 2-[(4-t-butylbenzoyl)amino]-N-(1-Boc-6-indazolyl)benzamide (200 mg, 0.39 mmol) in anisole (1 mL) and dichloromethane (10 mL) was added TFA (10 mL). After stirring for 30 min, the solvents were removed by rotary evaporation and the residue was partitioned between ethyl acetate and satd aq NaHCO$_3$. The aqueous phase was removed and the organic phase was washed again with NaHCO$_3$, followed by brine. The organic phase was then dried with MgSO$_4$, filtered and concentrated in vacuo to a very small volume, then diluted with ether and sonicated. The white precipitate was then filtered and dried in vacuo to give 124 mg (77%) of white solid.

$^1$H-NMR

FD-MS, m/e 412.2 (M$^+$)

Analysis for $C_{25}H_{24}N_4O_2$: Calc: C, 72.80; H, 5.87; N, 13.58; Found: C, 72.88; H, 6.12; N, 13.28.

EXAMPLE 2

Preparation of 2-[(4-t-Butylbenzoyl)amino]-N-(6-indolyl)benzamide

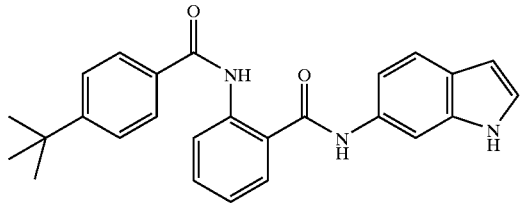

A) 1-Boc-6-nitroindole

By methods substantially equivalent to those described in Example 1-A, 1-Boc-6-nitroindole (3.07 g, 76%) was prepared from 6-nitroindole.

$^1$H-NMR

FD-MS, m/e 262 (M$^+$)

Analysis for $C_{13}H_{14}N_2O_4$: Calc: C, 59.54; H, 5.38; N, 10.68; Found: C, 59.55; H, 5.30; N, 10.74.

B) 1-Boc-6-aminoindole

To a stirring solution of 1-Boc-6-nitroindole (250 mg, 0.95 mmol) in THF (5 mL) and MeOH (10 mL) at 0° C., was added Ni(OAc)$_2 \cdot$4H$_2$O (473 mg, 1.9 mmol). After complete dissolution, NaBH$_4$ (143 mg, 3.8 mmol) was added slowly. Upon addition of the NaBH$_4$, the reaction mixture turned black and vigorous gas evolution was observed. After 15 min, the solvents were removed in vacuo and the residue was dissolved in a stirring mixture of ethyl acetate (100 mL), conc NH$_4$OH (10 mL) and water (20 mL). The layers were separated and the organic phase was washed again with 33% conc NH$_{40}$OH in water and then washed twice with brine. The organic phase was then dried with MgSO$_4$, filtered and concentrated in vacuo.

$^1$H-NMR

FD-MS, m/e 232 (M$^+$)

Analysis for $C_{13}H_{16}N_2O_2$: Calc: C, 67.22; H, 6.94; N, 12.06; Found: C, 67.06; H, 6.87; N, 11.98.

C) N-(1-Boc-6-indolyl)-2-nitrobenzamide

By methods substantially equivalent to those described in Example 1-C, N-(1-Boc-6-indolyl)-2-nitrobenzamide (2.2 g, 95%) was prepared from 1-Boc-6-aminoindole.

$^1$H-NMR

FD-MS, m/e 381 (M$^+$)

Analysis for $C_{20}H_{19}N_3O_5$: Calc: C, 62.99; H, 5.02; N, 11.02; Found: C, 63.57; H, 5.35; N, 10.76.

D) 2-Amino-N-(1-Boc-6-indolyl)benzamide

By methods substantially equivalent to those described in Example 2-B, 2-amino-N-(1-Boc-6-indolyl)benzamide (870 mg, 95%) was prepared from 1-[N-(1-Boc-6-indolyl)]-2-nitrobenzamide.

$^1$H-NMR

FD-MS, m/e 351 (M$^+$)

E) N-(1-Boc-6-indolyl)-2-[(4-t-butylbenzoyl)amino]benzamide

By methods substantially equivalent to those described in Example 1-C, N-(1-Boc-6-indolyl)-2-[(4-t-butylbenzoyl)amino]benzamide (140 mg, 41%) was prepared from 4-t-butyl-benzoyl chloride and 2-amino-N-(1-Boc-6-indolyl)benzamide.

$^1$H-NMR

FD-MS, m/e 511 (M$^+$)

Analysis for $C_{31}H_{33}N_3O_4$: Calc: C, 72.78; H, 6.50; N, 8.21; Found: C, 72.57; H, 6.39; N, 8.11.

F) 2-[(4-t-Butylbenzoyl)amino]-N-(6-indolyl)benzamide

N-(1-Boc-6-indolyl)-2-[(4-t-butylbenzoyl)amino]benzamide (75 mg, 0.147 mmol) was placed in a 10 dram (37 mL) glass scintillation vial and the vial was placed under nitrogen on a hot plate. As the solid melted, gas evolution was observed. After the solid had completely melted (about 5 min), the vial was removed from the hot plate and allowed to cool. The residue was then dissolved in DMF (2 mL), diluted with ethyl acetate (150 mL) and washed twice with water, once with satd aq NaHCO$_3$ and once with brine. The organic phase was dried with MgSO$_4$, filtered and concentrated in vacuo. The crude solid was recrystallized from Et$_2$O to give 30 mg (50%) of white solid.

$^1$H-NMR

FD-MS, m/e 411.2 (M$^+$)

Analysis for $C_{26}H_{25}N_3O_2 \cdot H_2O$: Calc: C, 72.71; H, 6.34; N, 9.78; Found: C, 72.73; H, 6.17; N, 9.39.

EXAMPLE 3

Preparation of N-(6-Indazolyl)-2-[(4-methoxybenzoyl)amino]benzamide

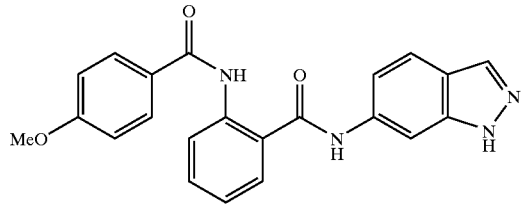

A) N-(1-Boc-6-indazolyl)-2-[(4-methoxybenzoyl)amino]benzamide

By methods substantially equivalent to those described in Example 1-C, N-(1-Boc-6-indazolyl)-2-[(4-methoxybenzoyl)amino]benzamide (280 mg, 39%) was prepared from p-anisoyl chloride and 2-amino-N-(1-Boc-6-indazolyl)benzamide.

$^1$H-NMR

FD-MS, m/e 486.1 (M$^+$)

Analysis for $C_{27}H_{26}N_4O_5$: Calc: C, 66.66; H, 5.39; N, 11.52; Found: C, 66.39; H, 5.54; N, 11.45.

B) N-(6-Indazolyl)-2-[(4-methoxybenzoyl)amino]benzamide

By methods substantially equivalent to those described in Example 1-F, N-(6-indazolyl)-2-[(4-methoxybenzoyl)amino]benzamide (160 mg, 100%) was prepared from N-(1-Boc-6-indazolyl)-2-[(4-methoxybenzoyl)amino]benzamide.

$^1$H-NMR

FD-MS, m/e 386 (M$^+$)

Analysis for $C_{22}H_{18}N_4O_3$: Calc: C, 68.38; H, 4.70; N, 14.50; Found: C, 68.79; H, 5.16; N, 14.00.

EXAMPLE 4

Preparation of N-(6-Indolyl)-2-[(4-methoxybenzoyl)amino]benzamide

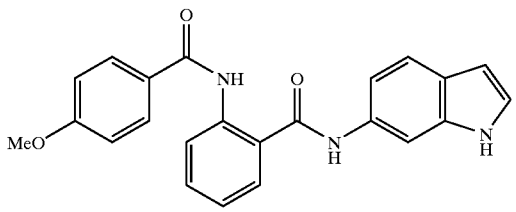

A) N-(1-Boc-6-indolyl)-2-[(4-methoxybenzoyl)amino]benzamide

By methods substantially equivalent to those described in Example 1-C, N-(1-Boc-6-indolyl)-2-[(4-methoxybenzoyl)amino]benzamide (436 mg, 83%) was prepared from p-anisoyl chloride and 2-amino-N-(1-Boc-6-indolyl)benzamide.

$^1$H-NMR

FD-MS, m/e 485.1 (M$^+$)

Analysis for $C_{28}H_{27}N_3O_5$: Calc: C, 69.26; H, 5.60; N, 8.65; Found: C, 68.96; H, 5.73; N, 8.53.

B) N-(6-Indolyl)-2-[(4-methoxybenzoyl)amino]benzamide

By methods substantially equivalent to those described in Example 2-F, N-(6-indolyl)-2-[(4-methoxybenzoyl)amino]benzamide (76 mg, 94%) was prepared from N-(1-Boc-6-indolyl)-2-[(4-methoxybenzoyl)amino]benzamide.

$^1$H-NMR

FD-MS, m/e (M$^+$)

Analysis for $C_{23}H_{19}N_3O_3 \cdot 0.5H_2O$: Calc: C, 70.04; H, 5.11; N, 10.65; Found: C, 70.13; H, 4.99; N, 10.37.

EXAMPLE 5

Preparation of 2-[(4-t-Butylbenzoyl)amino]-N-(6-indolinyl)benzamide

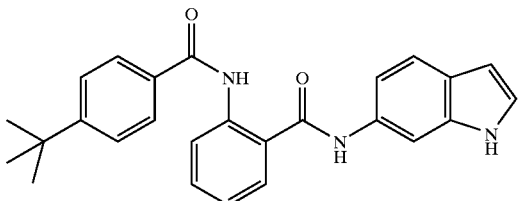

A) 1-Boc-6-aminoindoline

By methods substantially equivalent to those described in Example 1-B, 1-Boc-6-aminoindoline (2.2 g, 98%) was prepared from 1-Boc-6-aminoindole.

$^1$H NMR

B) N-(1-Boc-6-indolinyl)-2-nitrobenzamide

By methods substantially equivalent to those described in Example 1-C, N-(1-Boc-6-indolinyl)-2-nitrobenzamide (2.5 g, 100%) was prepared from 1-Boc-6-aminoindoline.

$^1$H NMR

FD-MS, m/e 383 (M$^+$)

Anal. for $C_{20}H_{21}N_3O_5$: Calc: C, 62.66; H, 5.52; N, 10.96; Found: C, 62.58; H, 5.46; N, 10.66.

C) 2-Amino-N-(1-Boc-6-indolinyl)benzamide

By methods substantially equivalent to those described in Example 1-B, 2-amino-N-(1-Boc-6-indolinyl)benzamide (0.92 g, 100%) was prepared from N-(1-Boc-6-indolinyl)-2-nitrobenzamide.

$^1$H NMR

FD-MS, m/e 353 (M$^+$)

Anal. for $C_{20}H_{23}N_3O_3 \cdot H_2O$: Calc: C, 64.68; H, 6.78; N, 11.31; Found: C, 64.48; H, 6.64; N, 11.19.

D) N-(1-Boc-6-indolinyl)-2-[(4-t-butylbenzoyl)amino]benzamide

By methods substantially equivalent to those described in Example 1-C, N-(1-Boc-6-indolinyl)-2-[(4-t-butylbenzoyl)amino]benzamide (245 mg, 69%) was prepared from 4-t-butyl-benzoyl chloride and N-(1-Boc-6-indolinyl)-2-aminobenzamide.

$^1$H NMR

FD-MS, m/e 513.2 (M$^+$)

Anal. for $C_{31}H_{35}N_3O_4$: Calc: C, 72.49; H, 6.87; N, 8.18; Found: C, 72.70; H, 6.97; N, 8.16.

E) 2-[(4-t-Butylbenzoyl)amino]-N-(6-indolinyl)benzamide

By methods substantially equivalent to those described in Example 1-F, 2-[(4-t-butylbenzoyl)amino]-N-(6-indolinyl)benzamide (87 mg, 54%) was prepared from N-(1-Boc-6-indolinyl)-2-[(4-t-butylbenzoyl)amino]benzamide.

$^1$H NMR

FD-MS, m/e 413.4 (M$^+$)

Anal. for $C_{26}H_{27}N_3O_2 \cdot 0.3H_2O$: Calc: C, 74.55; H, 6.64; N, 10.03; Found: C, 74.75; H, 6.80; N, 9.38.

EXAMPLE 6

Preparation of N-(6-Indolinyl)-2-[(4-methoxybenzoyl)amino]benzamide

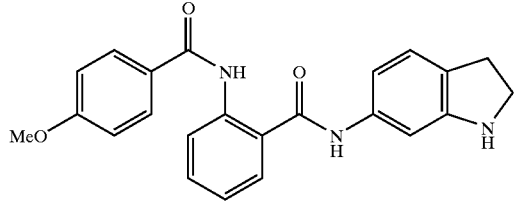

A) N-(1-Boc-6-indolinyl)-2-[(4-methoxybenzoyl)amino]benzamide

By methods substantially equivalent to those described in Example 1-C, N-(1-Boc-6-indolinyl)-2-[(4-methoxybenzoyl)amino]benzamide (250 mg, 39%) was prepared from p-anisoyl chloride and 2-amino-N-(1-Boc-6-indolinyl)benzamide.

$^1$H NMR

B) N-(6-Indolinyl)-2-[(4-methoxybenzoyl)amino]benzamide

By methods substantially equivalent to those described in Example 1-F, N-(6-indolinyl)-2-[(4-methoxybenzoyl)

amino]benzamide (160 mg, 100%) was prepared from N-(1-Boc-6-indolinyl)-2-[(4-methoxybenzoyl)amino]benzamide.

¹H NMR

FD-MS, m/e 387 (M⁺)

Anal. for $C_{23}H_{21}N_3O_3 \cdot 0.5H_2O$: Calc: C, 69.69; H, 5.59; N, 10.59; Found: C, 69.79; H, 5.28; N, 10.37.

EXAMPLE 7

Preparation of 2-[(4-t-Butylbenzoyl)amino]-N-(3-methyl-6-indazolyl)benzamide

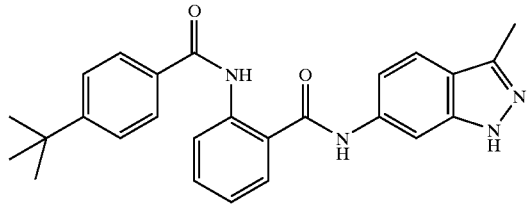

A) 1-Boc-3-methyl-6-nitroindazole

By methods substantially equivalent to those described in Example 1-A, 1-Boc-3-methyl-6-nitroindazole (3 g, 64%) was prepared from 3-methyl-6-nitro-indazole (*Chem. Abstr.*, (1966), 65, p 2245).

¹H NMR

FD-MS, m/e (M⁺)

Anal. for $C_{13}H_{15}N_3O_4$: Calc: C, 56.31; H, 5.45; N, 15.15; Found: C, 55.86; H, 5.62; N, 14.80.

B) 6-Amino-1-Boc-3-methylindazole

By methods substantially equivalent to those described in Example 2-B, 6-amino-1-Boc-3-methylindazole (2.26 g, 85%) was prepared from 1-Boc-3-methyl-6-nitroindazole.

¹H NMR

FD-MS, m/e (M⁺)

Anal. for $C_{13}H_{17}N_3O_2$: Calc: C, 63.14; H, 6.93; N, 16.99; Found: C, 62.84; H, 6.93; N, 17.05.

C) N-(1-Boc-3-methyl-6-indazolyl)-2-nitrobenzamide

By methods substantially equivalent to those described in Example 1-C, N-(1-Boc-3-methyl-6-indazolyl)-2-nitrobenzamide (2.07 g, 100%) was prepared from 2-nitrobenzoyl chloride and 6-amino-1-Boc-3-methylindazole.

D) 2-Amino-N-(1-Boc-3-methyl-6-indazolyl)benzamide

By methods substantially equivalent to those described in Example 2-B, 2-amino-N-(1-Boc-3-methyl-6-indazolyl)benzamide (1.62 g, 89%) was prepared from N-(1-Boc-3-methyl-6-indazolyl)-2-nitrobenzamide.

¹H NMR

FD-MS, m/e 366.2 (M⁺)

Anal. for $C_{20}H_{22}N_4O_3$: Calc: C, 65.55; H, 6.05; N, 15.29; Found: C, 65.54; H, 6.04; N, 15.11.

E) N-(1-Boc-3-methyl-6-indazolyl)-2-[(4-t-butylbenzoyl)amino]benzamide

By methods substantially equivalent to those described in Example 1-C, N-(1-Boc-3-methyl-6-indazolyl)-2-[(4-t-butylbenzoyl)amino]benzamide (1.21 g, 96%) was prepared from 4-t-butylbenzoyl chloride and 2-amino-N-(1-Boc-3-methyl-6-indazolyl)benzamide.

¹H NMR

FD-MS, m/e 526 (M⁺)

Anal. for $C_{31}H_{34}N_4O_4$: Calc: C, 70.70; H, 6.51; N, 10.64; Found: C, 70.05; H, 6.51; N, 10.73.

F) 2-[(4-t-butylbenzoyl)amino]-N-(3-methyl-indazolyl)benzamide

By methods substantially equivalent to those described in Example 1-F, 2-[(4-t-butylbenzoyl)amino]-N-(3-methyl-6-indazolyl)benzamide (0.17 g, 57%) was prepared from N-(1-Boc-3-methyl-6-indazolyl)-2-[(4-t-butylbenzoyl)amino]benzamide.

¹H NMR

FD-MS, m/e 426.1 (M⁺)

Anal. for $C_{26}H_{26}N_4O_2 \cdot TFA$: Calc: C, 62.33; H, 4.86; N, 10.39; Found: C, 62.09; H, 4.70; N, 10.27.

EXAMPLE 8

Preparation of 2-[(4-t-Butylbenzoyl)amino]-N-(3-chloro-6-indazolyl)benzamide

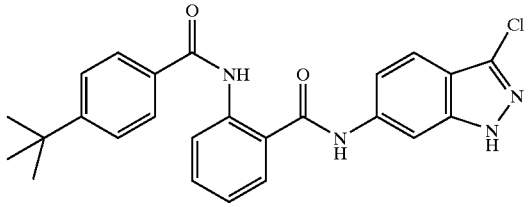

A) 1-Boc-3-chloro-6-nitroindazole

By methods substantially equivalent to those described in Example 1-A, 1-Boc-3-chloro-6-nitroindazole (3.49 g, 97%) was prepared from 3-chloro-6-nitro-indazole.

¹H NMR

FD-MS, m/e 297.1 (M⁺)

Anal. for $C_{12}H_{12}ClN_3O_4$: Calc: C, 48.41; H, 4.06; N, 14.11; Found: C, 48.65; H, 3.99; N, 14.22.

B) 6-Amino-1-Boc-3-chloroindazole

By methods substantially equivalent to those described in Example 2-B, 6-amino-1-Boc-3-chloroindazole (2.35 g, 88%) was prepared from 1-Boc-3-chloro-6-nitroindazole.

¹H NMR

FD-MS, m/e 267.1 (M⁺)

Anal. for $C_{12}H_{14}ClN_3O_2$: Calc: C, 53.84; H, 5.20; N, 16.70; Found: C, 53.74; H, 5.30; N, 16.65.

C) N-(1-Boc-3-chloro-6-indazolyl)-2-nitrobenzamide

By methods substantially equivalent to those described in Example 1-C, N-(1-Boc-3-chloro-6-indazolyl)-2-nitrobenzamide (2.1 g, 100%) was prepared from 1-Boc-3-chloro-6-aminoindazole.

¹H NMR

FD-MS, m/e 416.0 (M⁺)

Anal. for $C_{19}H_{17}ClN_4O_5$: Calc: C, 54.75; H, 4.11; N, 13.44; Found C, 54.94; H, 4.03; N, 13.30.

D) 2-Amino-N-(1-Boc-3-chloro-6-indazolyl)benzamide

By methods substantially equivalent to those described in Example 2-B, 2-amino-N-(1-Boc-3-chloro-6-indazolyl)-benzamide (1.58 g, 83%) was prepared from N-(1-Boc-3-chloro-6-indazolyl)-2-nitrobenzamide.

¹H NMR

FD-MS, m/e 386 (M⁺)

E) N-(1-Boc-3-chloro-6-indazolyl)-2-[(4-t-butylbenzoyl)amino]benzamide

By methods substantially equivalent to those described in Example 1-C, N-(1-Boc-3-chloro-6-indazolyl)-2-[(4-t-butylbenzoyl)amino]benzamide (1.32 g, 81%) was prepared from 4-t-butylbenzoyl chloride and 2-amino-N-(1-Boc-3-chloro-6-indazolyl)benzamide.

¹H NMR

FD-MS, m/e 546 (M⁺)

Anal. for $C_{30}H_{31}ClN_4O_4$: Calc: C, 65.87; H, 5.71; N, 10.24; Found: C, 65.61; H, 5.71; N, 10.18.

F) 2-[(4-t-butylbenzoyl)amino]-N-(3-chloro-6-indazolyl)benzamide

By methods substantially equivalent to those described in Example 1-F, 2-[(4-t-butylbenzoyl)amino]-N-(3-chloro-6-indazolyl)benzamide (0.15 g, 48%) was prepared from N-(1-Boc-3-chloro-6-indazolyl)]-2-[(4-t-butylbenzoyl)amino]benzamide.

$^1$H NMR

FD-MS, m/e 446 (M$^+$)

Anal. for $C_{25}H_{23}ClN_4O_2$: Calc: C, 67.18; H, 5.19; N, 12.54; Found: C, 67.17; H, 5.05; N, 12.31.

EXAMPLE 9

Preparation of $N^2$-(4-t-Butylbenzoyl)-$N^1$-(6-indazolylcarbonyl)-1,2-benzenediamine

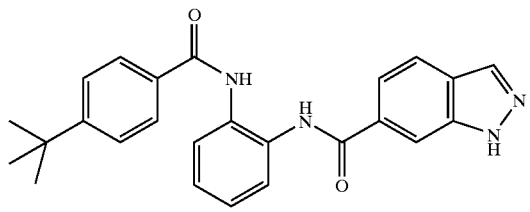

A) 2-[(4-t-Butylbenzoyl)amino]nitrobenzene

By methods substantially equivalent to those described in Example 3-A, 2-[(4-t-butylbenzoyl)amino]nitrobenzene (21.6 g, 100%) was prepared from 4-t-butylbenzoyl chloride and 2-nitroaniline.

$^1$H NMR

B) $N^2$-(4-t-butylbenzoyl)-1,2-benzenediamine

By methods substantially equivalent to those described in Example 1-B, $N^2$-(4-t-butylbenzoyl)-1,2-benzenediamine (19.87 g, 79%) was prepared from 2-[(4-t-butylbenzoyl)amino]nitrobenzene.

$^1$H NMR

FD-MS, m/e 298.2 (M$^+$)

C) $N^2$-(4-t-Butylbenzoyl)-$N^1$-(6-indazolylcarbonyl)-1,2-benzenediamine

To a stirring solution of $N^2$-(4-t-butylbenzoyl)-1,2-benzenediamine (830 mg, 3.1 mmol) and 6-indazolecarboxylic acid (European Pat. Appln. Pub. No. 242 167 A2, p 43) (500 mg, 3.1 mmol) in DMF (5 mL) was added EDC (1.19 g, 6.2 mmol). After 12 h, the solvent was removed in vacuo and the residue was dissolved in ethyl acetate and washed twice with water and twice with brine. The organic phase was dried with MgSO$_4$, filtered and concentrated in vacuo, then chromatographed over silica gel, eluting with a solvent gradient of dichloromethane through 5% methanol/dichloromethane. The product containing fractions were combined and concentrated in vacuo to give 330 mg (26%) of an off-white solid.

$^1$H NMR

FD-MS, m/e 412 (M$^+$)

Anal. for $C_{24}H_{24}N_4O_2$: Calc: C, 72.80; H, 5.87; N, 13.58; Found: C, 72.15; H, 5.80; N, 13.19.

EXAMPLE 10

Preparation of $N^2$-(4-t-Butylbenzoyl)-$N^1$-(6-indolylcarbonyl)-1,2-benzenediamine

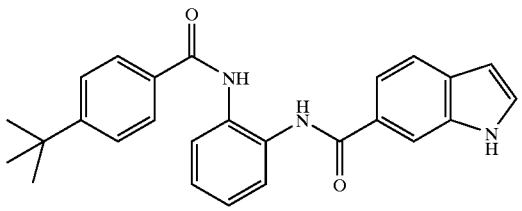

By methods substantially equivalent to those described in Example 9-C, $N^2$-(4-t-butylbenzoyl)-$N^1$-(6-indolylcarbonyl)-1,2-benzenediamine (0.10 g, 20%) was prepared from $N^2$-(4-t-butylbenzoyl)-1,2-benzenediamine and indole-6-carboxylic acid.

$^1$H NMR

FD-MS, m/e 411.1 (M$^+$)

Anal. for $C_{26}H_{25}N_3O_2 \cdot 0.3H_2O$: Calc: C, 74.91; H, 6.19; N, 10.07; Found: C, 74.94; H, 6.44; N, 9.77.

EXAMPLE 11

Preparation of $N^2$-(4-t-butylbenzoyl)-$N^1$-(6-indazolylcarbonyl)-4-methoxycarbonyl-1,2-benzenediamine

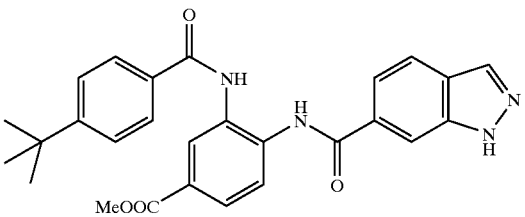

A) $N^2$-(4-t-Butylbenzoyl)-4-methoxycarbonyl-1,2-benzenediamine

To a stirring solution of 4-methoxycarbonyl-1,2-benzenediamine (8.5 g, 51 mmol) and pyridine (4.1 mL, 51 mmol) in acetonitrile (225 mL) at 0° C. was added via an addition funnel a solution of 4-t-butylbenzoyl chloride (10 g, 51 mmol) in acetonitrile (25 mL). After 3 h, the mixture was concentrated to a volume of about 20 mL in vacuo and then diluted with ethyl acetate (300 mL) and water (100 mL). The phases were separated and the organic phase was washed twice with 1 M citric acid, once with brine, twice with satd aq NaHCO$_3$ and once again with brine. The organic phase was then dried with MgSO$_4$, filtered and partially concentrated in vacuo. After standing for 48 h, the resulting precipitate was filtered, washed with ethyl acetate and dried in vacuo to give 8.2 g (48%) of off white solid. By a similar procedure, a second crop of 2.6 g (16%) was isolated from the mother liquor.

$^1$H NMR

FD-MS, m/e 326.2 (M$^+$)

Anal. for $C_{19}H_{22}N_2O_3$: Calc: C, 69.92; H, 6.79; N, 8.58; Found: C, 70.02; H, 6.91; N, 8.61.

B) $N^2$-(4-t-Butylbenzoyl)-$N^1$-(6-indazolylcarbonyl)-4-methoxycarbonyl-1,2-benzenediamine By methods substantially equivalent to those described in Example 9-C, $N^2$-(4-t-butylbenzoyl)]-$N^1$-(6-indazolylcarbonyl)-4-methoxycarbonyl-1,2- benzenediamine (0.1 g, 5%) was prepared from 4-methoxycarbonyl-N²-(4-t-butylbenzoyl)-1,2-benzenediamine and 6-indazolecarboxylic acid.

¹H NMR
FD-MS, m/e 438.3 (M⁺)
Anal. for $C_{26}H_{22}N_4O_3$: Calc: C, 68.92; H, 5.57; N, 11.91; Found: C, 68.94; H, 5.62; N, 11.79.

EXAMPLE 12

Preparation of N²-(4-t-Butylbenzoyl)-N¹-(6-indolinyl-carbonyl)-1,2-benzenediamine

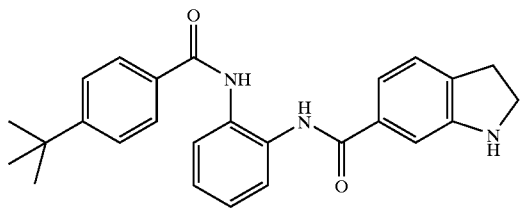

To a stirring solution of N²-(4-t-butylbenzoyl)-N¹-(6-indolylcarbonyl)-1,2-benzenediamine (0.1 g, 0.24 mmol) in acetic acid (1 mL) was added NaBH₃CN (0.046 g, 0.73 mmol). After 2 h, the mixture was diluted with water (10 mL), the pH was basified with conc aq NaHCO₃ and the aqueous phase was extracted twice with ethyl acetate. The combined ethyl acetate phase was washed with water and brine, then dried with MgSO₄, filtered and concentrated in vacuo to give 70 mg (70%) of white solid.

¹H NMR
FD-MS, m/e 413.52 (M⁺)
Anal. for $C_{26}H_{27}N_3O_2 \cdot 1.3H_2O$: Calc: C, 71.47; H, 6.83; N, 9.61; Found: C, 71.53; H, 7.00; N, 9.02.

EXAMPLE 13

Preparation of N¹-(6-Benzimidazolylcarbonyl)-N²-(4-t-butylbenzoyl)-1,2-benzenediamine

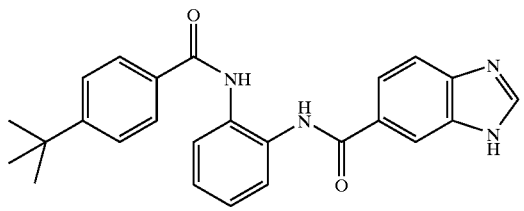

A) N²-(4-t-butylbenzoyl)-N¹-(1-tosylbenzimidazol-6-ylcarbonyl)-1, 2-benzenediamine By methods substantially equivalent to those described in Example 9-C, N²-(4-t-butylbenzoyl)-N¹-(1-tosylbenzimidazol-6-ylcarbonyl)-1,2-benzenediamine (0.432 g, 21%) was prepared from 1-tosylbenzimidazole-6-carboxylic acid and N²-(4-t-butylbenzoyl)-1,2-benzenediamine.

¹H NMR
FD-MS, m/e 566 (M⁺)
Anal. for $C_{32}H_{30}N_4O_4S$: Calc: C, 67.83; H, 5.34; N, 9.89; Found: C, 67.56; H, 5.50; N, 9.77.

B) N¹-(6-Benzimidazolylcarbonyl)-N²-(4-t-butylbenzoyl)-1,2-benzenediamine

To a stirring solution of N²-(4-t-butylbenzoyl)-N¹-(1-tosylbenzimidazol-6-ylcarbonyl)-1,2-benzenediamine (360 mg, 0.63 mmol) in THF (10 mL) was added HOBT (1.36 g, 10 mmol). After stirring for 24 h, the solvent was removed in vacuo. The residue was dissolved in dichloromethane and washed with satd aq NaHCO₃. The organic phase was allowed to stand overnight, and the resulting precipitate was filtered and dried to give 140 mg (54%) of white solid.

¹H NMR
FD-MS, m/e 412.1 (M⁺)
Anal. for $C_{25}H_{24}N_4O_2$: Calc: C, 72.80; H, 5.87; N, 13.58; Found: C, 73.01; H, 6.15; N, 13.57.

EXAMPLE 14

Preparation of N¹-(6-Benzotriazolylcarbonyl)-N²-[(4-t-butylbenzoyl)amino]-1,2-benzenediamine

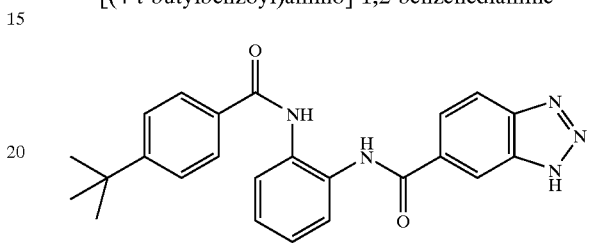

By methods substantially equivalent to those described in Example 9-C, N¹-(6-benzotriazolylcarbonyl)-N²-[(4-t-butylbenzoyl)amino]-1,2-benzenediamine (400 mg, 31%) was prepared from benzotriazole-6-carboxylic acid and N²-[(4-t-butylbenzoyl)amino]-1,2-benzenediamine ¹H NMR
FD-MS, m/e 413 (M⁺)
Anal. for $C_{24}H_{23}N_5O_2$: Calc: C, 67.71; H, 5.61; N, 16.94; Found: C, 67.47; H, 5.64; N, 16.73.

EXAMPLE 15

Preparation of N-(6-Benzimidazolyl)-2-[(4-t-butylbenzoyl)amino]benzamide

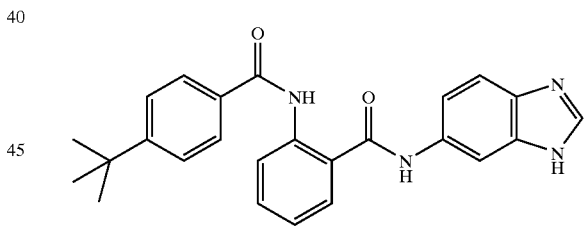

A) 5-Nitro-1-tosylbenzimidazole

To a stirring solution of 5-nitrobenzimidazole (7.5 g, 46 mmol) in THF (300 mL) and water (150 mL) was added K₂CO₃ (15.9 g, 115 mmol), followed by p-toluenesulfonyl chloride (11.4 g, 46 mmol). After stirring for 16 h, solvents were removed in vacuo and the residue was partitioned between ethyl acetate and water. The layers were separated and the organic phase was washed with brine, then dried with MgSO₄, filtered and concentrated in vacuo. The crude solid was dissolved in choloroform and chromatographed over a silica gel column with a gradient of chloroform through 10% methanol/chloroform. The product containing fractions were combined and concentrated in vacuo to give 11.4 g (79%) of light yellow solid.

¹H NMR
FD-MS, m/e 317 (M⁺)
Anal. for $C_{14}H_{11}N_3O_4S$: Calc: C, 52.99; H, 3.49; N, 13.24; Found: C, 52.92; H, 3.31; N, 13.16.

B) 2-Nitro-N-(1-tosylbenzimidazol-6-yl)benzamide

By methods substantially equivalent to those described in Example 1-B followed by those of Example 1-C, 2-nitro-N-(1-tosylbenzimidazol-6-yl)benzamide (6.8 g, 99%) was prepared from 5-nitro-1-tosylbenzimidazole.

$^1$H NMR

FD-MS, m/e 436.1 (M$^+$)

Anal. for $C_{21}H_{16}N_4O_5S$: Calc: C, 57.79; H, 3.69; N, 12.84; Found: C, 57.52; H, 3.70; N, 13.11.

C) N-(6-Benzimidazolyl)-2-[(4-t-butylbenzoyl)amino]benzamide

By methods substantially equivalent to those described in Examples 1-B and 1-C, 3.7 g (6.5 mmol) of crude 2-[(4-t-butylbenzoyl)amino]-N-(1-tosylbenzimidazol-6-yl)benzamide was prepared from 2-nitro-N-(1-tosylbenzimidazol-6-yl)benzamide and 4-t-butylbenzoyl chloride. This material was dissolved in p-dioxane (50 mL) and a solution of LiOH.H$_2$O (0.48 g, 11 mmol) in water (25 mL) was added with vigorous stirring. After 16 h, the solvents were removed in vacuo and the residue was partitioned between chloroform and satd aq NaHCO$_3$. The phases were separated and the organic phase was washed with water, followed by brine, then dried over MgSO$_4$, filtered and concentrated in vacuo. The residue was triturated with ether, filtered and the solid was dissolved in a minimal amount of chloroform and chromatographed over a silica gel column with 10% methanol/chloroform. The product containing fractions were combined and concentrated in vacuo to give 0.97 g (36% overall) of off-white solid.

$^1$H NMR

FD-MS, m/e 412.1 (M$^+$)

Anal. for $C_{25}H_{24}N_4O_2$: Calc: C, 72.80; H, 5.86; N, 13.58; Found: C, 73.08; H, 5.79; N, 13.67.

EXAMPLE 16

Preparation of 3-[(4-t-Butylbenzoyl)amino]-N-(6-indazolyl)-2-thiophenecaboxamide

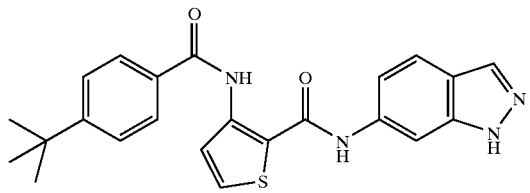

A) Methyl 3-[(4-t-Butylbenzoyl)amino]-2-thiophenecarboxylate

A flame dried flask was charged with methyl 3-amino-2-thiophenecarboxylate (5.0 g, 35.0 mmol), pyridine (2.82 mL, 35.0 mmol), and dry methylene chloride (160 mL). The solution was cooled to 0° C. and 4-tert-butylbenzoyl chloride (6.21 mL, 31.8 mmol) was added. After 1 h, the solvent was removed in vacuo and the remaining material was dissolved in ethyl acetate. The organic phase was washed four times with water and once with brine. The organic phase was then dried over magnesium sulfate, filtered, and the solvent removed in vacuo. The crude product was purified by column chromatography over silica gel using an eluent of 2% ethyl acetate in hexane and 5% ethyl acetate in hexane to afford the product (9.67g, 96% yield).

$^1$H NMR(CDCl$_3$) δ1.36(s, 9H), 3.93(s, 3H), 7.54(d, J=8.4 Hz, 2H), 7.54(d, J=5.4 Hz, 1H), 7.95(d, J=8.4 Hz, 2H), 8.30(d, J=5.4 Hz, 1H), 11.16(s, 1H);

FD-MS, m/e 317 (M$^+$)

Anal. for $C_{17}H_{19}NO_3$: Calc: C, 64.33; H, 6.03; N, 4.42; Found: C, 64.39; H, 5.98; N, 4.46.

B) 3-[(4-t-Butylbenzoyl)amino]-2-thiophenecarboxylic Acid

To a stirring solution of methyl 3-[(4-t-butylbenzoyl)amino]-2-thiophenecarboxylate (9.67g, 30 mmol) in dioxane (75 mL) was added 2 M sodium hydroxide (75 mL). After 16 h, the mixture was acidified to pH 2 with 5 M hydrochloric acid, then diluted with ethyl acetate. The phases were separated and the aqueous layer was extracted a total of 3 times with ethyl acetate. The combined ethyl acetate fractions were dried over magnesium sulfate, filtered, and the solvent was removed in vacuo to afford the product (8.09 g, 89% yield).

$^1$H NMR(CDCl$_3$) δ1.36(s, 9H), 7.54(d, J=8.4 Hz, 2H), 7.61(d, J=5.1 Hz, 1H), 7.92(d, J=8.4 Hz, 2H), 8.34(d, J=5.1 Hz, 1H), 11.04(s, 1H);

FD-MS, m/e 303 (M$^+$)

Anal. for $C_{16}H_{17}NO_3S$: Calc: C, 63.34; H, 5.93; N, 4.62; Found: C, 63.56; H, 5.93; N, 4.32.

C) 2-(4-t-Butylphenyl)-4-oxo-4H-thieno[3,2-d][1,3]oxazine

To a suspension of 3-[(4-t-butylbenzoyl)amino]-2-thiophenecarboxylic acid (8.09 g, 27 mmol) in dry dichloromethane (135 mL) was added oxalyl chloride (11.8 mL, 135 mmol). The mixture was carefully heated with a heat gun in order to dissolve the starting material and initiate the reaction. The heat was then removed and after stirring for 2 h, the solvents were removed in vacuo. The residue was dissolved in dry dichloromethane (135 mL), and pyridine (2.2 mL, 27 mmol) was added. After 1 h, solvent was removed in vacuo. The residue was partitioned between ethyl acetate and water, and the organic phase was washed four times with water and once with brine. The organic phase was then dried over magnesium sulfate, filtered, and the solvent removed in vacuo. The crude product was purified by column chromatography over silica gel using an eluent of 10% ethyl acetate in hexane to afford the product (7.44 g, 96% yield).

$^1$H NMR(CDCl$_3$) δ1.37(s, 9H), 7.35(d, J=5.1 Hz, 1H), 7.52(d, J=8.4 Hz, 2H), 7.91(d, J=5.1 Hz, 1H), 8.22(d, J=8.4 Hz, 2H);

FD-MS, m/e 285 (M$^+$)

Anal. for $C_{16}H_{15}NO_2S$: Calc: C, 67.34; H, 5.30; N, 4.91; Found: C, 67.51; H, 5.56; N, 4.76.

D) 3-[(4-t-Butylbenzoyl)amino]-N-(6-indazolyl)-2-thiophenecaboxamide

To a stirring solution of 1-Boc-6-aminoindazole (100 mg, 0.43 mmol) in tetrahydrofuran (2 mL) at 0° C. was added a solution of potassium bis(trimethylsilyl)amide (180 mg, 0.90 mmol) in tetrahydrofuran (2 mL). After 15 min, this solution was transferred via syringe to a stirring solution of 2-(4-t-butylphenyl)-4-oxo-4H-thieno[3,2-d][1,3]oxazine (122 mg, 0.43 mmol) in tetrahydrofuran (2 mL). After 45 min, saturated ammonium chloride was added, the mixture was diluted with ethyl acetate, and the phases were separated. The aqueous phase was extracted 3 times with ethyl acetate. The combined ethyl acetate extracts were then washed once with brine, dried over magnesium sulfate, filtered, and the solvent removed in vacuo. The crude product was purified by column chromatography over silica gel using an eluent of 40% ethyl acetate in hexane and 50% ethyl acetate in hexane to afford the product (34 mg, 15%).

$^1$H NMR

FD-MS, m/e 418 (M$^+$)

Anal. for $C_{23}H_{22}N_4O_2S$: Calc: C, 66.01; H, 5.30; N, 13.39; Found C, 66.24; H, 5.30; N, 13.41.

EXAMPLE 17

Preparation of N-(6-Indazolyl)-2-(5-t-butyl-1,3-dihydro-1,3-dioxo-2H-isoindol-2-yl)benzamide

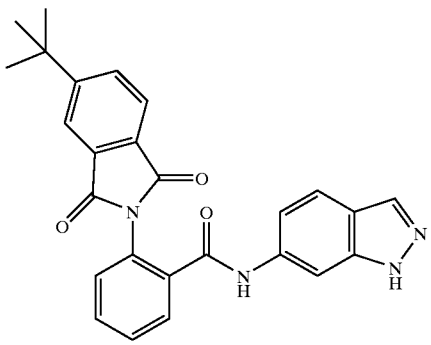

To a stirring solution of 2-amino-N-(1-Boc-6-indazolyl)benzamide (1 g, 2.8 mmol) in THF (30 mL) was added 4-t-butylphthalic anhydride (1.2 g, 5.9 mmol) and the solution was heated to reflux. After 72 h, the vessel was cooled and the volume was reduced to about 10 mL in vacuo. The mixture was diluted with diethyl ether (20 mL) and after sonication, a white solid was collected. This solid was processed by methods substatially equivalent to those described in Example 2-F to give 200 mg of N-(6-indazolyl)-2-(5-t-butyl-1,3-dihydro-1,3-dioxo-2H-isoindol-2-yl)benzamide.

$^1$H NMR

FD-MS, m/e 438.2 (M$^+$)

Anal. for $C_{26}H_{22}N_4O_3 \cdot 0.5H_2O$: Calc: C, 69.79; H, 5.18; N, 12.51; Found: C, 69.69; H, 5.48; N, 11.56.

EXAMPLE 18

Preparation of 2-[(4-t-Butylbenzoyl)amino]-N-(6-indazolyl)-3-methylbenzamide

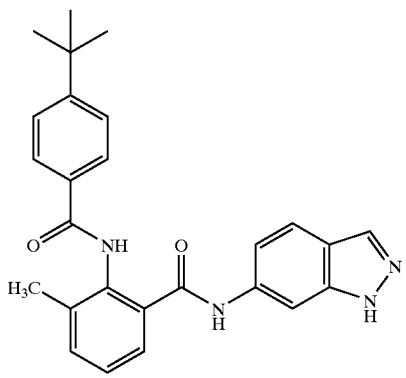

A) N-(1-Boc-6-indazolyl)-3-methyl-2-nitrobenzamide

To a stirring solution of 3-methyl-2-nitrobenzoic acid (1.8 g, 10.1 mmol) and 1-Boc-6-amino-indazole (2.37 g, 10.1 mmol) in DMF (20 mL) was added EDC (3.17 g, 15.2 mmol). After stirring for 16 h, the solvent was removed in vacuo and the residue was partitioned between ethyl acetate and 1 M citric acid. The layers were separated and the organic phase was washed again with 1 M citric acid, once with water, twice with satd aq NaHCO$_3$, and once with brine. The organic phase was then dried over MgSO$_4$, filtered and concentrated in vacuo. The residue was dissolved in a minimal volume of chloroform and chromatographed over silica gel, eluting with a gradient of 40% ethyl acetate/hexanes through 70% ethyl acetate/hexanes. The product containing fractions were combined and concentrated in vacuo to give 2.34 g (58%) of off-white solid.

B) 2-Amino-N-(1-Boc-6-indazolyl)-3-methylbenzamide

By methods substantially equivalent to those described in Example 1-B, 2-amino-N-(1-Boc-6-indazolyl)-3-methylbenzamide (1.1 g, 73%) was prepared from N-(1-Boc-6-indazolyl)-3-methyl-2-nitrobenzamide.

$^1$H NMR

FD-MS, m/e 366.4 (M$^+$)

C) N-(1-Boc-6-indazolyl)-2-[(4-t-butylbenzoyl)amino]-3-methylbenzamide

By methods substantially equivalent to those described in Example 1-C, N-(1-Boc-6-indazolyl)-2-[(4-t-butylbenzoyl)amino]-3-methylbenzamide (0.46 g, 80%) was prepared from 2-amino-N-(1-Boc-6-indazolyl)-3-methylbenzamide and 4-t-butylbenzoyl chloride.

$^1$H NMR

FD-MS, m/e 526 (M$^+$)

Anal. for $C_{31}H_{34}N_4O_4$: Calc: C, 70.70; H, 6.51; N, 10.64; Found C, 70.55; H, 6.41; N, 10.54.

D) 2-[(4-t-Butylbenzoyl)amino]-N-(6-indazolyl)-3-methylbenzamide

By methods substantially equivalent to those described in Example 1-F, 2-[(4-t-butylbenzoyl)amino]-N-(6-indazolyl)-3-methylbenzamide (0.19 g, 79%) was prepared from N-(1-Boc-6-indazolyl)-2-[(4-t-butylbenzoyl)amino]-3-methylbenzamide.

$^1$H NMR

FD-MS, m/e 426.1 (M$^+$)

Anal. for $C_{26}H_{26}N_4O_2$: Calc: C, 73.22; H, 6.14; N, 13.14; Found C, 72.98; H, 6.26; N, 12.89.

EXAMPLE 19

Preparation of 2-[(4-t-Butylbenzoyl)amino]-N-(6-indazolyl)-3-methoxybenzamide

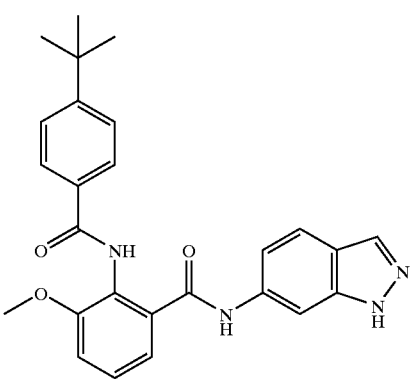

A) N-(1-Boc-6-indazolyl)-3-methoxy-2-nitrobenzamide

By methods substantially equivalent to those described in example 18-A, 1-[N-(1-Boc-6-indazolyl)]-2-nitro-3-methoxybenzamide (2.3 g, 56%) was prepared from 3-methoxy-2-nitrobenzoic acid and 1-Boc-6-aminoindazole.

$^1$H NMR

FD-MS, m/e 412.2 (M$^+$)

B) 2-Amino-N-(1-Boc-6-indazolyl)-3-methoxybenzamide

By methods substantially equivalent to those described in Example 2-B, 2-amino-N-(1-Boc-6-indazolyl)-3-methoxybenzamide (0.71 g, 93%) was prepared from 1-[N-(1-Boc-6-indazolyl)]-2-nitro-3-methoxybenzamide.

C) N-(1-Boc-6-indazolyl)-2-[(4-t-butylbenzoyl)amino]-3-methoxybenzamide

By methods substantially equivalent to those described in Example 1-C, N-(1-Boc-6-indazolyl)-2-[(4-t-butylbenzoyl)amino]-3-methoxybenzamide (0.45 g, 64%) was prepared from 2-amino-N-(1-Boc-6-indazolyl)-3-methoxybenzamide and 4-t-butylbenzoyl chloride.

$^1$H NMR

FD-MS, m/e 542.1 (M$^+$)

Anal. for $C_{31}H_{34}N_4O_5$: Calc: C, 68.62; H, 6.32; N, 10.32; Found C, 68.77; H, 6.38; N, 10.13.

D) 2-[(4-t-Butylbenzoyl)amino]-N-(6-indazolyl)-3-methoxybenzamide

By methods substantially equivalent to those described in Example 1-F, 2-[(4-t-butylbenzoyl)amino]-N-(6-indazolyl)-3-methoxybenzamide (0.19 g, 69%) was prepared from N-(1-Boc-6-indazolyl)-2-[(4-t-butylbenzoyl)amino]-3-methoxybenzamide.

$^1$H NMR

FD-MS, m/e 442.2 (M$^+$)

Anal. for $C_{26}H_{26}N_4O_3 \cdot 0.5H_2O$: Calc: C, 69.17; H, 6.03; N, 12.40; Found: C, 69.46; H, 6.09; N, 11.86.

EXAMPLE 20

Preparation of 2-[(4-Ethoxybenzoyl)amino]-N-(6-indazolyl)benzamide

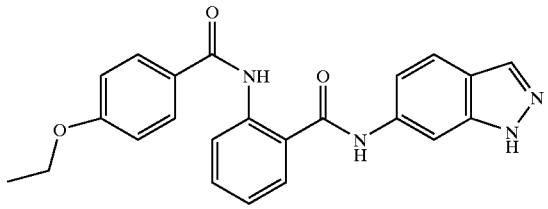

A) N-(1-Boc-6-indazolyl)-2-[(4-ethoxybenzoyl)amino]benzamide

By methods substantially equivalent to those described in Example 1-C, N-(1-Boc-6-indazolyl)-2-[(4-ethoxybenzoyl)amino]benzamide (100 mg, 27%) was prepared from 1-Boc-6-aminoindazole and 4-ethoxybenzoyl chloride.

$^1$H NMR

FD-MS, m/e 500.1 (M$^+$)

Anal. for $C_{28}H_{28}N_4O_5$: Calc: C, 67.19; H, 5.64; N, 11.19; Found: C, 66.73; H, 5.59; N, 10.72.

B) 2-[(4-Ethoxybenzoyl)amino]-N-(6-indazolyl)benzamide

By methods substantially equivalent to those described in Example 1-F, 2-[(4-ethoxybenzoyl)amino]-N-(6-indazolyl)benzamide (34 mg, 57%) was prepared from N-(1-Boc-6-indazolyl) -2- [(4-ethoxybenzoyl) amino]benzamide.

$^1$H NMR

FD-MS, m/e 400.2 (M$^+$)

Anal. for $C_{23}H_{20}N_4O_3 \cdot 0.7H_2O$: Calc: C, 66.89; H, 5.22; N, 13.56; Found: C, 67.07; H, 5.04; N, 13.22.

EXAMPLE 21

Preparation of 2-[(2-Butoxy-4-methoxybenzoyl)amino]-N-(6-indazolyl)benzamide

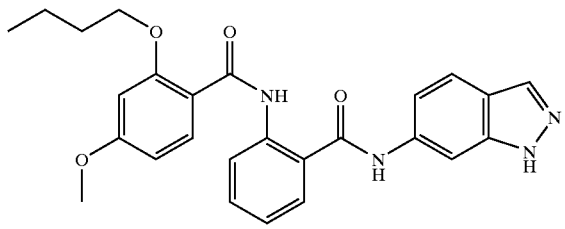

A) N-(1-Boc-6-indazolyl)-2-[(2-butoxy-4-methoxybenzoyl)amino]benzamide

By methods substantially equivalent to those described in Example 9-C, N-(1-Boc-6-indazolyl)-2-[(2-butoxy-4-methoxybenzoyl)amino]benzamide (183 mg, 30%) was prepared from 1-Boc-6-aminoindazole and 2-butoxy-4-methoxybenzoic acid.

$^1$H NMR

FD-MS, m/e 558.1 (M$^+$)

B) 2-[(2-Butoxy-4-methoxybenzoyl)amino]-N-(6-indazolyl)benzamide

By methods substantially equivalent to those described in Example 1-F, 2-[(2-butoxy-4-methoxybenzoyl)amino]-N-(6-indazolyl)benzamide was prepared.

$^1$H NMR

EXAMPLE 22

Preparation of 2-[(4-t-Butylbenzoyl)oxy]-N-(6-indazolyl)benzamide

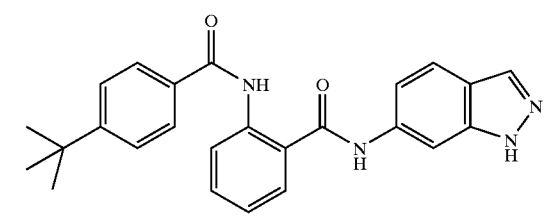

A) N-(1-Boc-6-indazolyl)-2-hydroxybenzamide

To a stirring solution of salicylic acid (1.06 g, 7.7 mmol) and DMF (1 drop) in dichloromethane (100 mL) at 0° C. was added oxalyl chloride (1.13 mL, mmol). After 1 h, the ice bath was removed and stirring was continued for 3.5 h. Solvent was removed under vacuum with minimum heat, and after evacuating further to remove residual oxalyl chloride, the residue was redissolved in dichloromethane (80 mL) and cooled to 0 ° C. To this solution was then added a solution of 1-Boc-6-aminoindazole (1.86 g, 8 mmol) in dichloromethane (10 mL). After stirring for 10 min, triethylamine (1.24 mL, 8 mmol) was added. After 1 h, the solution was transferred to a separatory funnel and washed with cold water (200 mL). The organic layer was then washed with cold satd aq NaHCO$_3$ (200 mL), dried over MgSO$_4$, filtered and concentrated under vacuum. The product was chromatographed over silica gel (0 to 60% EtOAc in hexane) and recrystallized from dichloromethane/hexanes to give 0.482 g (17%) of crystals.

mp 155–6° C.

$^1$H NMR (DMSO-d6) δ1.6 (s, 9H)), 7.0 (m, 3H), 7.44 (t, 1H), 7.55 (d, 1H), 7.84 (d, 1H), 7.94 (s,1H), 8.26 (s, 1H), 8.81) (s, 1H), 10.64 (s,1H), 11.60 (s, 1H);

FD-MS, m/e 353 (M+)

Anal. for $C_{19}H_{19}N_3O_4$: Calc: C, 64.58; H, 5.42; N, 11.89; Found: C, 64.00; H, 5.46; N, 11.55.

B) N-(1-Boc-6-indazolyl)-2-[(4-t-butylbenzoyl)oxy]benzamide

By methods substantially equivalent to those described in Example 1-C, N-(1-Boc-6-indazolyl)-2-[(4-t-butylbenzoyl)oxy]benzamide (239 mg, 26%) was prepared from 4-t-butylbenzoyl chloride and N-(1-Boc-6-indazolyl)-2-hydroxybenzamide.

mp 85–89° C.

$^1$H NMR (300 MHZ) δ1.36 (s, 9H), 1.75 (s, 1H), 7.21 (d, 1H), 7.29 (d, 1H), 7.45 (t, 1H), 7.53 (,d, 2H), 7.58 (t, 1H), 8.03 (d, 1H), 8.08 (s, 1H), 8.17 (d, 2H), 8.51 (s, 1H), 8.70 (s, 1H);

FD-MS, m/e 513 (M+)

Anal. for $C_{30}H_{31}N_3O_5$: Calc: C, 70.16; H, 6.08; N, 8.18; Found: C, 71.00, H, 6.33; N, 7.55.

C) 2-[(4-t-Butylbenzoyl)oxy]-N-(6-indazolyl)benzamide

By methods substantially equivalent to those described in Example 1-F, 2-[(4-t-butylbenzoyl)oxy]-N-(6-indazolyl)benzamide (21 mg, 28%) was prepared from N-(1-Boc-6-indazolyl)-2-[(4-t-butylbenzoyl)oxy]benzamide.

mp—70–73 ° C.

$^1$H NMR (DMSO-d6) δ1.28 (s, 9H), 7.20 (d, 1H), 7.43 (d, 1H) 7,47 (t,1H), 7.55 (d, 2H), 7.62 (d, 1H, 7.63 (t, 1H), 7.78 (d, 1H), 7.95 (s, 1H), 8.04 (d, 1H), 8.13 (d, 1H), 10.52 (s, 1H);

FD-MS, m/e 413 (M+)

Anal. for $C_{25}H_{23}N_3O_3$.TFA: Calc: C, 61.48; H, 4.59; N, 7.97; Found: C, 61.61; H, 4.75; N, 7.70.

EXAMPLE 23

Preparation of $N^1$-(6-Indolylcarbonyl)-$N^2$-[1-(4-pyridyl)-piperidin-4-yl]methoxycarbonyl-1,2-benzenediamine

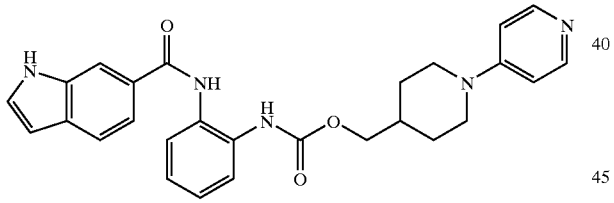

A) 2-Nitro-N-[[1-(4-pyridyl)piperidin-4-yl]methoxycarbonyl]aniline

A solution of 2-nitrophenyl isocyanate (4.25 g, 25.9 mmol) and 1-(4-pyridyl)-4-piperidinemethanol (4.13 g, 21.5 mmol) in dichloromethane (100 mL) was stirred at room temperature overnight (about 18h). The mixture was concentrated and the residue purified by flash chromatography (SiO$_2$; CHCl$_3$ to 5% MeOH/1% Et$_3$N in CHCl$_3$) to yield 7.55 g (96%) of the title compound.

$^1$H-NMR

FD-MS, m/e 357 (M+)

Analysis for $C_{18}H_{20}N_4O_4$: Calc: C, 60.67; H, 5.66; N, 15.72; Found: C, 60.43; H, 5.55; N, 15.69.

B) $N^1$-[[1-(4-Pyridyl)piperidin-4-yl]methoxycarbonyl]-1,2-benzenediamine

A solution of 2-nitro-N-[[1-(4-pyridyl)piperidin-4-yl]methoxycarbonyl]aniline (7.55 g, 21.2 mmol) and 5% Pd/C (4.00 g) in ethanol was placed under an atmosphere of hydrogen (1 atm). After consumption of the starting material was indicated by tlc (16–20 h), the mixture was filtered through diamotaceous earth using hot ethyl acetate to wash the filter cake. Concentration of the filtrate yielded 6.58 g (96%) of the title compound.

$^1$H-NMR

FD-MS, m/e 326 (M+)

Analysis for $C_{18}H_{22}N_4O_2$: Calc: C, 66.24; H, 6.79; N, 17.17; Found: C, 66.36; H, 6.81; N, 17.43.

C) $N^1$-(6-Indolylcarbonyl)-$N^2$-[[1-(4-pyridyl)piperidin-4-yl]methoxycarbonyl]-1,2-benzenediamine A solution of 1-benzyloxycarbonyl-6-indolecarboxylic acid (452 mg, 1.53 mmol), $N^1$-[[1-(4-pyridyl)piperidin-4-yl]methoxycarbonyl]-1,2-benzenediamine (500 mg, 1.53 mmol), and EDC (294 mg, 1.53 mmol) in DMF (2.5 mL) was allowed to stir overnight (about 18 h). The mixture was poured into ethyl acetate and H$_2$O, the aqueous layer was washed with EtOAc (3x), and the combined organic extracts were washed with 1 N NaOH (2x), H$_2$O, brine, and dried (K$_2$CO$_3$). Concentration and purification of the residue by flash chromatography (SiO$_2$) followed by recrystallization (MeOH/ether) yielded 60 mg (8%) of the title compound.

$^1$H-NMR

FD-MS, m/e 470 (M+)

Analysis for $C_{27}H_{27}N_5O_3$: Calc: C, 69.07; H, 5.80; N, 14.92; Found: C, 66.58; H, 6.01; N, 14.14.

EXAMPLE 24

Preparation of 2-[(4-t-Butylbenzoyl)amino]-N-(6-indazolyl)-5-[(methylsulfonyl)amino]benzamide

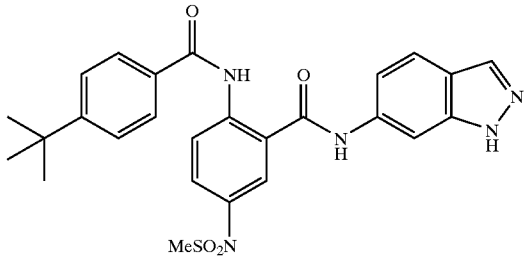

A) 6-Nitro-2-(4-t-butylphenyl)-4H-3,1-benzoxazin-4-one

To a mixture of 5-nitroanthranilic acid (24.59 g, 135 mmol) and pyridine (14.19 mL, 175.5 mmol, 1.3 eq) in DMF (140 mL) at 0° C., under N$_2$, was added 4-t-butylbenzoyl chloride (31.64 mL, 162 mmol, 1.2 eq) over 15 min. After warming to room temperature, the reaction mixture was heated to 80 ° C. for 4 h. The reaction mixture was cooled and poured into 700 mL ice-water and stirred to break up the solid material. Filtration, with water followed with 1:2 Et$_2$O:hexane washes, and vacuum drying (150° C./13 Pa/2 h) afforded a light brown solid as a mixture of acid and benzoxazinone (37.1 g, 80%). The solid was suspended in DMF (0.4 mL, 5.4 mmol, 0.05 eq) and methylene chloride (200 mL), under N$_2$, and oxalyl chloride (10.4 mL, 119.2 mmol, 1.1 eq) was added dropwise. Vigorous gas evolution was observed. The solid went into solution over 2 h. The mixture was concentrated to a volume of about 125 mL (cold) in vacuo and filtered to give a light tan solid (about 10 g). A second crop was about 85% pure (about 10 g). The mother liquor was evaporated to dryness an d vacuum dried (80 ° C./13 Pa/3 h) to afford a light brown solid product, 95% pure (about 12 g). Total yield 93.6%.

$^1$NMR: 1.32 (s, 9H), 7.65 (d, 2H, J=8.7 Hz), 7.89 (d, 1H, J=8.7 Hz), 8.16 (d, 2H, J=8.7 Hz), 8.35 (dd, 1H, J=8.7, 2.7 Hz), 8.75 (d, 1H, J=2.7 Hz).

B) 2-[(4-t-Butylbenzoyl)amino]-N-(6-indazolyl)-5-nitrobenzamide

To a stirring solution of 6-nitro-2-[4-t-butylphenyl]-4H-3,1-benzoxazin-4-one (1.5 g, 4.62 mmol) in toluene (25 mL) was added 6-aminoindazole (560 mg, 4.2 mmol) and the solution was heated to reflux. After about 24 h, the solution was cooled, filtered and the solid was washed with diethyl ether. The product was then chromatographed over silica gel, eluting with 25% ethyl acetate/hexanes. The product containing fractions were combined and concentrated in vacuo to give 810 mg (42%) of pale yellow solid.

$^1$H-NMR

FD-MS, m/e 457.2 (M$^+$)

C) N-(1-Boc-6-indazolyl)-2-[(4-t-butylbenzoyl)amino]-5-nitrobenzamide

To a stirring suspension of NaH (61 mg, 1.53 mmol) in THF (10 mL) was added 2-[(4-t-butylbenzoyl)amino]-N-(6-indazolyl)-5-nitrobenzamide (700 mg, 1.53 mmol) followed by a solution of di-t-butyl dicarbonate (330 mg, 1.53 mmol) in THF (20 mL). After 24 h, the mixture was diluted with ethyl acetate and washed with 1 M citric acid, water, satd aq NaHCO$_3$ and brine. The organic phase was then dried with MgSO$_4$, filtered and concentrated in vacuo. The residue was chromatographed over silica gel eluting with 25% ethyl acetate/hexanes to give 690 mg (81%) of an off-white solid.

$^1$H-NMR

FAB-MS, m/e 558.3 (MH$^+$)

Analysis for C$_{30}$H$_{31}$N$_5$O$_6$: Calc: C, 64.62; H, 5.60; N, 12.56; Found: C, 64.54; H, 5.67; N, 12.46.

D) 5-Amino-N-(1-Boc-6-indazolyl)-2-[(4-t-butylbenzoyl)amino]benzamide

By methods substantially equivalent to those described in Example 1-B, 5-amino-N-(1-Boc-6-indazolyl)-2-[(4-t-butylbenzoyl)amino]benzamide (175 mg, 45%) was prepared from N-(1-Boc-6-indazolyl)-2-[(4-t-butylbenzoyl)amino]-5-nitrobenzamide.

$^1$H-NMR

FD-MS, m/e 527.2 (M$^+$)

E) N-(1-Boc-6-indazolyl)-2-[(4-t-butylbenzoyl)amino]-5-[(methylsulfonyl)amino]benzamide To a stirring solution of 5-amino-N-(1-Boc-6-indazolyl)-2-[(4-t-butylbenzoyl)amino]benzamide (144 mg, 0.27 mmol) and pyridine (0.066 mL, 0.82 mmol) in dichloromethane (5 mL) and THF (5 mL) was added methanesulfonyl chloride (0.023 mL, 0.30 mmol). After stirring for 24 h, the solvent was removed in vacuo and the residue was dissolved in ethyl acetate and washed with 1 M citric acid, water, satd aq NaHCO$_3$, and brine. The organic phase was then dried with MgSO$_4$, filtered and concentrated in vacuo and the resulting solid was recrystallized from dichloromethane/hexanes to give 137 mg (83%) of tan solid.

$^1$H-NMR

FD-MS, m/e 605 (M$^+$)

Analysis for C$_{31}$H$_{35}$N$_5$O$_6$S: Calc: C, 61.47; H, 5.82; N, 11.56; Found: C, 61.70; H, 6.01; N, 11.47.

F) 2-[(4-t-Butylbenzoyl)amino]-N-(6-indazolyl)-5-[(methylsulfonyl)amino]benzamide By methods substantially equivalent to those described in Example 1-F, 2-[(4-t-butylbenzoyl)amino]-N-(6-indazolyl)-5-[(methylsulfonyl)amino]benzamide (79 mg, 78%) was prepared from N-(1-Boc-6-indazolyl)-2-[(4-t-butylbenzoyl)amino]-5-[(methylsulfonyl)amino]benzamide.

$^1$H-NMR

FD-MS, m/e 505.1 (M$^+$)

Analysis for C$_{26}$H$_{27}$N$_5$O$_4$S.TFA: Calc: C, 54.90; H, 4.62; N, 11.52; F, 8.43; Found: C, 55.35; H, 4.59; N, 11.05; F, 8.64.

EXAMPLE 25

Preparation of 2-[(4-t-Butylbenzoyl)amino]-N-(6-indazolyl)-4-[(methylsulfonyl)amino]benzamide

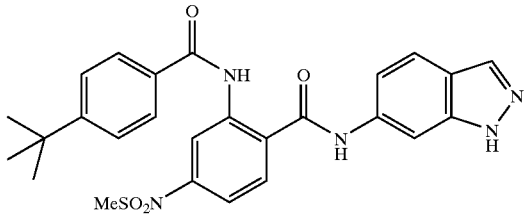

A) 7-Nitro-2-(4-t-butylphenyl)-4H-3,1-benzoxazin-4-one

By methods substantially equivalent to those described in Example 24-A, 7-nitro-2-(4-t-butylphenyl)-4H-3,1-benzoxazin-4-one (55 g, 98%) was prepared from 4-nitroanthanillic acid and 4-t-butylbenzoyl chloride.

$^1$H-NMR

FD-MS, m/e (M$^+$)

B) 2-[(4-t-Butylbenzoyl)amino]-N-(6-indazolyl)-4-nitrobenzamide

By methods substantially equivalent to those described in Example 24-B, 2-[(4-t-butylbenzoyl)amino]-N-(6-indazolyl)-4-nitrobenzamide (824 mg, 45%) was prepared from 6-aminoindazole and 7-nitro-2-(4-t-butylphenyl)-4H-3,1-benzoxazin-4-one.

$^1$H-NMR

FD-MS, m/e (M$^+$)

Analysis for C$_{25}$H$_{23}$N$_5$O$_4$: Calc: C, 65.64; H, 5.07; N, 15.31; Found: C, 65.67; H, 5.12; N, 15.03.

C) N-(1-Boc-6-indazolyl)-2-[(4-t-butylbenzoyl)amino]-4-nitrobenzamide

By methods substantially equivalent to those described in Example 24-C, N-(1-Boc-6-indazolyl)-2-[(4-t-butylbenzoyl)amino]-4-nitrobenzamide (910 mg, 78%) was prepared from 2-[(4-t-butylbenzoyl)amino]-N-(6-indazolyl)-4-nitrobenzamide.

$^1$H-NMR

FD-MS, m/e (M$^+$)

Analysis for C$_{30}$H$_{31}$N$_5$O$_6$: Calc: C, 64.62; H, 5.60; N, 12.56; Found: C, 64.55; H, 5.42; N, 12.44.

D) 4-Amino-N-(1-Boc-6-indazolyl)-2-[(4-t-butylbenzoyl)amino]benzamide

By methods substantially equivalent to those described in Example 2-B, 4-amino-N-(1-Boc-6-indazolyl)-2-[(4-t-butylbenzoyl)amino]benzamide (170 mg, 20%) was prepared from N-(1-Boc-6-indazolyl)-2-[(4-t-butylbenzoyl)amino]-4-nitrobenzamide.

$^1$H-NMR

FD-MS, m/e (M$^+$)

Analysis for C$_{30}$H$_{33}$N$_5$O$_4$: Calc: C, 68.29; H, 6.30; N, 13.27; Found: C, 68.18; H, 6.37; N, 13.25.

E) N-(1-Boc-6-indazolyl)-2-[(4-t-butylbenzoyl)amino]-4-[(methylsulfonyl)amino]benzamide By methods substantially equivalent to those described in Example 24-E, N-(1-Boc-6-indazolyl)-2-[(4-t-butylbenzoyl)amino]-4-[(methylsulfonyl)amino]benzamide (130 mg, 26%) was prepared from 4-amino-N-(1-Boc-6-indazolyl)-2-[(4-t-butylbenzoyl)amino]benzamide.

$^1$H-NMR

FD-MS, m/e 605.3 (M$^+$)

Analysis for C$_{31}$H$_{35}$N$_5$O$_6$S: Calc: C, 61.47; H, 5.82; N, 11.56; Found: C, 61.22; H, 5.81; N, 11.30.

F) 2-[(4-t-Butylbenzoyl)amino]-N-(6-indazolyl)-4-[(methylsulfonyl)amino]benzamide By methods substantially equivalent to those described in Example 1-F, 2-[(4-t-butylbenzoyl)amino]-N-(6-indazolyl)-4-[(methylsulfonyl)amino]benzamide (79 mg, 71%) was prepared from N-(1-Boc-6-indazolyl)-2-[(4-t-butylbenzoyl)amino]-4-[(methylsulfonyl)amino]benzamide.

$^1$H-NMR

FD-MS, m/e 505.0 (M$^+$)

Analysis for $C_{26}H_{27}N_5O_4S.0.3TFA.0.2 H_2O$: Calc: C, 59.01; H, 4.84; N, 12.47; F, 2.26; Found: C, 58.80; H, 5.14; N, 12.88; F, 3.15.

EXAMPLE 26

Preparation of 5-Amino-2-[(4-t-butylbenzoyl)amino]-N-(6-indazolyl)benzamide

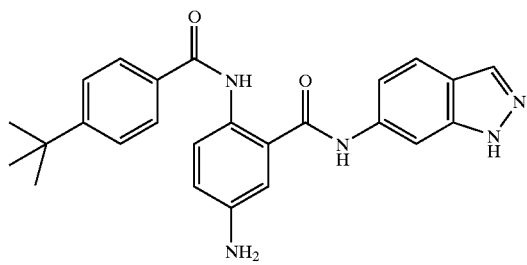

As a biproduct in the synthesis of Example 24-D, 5-amino-2-[(4-t-butylbenzoyl)amino]-N-(6-indazolyl)benzamide (130 mg, 41%) was isolated.

$^1$H-NMR

FD-MS, m/e 427.2 (M$^+$)

Analysis for $C_{25}H_{25}N_5O_2$: Calc: C, 70.23; H, 5.89; N, 16.38; Found: C, 70.45; H, 6.09; N, 16.25.

EXAMPLE 27

Preparation of 4-Amino-2-[(4-t-butylbenzoyl)amino]-N-(6-indazolyl)benzamide

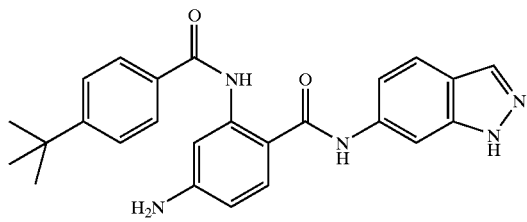

As a biproduct in the synthesis of Example 25-D, 4-amino-2-[(4-t-butylbenzoyl)amino]-N-(6-indazolyl)benzamide (350 mg, 51%) was isolated.

$^1$H-NMR

FD-MS, m/e (M$^+$)

Analysis for $C_{25}H_{25}N_5O_2$: Calc: C, 70.24; H, 5.89; N, 16.38; Found: C, 70.37; H, 5.99; N, 16.30.

EXAMPLE 28

Preparation of 2-[(4-t-Butylbenzoyl)amino]-N-(6-indolyl)-5-[(methylsulfonyl)amino]benzamide

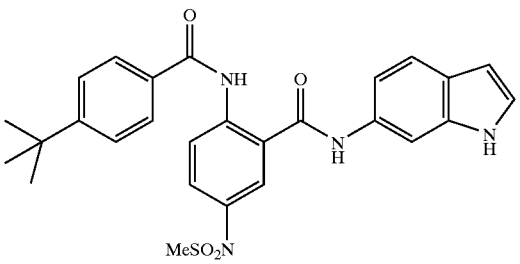

A) 2-[(4-t-Butylbenzoyl)amino]-N-(6-indolyl)-5-nitrobenzamide

By methods substantially equivalent to those described in Example 24-B, 2-[(4-t-butylbenzoyl)amino]-N-(6-indolyl)-5-nitrobenzamide (74%) was prepared from 6-aminoindole and 6-nitro-2-[4-t-butylphenyl]-4H-3,1-benzoxazin-4-one.

$^1$H-NMR

FD-MS, m/e 456 (M$^+$)

Analysis for $C_{26}H_{24}N_4O_4$: Calc: C, 68.41; H, 5.30; N, 12.27; Found: C, 68.67; H, 5.40; N, 12.28.

B) N-(1-Boc-6-indolyl)-2-[(4-t-butylbenzoyl)amino]-5-nitrobenzamide

By methods substantially equivalent to those described in Example 24-C, N-(1-Boc-6-indolyl)-2-[(4-t-butylbenzoyl)amino]-5-nitrobenzamide (72%) was prepared from 2-[(4-t-butylbenzoyl)amino]-N-(6-indolyl)-5-nitrobenzamide.

$^1$H-NMR

FD-MS, m/e 555.6 (M$^+$)

Analysis for $C_{31}H_{32}N_4O_6$: Calc: C, 66.89; H, 5.79; N, 10.06; Found: C, 67.06; H, 5.91; N, 9.96.

C) 5-Amino-N-(1-Boc-6-indolyl)-2-[(4-t-butylbenzoyl)amino]benzamide

By methods substantially equivalent to those described in Example 2-B, 5-amino-N-(1-Boc-6-indolyl)-2-[(4-t-butylbenzoyl)amino]benzamide (100%) was prepared from N-(1-Boc-6-indolyl)-2-[(4-t-butylbenzoyl)amino]-5-nitrobenzamide.

$^1$H-NMR

FD-MS, m/e 526.0 (M$^+$)

Analysis for $C_{31}H_{34}N_4O_4.0.5EtOAc.0.5H_2O$: Calc: C, 68.37; H, 6.78; N, 9.66; Found: C, 68.01; H, 6.66; N, 9.69.

D) N-(1-Boc-6-indolyl)-2-[(4-t-butylbenzoyl)amino]-5-[(methylsulfonyl)amino]benzamide By methods substantially equivalent to those described in Example 24-E, N-(1-Boc-6-indolyl)-2-[(4-t-butylbenzoyl)amino]-5-[(methylsulfonyl)amino]benzamide (40%) was prepared from 5-amino-N-(1-Boc-6-indolyl)-2-[(4-t-butylbenzoyl)amino]benzamide.

$^1$H-NMR

FD-MS, m/e 604 (M$^+$)

E) 2-[(4-t-Butylbenzoyl)amino]-N-(6-indolyl)-5-[(methylsulfonyl)amino]benzamide

By methods substantially equivalent to those described in Example 2-F, 2-[(4-t-butylbenzoyl)amino]-N-(6-indolyl)-5-[(methylsulfonyl)amino]benzamide (80%) was prepared from N-(1-Boc-6-indolyl)-2-[(4-t-butylbenzoyl)amino]-5-[(methylsulfonyl)amino]benzamide.

$^1$H-NMR

FD-MS, m/e 504 (M$^+$)

Analysis for $C_{27}H_{28}N_4O_4S$: Calc: C, 64.27; H, 5.59; N, 11.10; Found: C, 64.29; H, 5.58; N, 10.94.

EXAMPLE 29

Preparation of 2-[(4-t-Butylbenzoyl)amino]-N-(6-indolyl)-5-[bis(methylsulfonyl)amino]benzamide

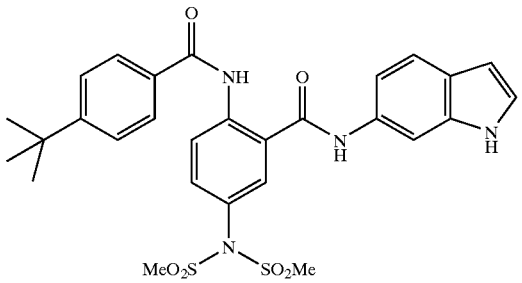

A) 2-[(4-t-Butylbenzoyl)amino]-N-(1-Boc-6-indolyl)-5-[bis(methylsulfonyl)amino]benzamide By methods susbtantially equivalent to those described in Example 24-E, using triethylamine in place of pyridine, 2-[(4-t-butylbenzoyl)amino]-N-(1-Boc-6-indolyl)-5-[bis(methylsulfonyl)amino]benzamide (16%) was prepared from 5-amino-N-(1-Boc-6-indolyl)-2-[(4-t-butylbenzoyl)amino]benzamide.

$^1$H-NMR

FD-MS, m/e 682 (M$^+$)

Analysis for $C_{33}H_{38}N_4O_8S_2 \cdot 0.10H_2O$: Calc: C, 57.89; H, 5.62; N, 8.18; Found: C, 57.84; H, 5.82; N, 8.02.

B) 2-[(4-t-Butylbenzoyl)amino]-N-(6-indolyl)-5-[bis(methylsulfonyl)amino]benzamide By methods substantially equivalent to those described in Example 2-F, 2-[(4-t-butylbenzoyl)amino]-N-(6-indolyl)-5-[bis(methylsulfonyl)amino]benzamide (100%) was prepared from 2-[(4-t-butylbenzoyl)amino]-N-(1-Boc-6-indolyl)-5-[bis(methylsulfonyl)amino]benzamide.

$^1$H-NMR

FD-MS, m/e 582.1 (M$^+$)

Analysis for $C_{28}H_{30}N_4O_6S_2$: Calc: C, 57.72; H, 5.19; N, 9.62; Found: C, 57.49; H, 5.30; N, 9.56.

EXAMPLE 30

Preparation of 2-[(4-t-Butylbenzoyl)amino]-N-(6-indolyl)-4-[(methylsulfonyl)amino]benzamide

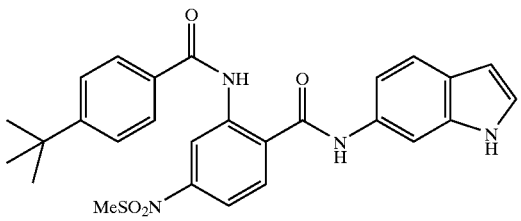

A) 2-[(4-t-Butylbenzoyl)amino]-N-(6-indolyl)-4-nitrobenzamide

By methods substantially equivalent to those described in Example 24-B, 2-[(4-t-butylbenzoyl)amino]-N-(6-indolyl)-4-nitrobenzamide (81%) was prepared from 7-nitro-2-(4-t-butylphenyl)-4H-3,1-benzoxazin-4-one.

$^1$H-NMR

FD-MS, m/e 456 (M$^+$)

B) N-(1-Boc-6-indolyl)-2-[(4-t-butylbenzoyl)amino]-4-nitrobenzamide

By methods substantially equivalent to those described in Example 24-C, N-(1-Boc-6-indolyl)-2-[(4-t-butylbenzoyl)amino]-4-nitrobenzamide (49%) was prepared from 2-[(4-t-butylbenzoyl)amino]-N-(6-indolyl)-4-nitrobenzamide.

$^1$H-NMR

FD-MS, m/e 555.9 (M$^+$)

Analysis for $C_{31}H_{32}N_4O_6 \cdot 0.25H_2O$: Calc: C, 66.36; H, 5.84; N, 9.98; Found: C, 66.04; H, 5.77; N, 9.63.

C) 4-Amino-N-(1-Boc-6-indolyl)-2-[(4-t-butylbenzoyl)amino]benzamide

By methods substantially equivalent to those described in Example 2-B, 4-amino-N-(1-Boc-6-indolyl)-2-[(4-t-butylbenzoyl)amino]benzamide (93%) was prepared from N-(1-Boc-6-indolyl)-2-[(4-t-butylbenzoyl)amino]-4-nitrobenzamide.

$^1$H-NMR

FD-MS, m/e 526.0 (M$^+$)

Analysis for $C_{31}H_{34}N_4O_4 \cdot 0.5H_2O$: Calc: C, 69.51; H, 6.59; N, 10.46; Found: C, 69.37; H, 6.71; N, 10.17.

D) N-(1-Boc-6-indolyl)-2-[(4-t-butylbenzoyl)amino]-4-[(methylsulfonyl)amino]benzamide By methods substantially equivalent to those described in Example 24-E, N-(1-Boc-6-indolyl)-2-[(4-t-butylbenzoyl)amino]-4-[(methylsulfonyl)amino]benzamide (66%) was prepared from 4-amino-N-(1-Boc-6-indolyl)-2-[(4-t-butylbenzoyl)amino]benzamide.

$^1$H-NMR

FD-MS, m/e 604.2 (M$^+$)

Analysis for $C_{32}H_{36}N_4O_6S$: Calc: C, 62.94; H, 6.21; N, 8.64; Found: C, 62.99; H, 5.93; N, 8.79.

E) 2-[(4-t-Butylbenzoyl)amino]-N-(6-indolyl)-4-[(methylsulfonyl)amino]benzamide

By methods substantially equivalent to those described in Example 2-F, 2-[(4-t-butylbenzoyl)amino]-N-(6-indolyl)-4-[(methylsulfonyl)amino]benzamide (93%) was prepared from N-(1-Boc-6-indolyl)-2-[(4-t-butylbenzoyl)amino]-4-[(methylsulfonyl)amino]benzamide.

$^1$H-NMR

FD-MS, m/e 504.0 (M$^+$)

Analysis for $C_{27}H_{28}N_4O_4S$: Calc: C, 64.27; H, 5.59; N, 11.10; Found: C, 64.37; H, 5.48; N, 10.91.

EXAMPLE 31

Preparation of 2-[(4-t-Butylbenzoyl)amino]-N-(6-indolyl)-4-[bis(methylsulfonyl)amino]benzamide

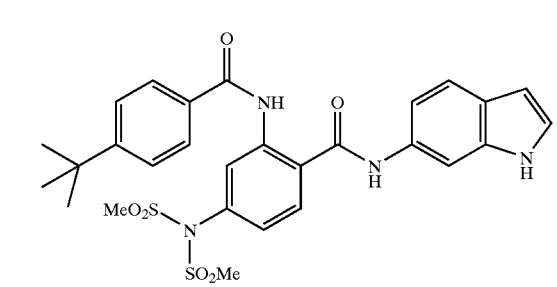

A) 2-[(4-t-Butylbenzoyl)amino]-N-(1-Boc-6-indolyl)-4-[bis(methylsulfonyl)amino]benzamide By methods substantially equivalent to those described in Example 29-A, 2-[(4-t-butylbenzoyl)amino]-N-(1-Boc-6-indolyl)-4-[bis(methylsulfonyl)amino]benzamide (33%) was prepared from N-(1-Boc-6-indolyl)-2-[(4-t-butylbenzoyl)amino]-4-aminobenzamide.

$^1$H-NMR

FD-MS, m/e 682.6 (M$^+$)

B) 2-[(4-t-Butylbenzoyl)amino]-N-(6-indolyl)-4-[bis(methylsulfonyl)amino]benzamide By methods substantially equivalent to those described in Example 2-F, 2-[(4-t-butylbenzoyl)amino]-N-(6-indolyl)-4-[bis(methylsulfonyl)amino]benzamide (85%) was prepared from 2-[(4-t-butylbenzoyl)amino]-N-(1-Boc-6-indolyl)-4-[bis(methylsulfonyl)amino]benzamide.

$^1$H-NMR

FD-MS, m/e 582.1 (M$^+$)

Analysis for $C_{28}H_{30}N_4O_6S_2$: Calc: C, 57.72; H, 5.19; N, 9.61; Found: C, 57.62; H, 5.22; N, 9.46.

EXAMPLE 32

Preparation of 4-Hydroxy-N$^1$-(6-indolylcarbonyl)-N$^2$-[1-(4-pyridyl)piperidin-4-yl]methoxycarbonyl-1,2-benzenediamine and hydrochloride hydrate

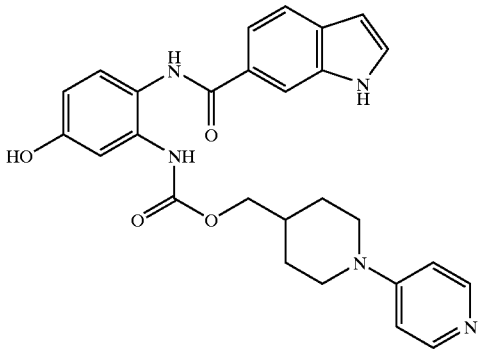

A) 4-(tert-butyldimethylsilyloxy)-2-nitroaniline

To a mixture of 4-amino-3-nitrophenol (10.07 g, 65.3 mmol) and DMF (20 mL) was added imidazole (11.15 g, 163.8 mmol) followed by t-butyldimethylsilyl chloride (11.82 g, 78.4 mmol) in several portions. After 5 h, the reaction was diluted with EtOAc (150 mL) and washed with water (5×20 mL). The organic layer was MgSO$_4$, dried, filtered, and concentrated. The residue was chromatographed (10% EtOAc/hexanes to 20% EtOAc/hexanes) to give the title compound as a solid (17.06 g, 97%); mp 80–83° C.; IR (CHCl$_3$): 3399, 2932, 1519, 1242, 866 cm$^{-1}$; NMR (300 MHz, CDCl$_3$): δ0.19 (s, 6H), 0.97 (s, 9H), 6.70 (d, 1H, J=9.0), 6.95 (d, 1H, J=3.0), 7.56 (d, 1H, J=2.7); MS(FD): 268.2.

Analysis for $C_{12}H_{20}N_2O_3Si$: Calc: C 53.70, H 7.51, N 10.44; Found: C 53.47, H 7.50, N 10.31.

B) 5-(tert-butyldimethylsilyloxy)-2-phthalimido-1-nitrobenzene

A mixture of 2-nitro-4-(tert-butyldimethylsilyloxy)aniline (10.3 g, 38.5 mmol) and phthalic anhydride (6.50 g, 41.5 mmol) in toluene (30 mL) was refluxed for 18 h. A Dean-Stark apparatus was fitted to the flask, diisopropylethylamine (0.1 mL) was added and water was removed azeotropically over the next 24 h. About 20 mL of solvent was removed by distillation and the resultant solution allowed to cool to room temperature. The residue was diluted with methylene chloride and passed through a plug of silica gel eluting with methylene chloride. The desired fractions were combined and concentrated in vacuo. Recrystallization from methylene chloride-hexane provided 12.2 g (80%) of the title compound in two crops.

Analysis for $C_{20}H_{22}N_2O_5Si$: Calc: C, 60.28; H, 5.56; N, 7.03; Found: C, 60.35; H, 5.67; N, 6.98.

C) 5-(tert-butyldimethylsilyloxy)-2-phthalimidoaniline

A suspension of 5-(tert-butyldimethylsilyloxy)-2-phthalimido-1-nitrobenzene (5.00 g, 12.5 mmol) and 10% palladium-on-carbon (2.5 g) in ethyl acetate (60 mL) was stirred under 1 atm of hydrogen for 16 h. The mixture was filtered through a pad of diatomaceous earth and concentrated in vacuo to yield 4.1 g (89%) of the title compound.

D) 5-(tert-butyldimethylsilyloxy)-2-phthalimido-N-[[1-(4-pyridyl)piperidin-4-yl]methoxycarbonyl]aniline A solution of 5-(tert-butyldimethylsilyloxy)-2-phthalimidoaniline (1.02 g, 2.77 mmol) in toluene (15 mL) was treated with a solution of 20% phosgene in toluene (2 mL) at reflux for 20 min. The volatile materials were removed in vacuo to give a tan solid, which was dissolved in dry methylene chloride (20 mL) and treated with 1-(4-pyridyl)piperidine-4-methanol (0.53 g, 2.77 mmol). The resulting suspension was stirred for 90 min then diluted with hexane. The mixture was allowed to stand overnight and the resulting precipitate collected by vacuum filtration and dried to yield 1.46 g (90%) of the title compound as a tan powder.

MS-FD, m/e 587 (M).

Analysis for $C_{32}H_{38}N_4O_5Si$: Calc: C, 65.50; H, 6.53; N, 9.55; Found: C, 65.23; H, 6.47; N, 9.38.

E) 4-(tert-butyldimethylsilyloxy)-N$^2$-[1-(4-pyridyl)-piperidin-4-yl]methoxycarbonyl-1,2-benzenediamine A solution of 5-(tert-butyldimethylsilyloxy)-2-phthalimido-N-[[1-(4-pyridyl)piperidin-4-yl]methoxycarbonyl]aniline (1.34 g, 2.28 mmol) in 1 M hydrazine in methanol (6 mL) was stirred at ambient temperature for 40 h during which time a white precipitate formed. The mixture was further diluted with methylene chloride and cooled with an ice bath then filtered. The filtrate was washed once with saturated sodium chloride solution, dried over anhydrous sodium sulfate, filtered, and concentrated in vacuo to yield 890 mg (86%) of the title compound as a tan powder.

MS-FD, m/e 456 (M).

F) 4-(tert-butyldimethylsilyloxy)-N$^1$-(6-indolylcarbonyl)-N$^2$-[1-(4-pyridyl)piperidin-4-yl]methoxycarbonyl-1,2-benzenediamine A mixture of indole-6-carboxylic acid (71 mg, 0.44 mmol), bromotris(pyrrolidino)phosphonium hexafluorophosphate (204 mg, 0.44 mmol) and diisopropylethylamine (0.153 mL, 0.88 mmol) in dry methylene chloride (5 mL) was stirred 10 min. 4-(tert-Butyldimethylsilyloxy)-N$^2$-[1-(4-pyridyl)piperidin-4-yl]methoxycarbonyl-1,2-benzenediamine (100 mg, 0.22 mmol) and N,N-dimethylformamide (2 mL) were added and the resulting mixture stirred 64 h at ambient temperature. Saturated aqueous sodium hydrogen carbonate solution (4 mL) was added, and the resultant mixture stirred for 30 min. The mixture was partitioned between ethyl acetate and water, the organic solution separated, dried (anhydrous magnesium sulfate), filtered, and concentrated in vacuo. The residue was chromatographed (silica gel, methylene chloride, 9:1 methylene chloride/methanol, 9:1:0.1 methylene chloride/methanol/ammonium hydroxide) to yield 55 mg (44%) of the title compound.

G-1) 4-Hydroxy-N$^1$-(6-indolylcarbonyl)-N$^2$-[1-(4-pyridyl)-piperidin-4-yl]methoxycarbonyl-1,2-benzenediamine A solution of 4-(tert-butyldimethylsilyloxy)-N$^1$-(6-indolylcarbonyl)-N$^2$-[1-(4-pyridyl)piperidin-4-yl]methoxycarbonyl-1,2-benzenediamine (55 mg, 0.096 mmol) in tetrahydrofuran (2 mL) was treated with 5 N aqueous hydrochloric acid (0.5 mL) and allowed to stand at ambient temperature overnight. Volatile solvents were removed in vacuo and the residue diluted with dilute sodium hydrogen carbonate solution, hexane, and methylene chloride. The mixture was sonicated 5 min, then filtered. The resultant material was vacuum dried 6 h to yield 37 mg (79%) of the title compound as a tan solid.

MS-FD, m/e 486 (M), 309, 155, 119 (base).

An alternative preparation of the hydrochloride hydrate is as follows.

G-2) 4-Hydroxy-$N^1$-(6-indolylcarbonyl)-$N^2$-[1-(4-pyridyl)-piperidin-4-yl]methoxycarbonyl-1,2-benzenediamine hydrochloride hydrate A solution of 4-(tert-butyldimethylsilyloxy)-$N^1$-(6-indolylcarbonyl)-$N^2$-[1-(4-pyridyl)piperidin-4-yl]methoxycarbonyl-1,2-benzenediamine (682 mg,1.20 mmol) in 10 mL tetrahydrofuran was treated with 2.5 mL 5 N HCl and allowed to stand at ambient temperature over night. Volatile solvents were removed in vacuo and the residue neutralized with sodium hydrogen carbonate solution. The mixture was triturated with hexane over 30 min then the solid collected by filtration. The solid was purified by reverse phase HPLC (5 cm×25 cm Vydac C18, 10 mL/min, λ=214 nm, 2–40% B. Solvent A: 0.01% HCl. Solvent B: 100% AcCN.) Lyophilization of the appropriate fractions yielded 272 mg (46.8%) of the hydrated HCl salt as a powder. MS, Ion spray, m/e: 486 (p+1).

Analysis for $C_{27}H_{27}N_5O_4 \cdot HCl \cdot H_2O$: Calc.: C, 60.06; H, 5.60; N, 12.97; Found: C, 60.26; H, 5.23; N, 13.23.

EXAMPLE 33

Preparation of 4-Hydroxy-$N^2$-(4-t-butylbenzoyl)-$N^1$-(6-indolylcarbonyl)-1,2-benzenediamine

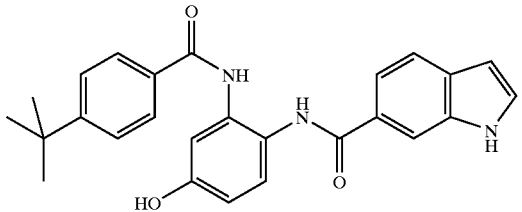

A) 4-t-Butyldimethylsilyloxy-$N^2$-(4-t-butylbenzoyl)-$N^1$-(6-indolylcarbonyl)-1,2-benzenediamine Using the procedure described in Example 9, Part C, 4-t-butyldimethylsilyloxy-$N^2$-(4-t-butylbenzoyl)-1,2-benzenediamine (1.15 g, 2.9 mmol) and indole-6-carboxylic acid (0.46 g, 2.9 mmol) yielded 780 mg (50%) of the title compound.

$^1$H-NMR

FD-MS, m/e 541.2 (M+)

Analysis for $C_{32}H_{39}N_3O_3Si$: Calc: C, 70.94; H, 7.26; N, 7.76; Found: C, 70.93; H, 7.13; N, 7.75.

B) 4-Hydroxy-$N^2$-(4-t-butylbenzoyl)-$N^1$-(6-indolylcarbonyl)-1,2-benzenediamine To a stirring solution of 4-t-butyldimtheylsilyloxy-$N^2$-(4-t-butylbenzoyl)-$N^1$-(6-indolylcarbonyl)-1,2-benzenediamine (680 mg, 1.26 mmol) in THF (10 mL) was added a 1.0 M solution of tetrabutylammonium fluoride in THF (1.3 mL, 1.3 mmol). After 15 min, the solution was poured into ethyl acetate (300 mL) and washed once with water, twice with 1 M citric acid, once again with water, twice with satd aq sodium bicarbonate, and once with brine. After drying with MgSO$_4$, the organic phase was filtered, silica gel (3 g) was added, and the mixture was concentrated in vacuo. The resulting powder was loaded onto a silica gel column which was preequilibrated with 25% ethyl acetate/dichloromethane and was eluted with a gradient of 25% ethyl acetate/dichloromethane through 50% ethyl acetate/dichloromethane. The product containing fractions were combined and concentrated in vacuo to give a thick oil which was dissolved in diethyl ether, sonicated, and concentrated in vacuo to give the title compound as a white solid (480 mg, 88%).

$^1$H-NMR

FD-MS, m/e 427.3 (M+)

Analysis for $C_{26}H_{25}N_3O_3$: Calc: C, 73.05; H, 5.89; N, 9.83; Found: C, 73.02; H, 5.78; N, 9.60.

EXAMPLE 34

Preparation of 4-Hydroxy-$N^2$-(4-t-butylbenzoyl)-$N^1$-(3-chloroindol-6-ylcarbonyl)-1,2-benzenediamine

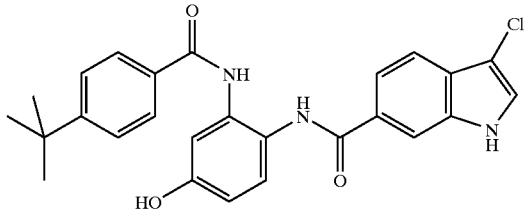

A) 3-Chloroindole-6-carboxylic acid

To a solution of indole-6-carboxylic acid (2.45 g, 15.2 mmol) in dichloromethane (100 mL) and DMF (10 mL) was added N-chlorosuccinimide (2 g, 15.2 mmol). After 3 h, the solvent was removed in vacuo and the residue was suspended in dichloromethane, sonicated and filtered to give 2.38 g (80%) of the title compound.

$^1$H-NMR

FD-MS, m/e 195.604 (M+)

Analysis for $C_9H_6ClNO_2$: Calc: C, 55.26; H, 3.09; N, 7.16; Found: C, 55.18; H, 3.10; N, 7.05.

B) 4-t-Butyldimethylsilyloxy-$N^2$-(4-t-butylbenzoyl)-$N^1$-(3-chloroindol-6-ylcarbonyl)-1,2-benzenediamine Using the procedure described in Example 9, Part C, 4-t-butyldimethylsilyloxy-$N^2$-(4-t-butylbenzoyl)-1,2-benzenediamine (750 mg, 1.9 mmol) and 3-chloroindole-6-carboxylic acid (372 mg, 1.9 mmol) yielded 790 mg (72%) of the title compound.

$^1$H-NMR

FD-MS, m/e 575.1 (M+)

Analysis for $C_{32}H_{38}ClN_3O_3Si$: Calc: C, 66.70; H, 6.65; N, 7.29; Found: C, 66.60; H, 6.63; N, 7.22.

C) 4-Hydroxy-$N^2$-(4-t-butylbenzoyl)-$N^1$-(3-chloroindol-6-ylcarbonyl)-1,2-benzenediamine Using the procedure described in Example 33, Part B, 4-t-butyldimethylsilyloxy-$N^2$-(4-t-butylbenzoyl)-$N^1$-(3-chloroindol-6-ylcarbonyl)-1,2-benzenediamine(760 mg, 1.3 mmol) yielded 520 mg (87%) of the title compound.

$^1$H-NMR

FD-MS, m/e 461.1 (M+)

Analysis for $C_{26}H_{24}ClN_3O_3$: Calc: C, 67.60; H, 5.24; N, 9.10; Found: C, 67.42; H, 5.39; N, 9.04.

EXAMPLE 35

Preparation of 4-Hydroxy-$N^2$-(4-t-butylbenzoyl)-$N^1$-(3-bromoindol-6-ylcarbonyl)-1,2-benzenediamine

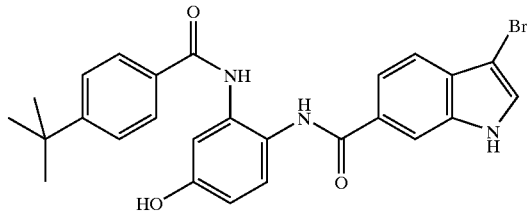

A) 3-Bromoindole-6-carboxylic acid

Using the procedure described in Example 34, Part A, indole-6-carboxylic acid (2.6 g, 16.1 mmol) and N-bromosuccinimide (2.9 g, 16.1 mmol) yielded 2.88 g (75%) of the title compound.

$^1$H-NMR
FD-MS, m/e 239.0 (M+)
Analysis for $C_9H_6BrNO_2$: Calc: C, 45.03; H, 2.52; N, 5.83; Found: C, 45.19; H, 2.46; N, 5.87.

B) 4-t-Butyldimethylsilyloxy-$N^2$-(4-t-butylbenzoyl)-$N^1$-(3-bromoindol-6-ylcarbonyl)-1,2-benzenediamine Using the procedure described in Example 9, Part C, 4-t-butyldimethylsilyloxy-$N^2$-(4-t-butylbenzoyl)-1,2-benzenediamine (750 mg, 1.9 mmol) and 3-bromoindole-6-carboxylic acid (456 mg, 1.9 mmol) yielded 930 mg (79%) of the title compound.

$^1$H-NMR
FD-MS, m/e 621.1 (M+)
Analysis for $C_{32}H_{38}BrN_3O_3Si$: Calc: C, 61.93; H, 6.17; N, 6.77; Found: C, 62.09; H, 6.15; N, 6.83.

C) 4-Hydroxy-$N^2$-(4-t-butylbenzoyl)-$N^1$-(3-bromoindol-6-ylcarbonyl)-1,2-benzenediamine Using the procedure described in Example 33, Part B, 4-t-butyldimethylsilyloxy-$N^2$-(4-t-butylbenzoyl)-$N^1$-(3-bromoindol-6-ylcarbonyl)-1,2-benzenediamine (850 mg, 1.37 mmol) yielded 450 mg (65%) of the title compound.

$^1$H-NMR
FD-MS, m/e 504.9 (M+)
Analysis for $C_{26}H_{24}BrN_3O_3$: Calc: C, 61.67; H, 4.78; N, 8.30; Found: C, 61.92; H, 4.92; N, 8.13.

EXAMPLE 36

Preparation of $N^1$-(3-Chloroindol-6-ylcarbonyl)-$N^2$-[1-(4-pyridyl)piperidin-4-yl]methoxycarbonyl-1,2-benzenediamine

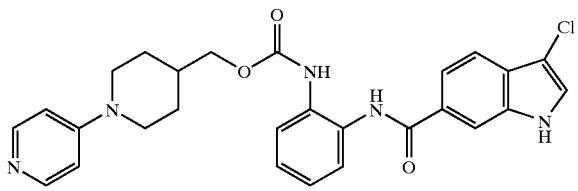

Using the procedure described in Example 23, Part C, and purifying with preparative RPHPLC method A, $N^2$-[1-(4-pyridyl)piperidin-4-yl]methoxycarbonyl-1,2-benzenediamine (326 mg, 1.0 mmol) and 3-chloroindole-6-carboxylic acid (195 mg, 1.0 mmol) yielded the title compound.

FIA-MS, m/e 504.0 (MH+)

EXAMPLE 37

Preparation of $N^1$-(3-Bromoindol-6-ylcarbonyl)-$N^2$-[1-(4-pyridyl)piperidin-4-yl]methoxycarbonyl-1,2-benzenediamine

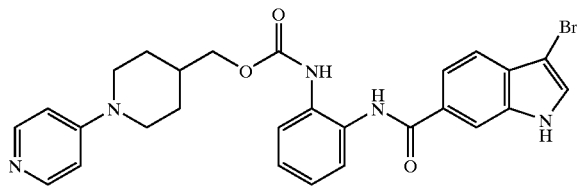

Using the procedure described in Example 23, Part C, and purifying with preparative RPHPLC method A, $N^2$-[1-(4-Pyridyl)-piperidin-4-yl]methoxycarbonyl-1,2-benzenediamine(326 mg, 1.0 mmol) and 3-bromoindole-6-carboxylic acid (240 mg, 1.0 mmol) yielded the title compound.

FIA-MS, m/e 550.0 (MH+)

EXAMPLE 38

Preparation of N-(6-Indazolyl)-2-[1-(4-pyridyl)-piperidin-4-ylcarbonyl]aminobenzamide hydrochloride

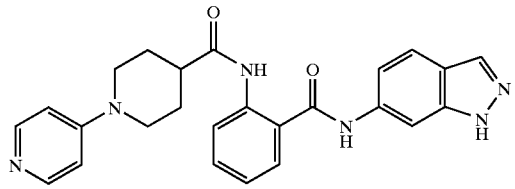

A) 2-[1-(4-Pyridyl)piperidin-4-ylcarbonyl]amino-N-(1-Boc-indazol-6-yl)benzamide

To a stirring suspension of 1-(4-pyridyl)piperidinecarboxylic acid (350 mg, 1.70 mmol) in dichloromethane (50 mL) at reflux was added thionyl chloride (0.190 mL, 2.55 mmol). After 4 h, the solvent was removed in vacuo and the residue was redissolved in dichloromethane (20 mL) and added to a stirring solution of 2-amino-N-(1-Boc-6-indazolyl)benzamide (300 mg, 0.85 mmol) in pyridine (5 mL) and dichloromethane (20 mL). After 30 min, the solvent was removed in vacuo; and the residue was partitioned between ethyl acetate (300 mL) and 1 N NaOH (150 mL). The layers were separated and the organic phase was washed with brine, dried with $MgSO_4$, filtered and concentrated in vacuo. The solid was supsended in diethyl ether, sonicated and filtered to give 455 mg (99%) of the title compound.

$^1$H-NMR
FD-MS, m/e 541(M+)
Analysis for $C_{30}H_{32}N_6O_4$: Calc: C, 66.65; H, 5.97; N, 15.55; Found: C, 65.58; H, 6.15; N, 15.04.

B) 2-[1-(4-Pyridyl)piperidin-4-ylcarbonyl]amino-N-(6-indazolyl)benzamide hydrochloride Using the procedure described in Example 1, Part F, purifying with preparative RPHPLC method B, 2-[1-(4-pyridyl)piperidin-4-ylcarbonyl]amino-N-(1-Boc-indazol-6-yl)benzamide (455 mg, 0.84 mmol) yielded 110 mg (28%) of the title compound.

¹H-NMR

FIA-MS, m/e 441.0 (M+)

Analysis for $C_{25}H_{24}N_6O_2 \cdot 1.0HCl \cdot 1.1H_2O$: Calc: C, 60.45; H, 5.52; N, 16.91; Cl, 7.14; Found: C, 60.23; H, 5.13; N, 16.76; Cl, 7.20.

EXAMPLE 39

Preparation of $N^4$-Acetyl-$N^2$-(4-t-butylbenzoyl)-$N^1$-(6-indolylcarbonyl)-1,2,4-benzenetriamine

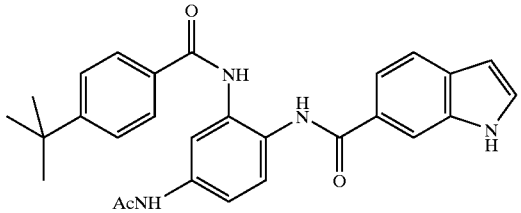

A) 2-amino-4-N-acetylamino-nitrobenzene

To a stirring solution of 2,4-diaminonitrobenzene (5 g, 33 mmol) and pyridine (5.25 mL, 66 mmol) in THF (30 mL) at 0° C., was added a solution of acetyl chloride (2.2 mL, 31 mmol) in THF (20 mL) via an addition funnel. The rate of the addition was controlled such that the internal temperature did not rise above 5° C. (about 30 min). The cold bath was then removed and after an additional 30 min, the solvent was removed in vacuo. The residue was dissolved in chloroform, stirred overnight, and the resulting precipitate was filtered and dried to give 4.35 g (72%) of the title compound.

¹H-NMR

FD-MS, m/e 195 (M+)

Analysis for $C_8H_9N_3O_3$: Calc: C, 49.23; H, 4.65; N, 21.53; Found: C, 49.21; H, 4.71; N, 21.61.

B) 2-(4-t-Butylbenzoyl)amino-4-N-acetylaminonitrobenzene

Using the procedure described in Example 1, Part C, 2-amino-4-N-acetylaminonitrobenzene (4 g, 21 mmol) and 4-t-butylbenzoyl chloride (4.4 mL, 23 mmol) yielded 3.6 g (49%) of the title compound.

¹H-NMR

FD-MS, m/e 355 (M+)

C) 2-(4-t-Butylbenzoyl)amino-4-N-acetylaminoaniline

Using the procedure described in Example 1, Part B, 2-(4-t-butylbenzoyl)amino-4-(acetylamino)nitrobenzene yielded 1.38 g (50%) of the title compound.

¹H-NMR

FD-MS, m/e 325.3 (M+)

Analysis for $C_{19}H_{23}N_3O_2$: Calc: C, 70.13; H, 7.12; N, 12.91; Found: C, 70.06; H, 6.89; N, 12.64.

D) $N^4$-Acetyl-$N^2$-(4-t-butylbenzoyl)-$N^1$-(6-indolylcarbonyl)-1,2,4-benzenetriamine To a stirring solution of 2-(4-t-butylbenzoyl)amino-4-(acetylamino)aniline (40 mg, 0.12 mmol), 6-indolecarboxylic acid (40 mg, 0.24 mmol) and bromotris(pyrrolidino)phosphonium hexafluorophosphate (112 mg, 0.12 mmol) in dichloromethane (10 mL) and DMF (1 mL) was added N,N-diisopropylethylamine (42 mg, 0.36 mmol). After 3 days, the solvent was removed in vacuo and the residue was dissolved in ethyl acetate and washed once with 1 N HCl, once with satd aq sodium bicarbonate, dried with MgSO₄, filtered and concentrated in vacuo. The residue was then chromatographed over silica gel, eluting with 10% methanol/dichloromethane and the product containing fractions were combined and concentrated to give 40 mg (71%) of the title compound.

¹H-NMR

FD-MS, m/e 469.2 (M+)

Analysis for $C_{28}H_{28}N_4O_3$: Calc: C, 71.78; H, 6.02; N, 11.96; Found: C, 69.22; H, 6.26; N, 11.26.

EXAMPLE 40

Preparation of $N^1$-(6-Indolylcarbonyl)-$N^2$-[1-(4-pyridyl)-piperidin-4-yl]methylaminocarbonyl-1,2-benzenediamine

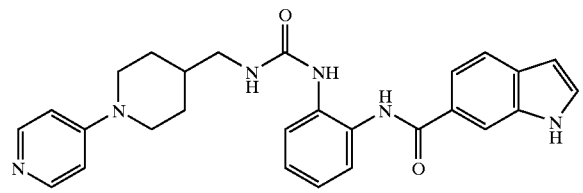

A) 1-(4-Pyridyl)piperidine-4-methylamine

A solution of 1-(4-pyridyl)piperidine-4-methanol (5.87 g, 30.6 mmol), phthalimide (4.59 g, 31.2 mmol), and triphenylphosphine (8.10 g, 30.9 mmol) in 125 mL of THF at −5° C. was treated with a solution of diethyl azodicarboxylate (5.38 g, 30.9 mmol) in THF (40 mL). After 16 h, the mixture was poured into EtOAc and 1N HCl. The aqueous layer was washed with EtOAc (2×), pH adjusted to 12 by addition of 5N NaOH, and washed with EtOAc (3×). The combined organic extracts were dried ($K_2CO_3$) and concentrated yielding 8.45 g (86%) of the substituted phthalimide. The crude material (5.47 g, 17.0 mmol) was then treated with hydrazine hydrate (3.5 mL, 60.0 mmol) in EtOH (50 mL). The mixture was heated at 75° C. for 5 h, cooled, diluted with $CH_2Cl_2$ (100 mL), and cooled to 0° C. The solid was removed by filtration and the filtrate was concentrated yielding 3.32 g of the title compound which was used without further purification.

¹H-NMR

B) 2-[1-(4-Pyridyl)piperidin-4-ylmethylaminocarbonyl]amino-nitrobenzene

A solution of 1-(4-pyridyl)piperidine-4-methylamine (1.34 g, 7.01 mmol) and 2-nitrophenyl isocyanate (1.21 g, 7.40 mmol) in methylene chloride was stirred at room temperature. Concentration in vacuo and purification by flash chromatography (silica gel, 5% methanol/1% triethylamine/94% chloroform) yielded 1.59 g (64%) of the title compound.

¹H-NMR, IR

MS-FD m/e 355 (p)

Analysis for $C_{18}H_{21}N_5O_3$: Calc: C, 60.83; H, 5.96; N, 19.71; Found: C, 60.66; H, 5.90; N, 19.50.

C) $N^1$-[1-(4-Pyridyl)piperidin-4-ylmethylaminocarbonyl)-1,2-benzenediamine

A solution of 2-[1-(4-pyridyl)piperidin-4-ylmethylaminocarbonyl]amino-nitrobenzene (1.02 g, 2.87 mmol) in ethanol was hydrogenated at atmospheric pressure over 5% palladium-on-carbon. After completion (16–20 h), the mixture was filtered through diatomaceous earth, using hot ethyl acetate to wash the filter cake. Concentration of the filtrate in vacuo yielded 930 mg (99%) of the title compound.

¹H-NMR, IR

MS-FD m/e 326 (p+1)

Analysis for $C_{18}H_{23}N_5O$: Calc: C, 66.44; H, 7.12; N, 21.52; Found: C, 65.39; H, 7.02; N, 20.76.

D) N[1]-(4-Chlorobenzoyl)-N[2]-[1-(4-pyridyl)piperidin-4-yl-methylaminocarbonyl]-1,2-benzenediamine Using a similar procedure to that of Example 39, Part D, the above amine (100 mg) was coupled with 6-indole-carboxylic acid (98 mg) using bromotris(pyrrolidino) phosphonium hexafluorophosphate (289 mg) and N,N-diisopropylethylamine (120 mg) in dichloromethane (5 mL). Following the initial chromatography, the product was further purified by RPHPLC [similar to Method B, but 90/10 (A/B) through 50/50 (A/B)] to provide the title compound (50 mg, 34%).

FIA-MS, m/e 469.2 (M+1)

EXAMPLE 41

Preparation of N-(6-Indolyl)-4-(methylsulfonylamino)-2-[(1-(4-pyridyl)piperidin-4-ylmethoxycarbonyl)amino]benzamide

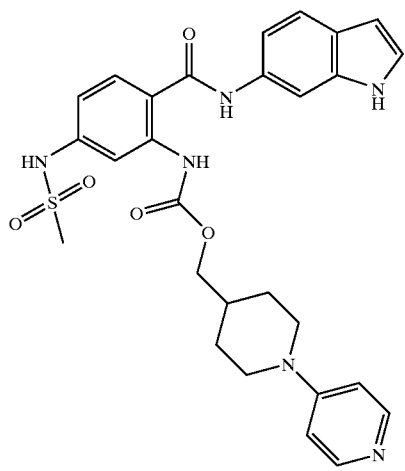

A) N-(6-indolyl)-2-amino-4-nitrobenzamide

Using the procedure described in Example 44, Part A, 4-nitroisatoic anhydride yielded 9.61 g (54%) of the title compound as a solid.

NMR

B) N-(1-tert-butoxycarbonyl-6-indolyl)-2-amino-4-nitrobenzamide

Using the procedure described in Example 1, Part A, N-(6-indolyl)-2-amino-4-nitrobenzamide yielded 3.47 g (27%) of the title compound as a solid.

NMR

C) N-(1-boc-6-indolyl)-2-[1-(4-pyridyl)piperidin-4-yl-methoxycarbonylamino]-4-nitrobenzamide

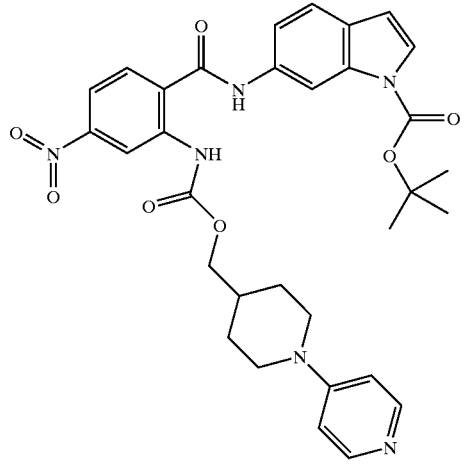

To a mixture of 1-(4-pyridyl)piperidine-4-ylmethanol (193 mg, 1.0 mmol) and methylene chloride (15 ml) was added methanesulfonic acid (65 µL, 1.0 mmol). After stirring for 15 seconds, quinoline (0.15 mL, 1.27 mmol) was added, immediately followed by 1.93 M phosgene in toluene (0.65 µL, 1.25 mmol). After 5 min, the reaction was placed in a 35° C. oil bath for 45 min. The reaction was cooled to room temperature and N-(1-boc-6-indolyl)-2-amino-4-nitrobenzamide (398 mg, 1.0 mmol) and quinoline(0.15 mL, 1.27 mmol) were added. After stirring overnight, the reaction was diluted with $CHCl_3$(75 mL) and washed with 1 N NaOH (2×10 mL) and $H_2O$ (10 mL). The organic layer was concentrated and the crude residue was chromatographed to give 101 mg (16%) of the title compound as a solid.

$^1$H-NMR (300 MHz, DMSO-$d_6$): δ10.78(s, 1H); 10.24(br s, 1H); 8.79(s, 1H); 8.75(s, 1H); 8.08(m, 2H); 8.02(s, 2H); 7.63(d, J=3.6 Hz, 1H); 7.58(d, J=8.7 Hz, 1H); 7.47(d, J=9.3 Hz, 1H); 6.74(d, J=9.0 Hz, 2H); 6.67(d, J=3.6 Hz, 1H); 4.00(d, J=6.3 Hz, 2H); 3.88(d, J=14.4 Hz, 2H); 2.76(t, J=12.0 Hz, 2H); 1.93(m, 1H); 1.70(d, J=9.9 Hz, 2H); 1.21 (m, 2H); MS-FD m/e: 615.2 (p+1).

Analysis for $C_{32}H_{34}N_6O_7$: Calc: C, 62.53; H, 5.58; N, 13.67; *Found: C, 62.68; H, 4.89; N, 15.71.

D) N-(1-Boc-6-indolyl)-2-[1-(4-pyridyl)piperidin-4-yl-methoxycarbonylamino]-4-aminobenzamide

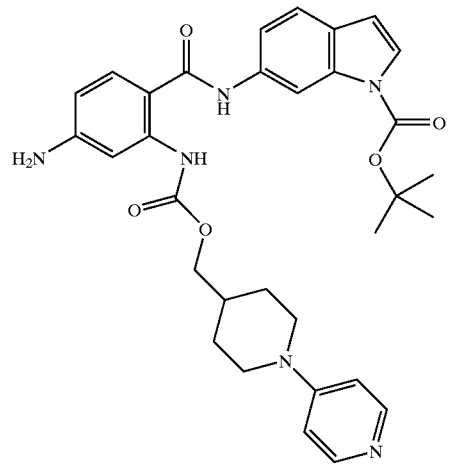

Using the procedure described in Example 2, Part B, N-(1-boc-6-indolyl)-2-[1-(4-pyridyl)piperidin-4- ylmethoxycarbonylamino]-4-nitrobenzamide (2.28 mmol) yielded 1.05 g (79%) of the title compound as a solid.

IR(KBr): 1727, 1597, 1264; $^1$H-NMR (300 MHz, DMSO-$d_6$): δ8.65(s, 1H); 8.09(d, J=5.7 Hz, 2H); 7.68(d, J=9.0 Hz, 1H); 7.58(s, 1H); 7.46(m, 2H); 6.78(m, 2H); 6.64(s, 1H); 6.24(d, J=9.0 Hz, 1H); 5.96(s, 3H); 3.94(m, 4H); 2.80(m, 2H); 1.73(m, 3H); 1.18(m, 2H); MS-FD m/e: 585.0 (p+1).

Analysis for $C_{32}H_{36}N_6O_5$: Calc: C, 65.74; H, 6.21; N, 14.37; *Found: C, 65.04; H, 5.76; N, 15.94.

E) N-(1-boc-6-indolyl)-2-[1-(4-pyridyl)piperidin-4-yl-methoxycarbonylamino]-4-(methylsulfonylamino)benzamide

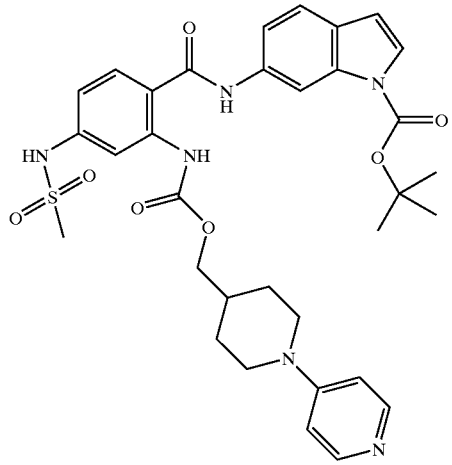

Using the procedure described in Example 24, Part E, N-(1-boc-6-indolyl)-2-[1-(4-pyridyl)piperidin-4-ylmethoxycarbonylamino]-4-aminobenzamide was reacted with methanesulfonyl chloride (0.58 mmol) to yield 143 mg (41%) of the title compound as a white solid.

$^1$H-NMR (300 MHz, DMSO-$d_6$): δ10.62(s, 1H); 10.39(s, 1H); 8.67(s, 1H); 8.07(m, 3H); 7.84(d, J=8.7 Hz, 1H); 7.60(d, J=3.6 Hz, 1H); 7.54(d, J=8.1 Hz, 1H); 7.43(d, J=8.4 Hz, 1H); 6.94(d, J=8.7 Hz, 1H); 6.80(d, J=6.3 Hz, 2H); 6.64(d, J=3.6 Hz, 1H); 3.95(m, 4H); 3.06(s, 1H); 2.82(t, J=12.5 Hz, 2H); 1.91(m, 1H); 1.72(d, J=11.7 Hz, 2H); 1.60(s, 9H); 1.19(m, 2H); MS-FD m/e: 663.1 (p+1).

Analysis for $C_{33}H_{38}N_6O_7S$: Calc: C, 59.81; H, 5.78; N, 12.68; *Found: C, 60.75; H, 6.43; N, 12.45.

F) N-(6-Indolyl)-2-[1-(4-pyridyl)piperidin-4-ylmethoxycarbonylamino]-4-(methylsulfonylamino)benzamide A sample of N-(1-boc-6-indolyl)-2-[1-(4-pyridyl)-piperidin-4-ylmethoxycarbonylamino]-4-(methylsulfonylamino)benzamide (120 mg, 0.18 mmol) was heated at 180°, until TLC indicated that the reaction had gone to completion, to yield 95 mg (94%) of the title compound as a tan solid.

IR(KBr): 1711, 1646, 1419; $^1$H-NMR (300 MHz, DMSO-$d_6$): δ11.40(s, 1H); 11.19(s, 1H); 8.08(d, J=5.7 Hz, 2H); 7.83(d, J=8.7 Hz, 1H); 7.53(d, J=8.4 Hz, 1H); 7.39(s, 1H); 7.25(s, 1H); 7.09(s, 1H); 6.95(d, J=8.4 Hz, 1H); 6.81(m, 3H); 6.45(s, 1H); 3.94(m, 4H); 3.10(s, 3H); 2.82(t, J=12.3 Hz, 2H); 1.70(m, 3H); 1.09(m, 2H); MS-FD m/e: 563.0 (p+1).

Analysis for $C_{28}H_{30}N_6O_5S$·0.5 $H_2O$: Calc: C, 58.84; H, 5.47; N, 14.70; Found: C, 58.92; H, 5.33; N, 14.45.

EXAMPLE 42

Preparation of N-(6-Indolyl)-2-[1-(4-pyridyl)piperidin-4-yl-carbonylamino]-4-(acetylamino)benzamide

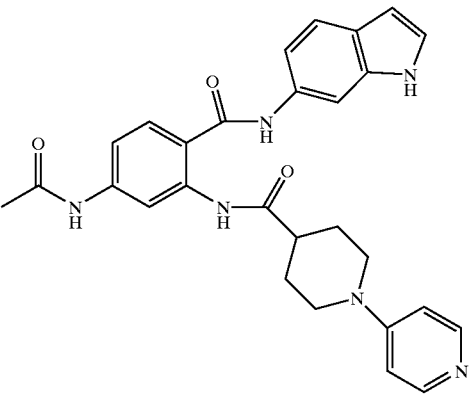

A) N-(1-tert-butoxycarbonyl-6-indolyl)-2-[1-(4-pyridyl)-piperidin-4-ylcarbonylamino]-4-nitrobenzamide

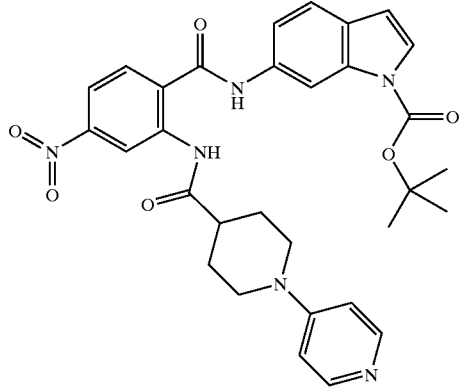

Using the procedure described in Example 38, Part A, N-(1-tert-butoxycarbonyl-6-indolyl)-2-amino-4-nitrobenzamide (1.09 mmol) was reacted to yield 408 mg (64%) of the title compound as a yellow solid.

IR(KBr): 1742, 1650, 1537, 1344; $^1$H-NMR (300 MHz, DMSO-$d_6$): δ10.76(s, 1H); 10.65(s, 1H); 8.93(s, 1H); 8.68(s, 1H); 8.14(d, J=6.6 Hz, 2H); 8.06–7.98(m, 2H); 7.61(d, J=3.9 Hz, 1H); 7.56(d, J=8.4 Hz, 1H); 7.47(d, J=9.0 Hz, 1H); 7.05(d, J=6.9 Hz, 2H); 6.65(d, J=3.6 Hz, 1H); 4.11(d, J=13.5 Hz, 2H); 3.20–3.10(m, 2H); 2.79(m, 1H); 1.98–1.90(m, 2H); 1.61(s, 1H); MS-FD m/e: 584.9 (p+1).

Analysis for $C_{31}H_{32}N_6O_6S$·3 $H_2O$: Calc: C, 58.30; H, 6.00; N, 13.16; Found: C, 58.12; H, 5.63; N, 12.94.

B) N-(1-tert-butoxycarbonyl-6-indolyl)-2-[1-(4-pyridyl)-piperidin-4 ylcarbonylamino]-4-aminobenzamide

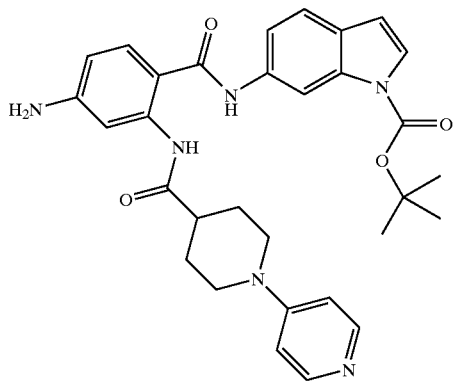

Using the procedure described in Example 2, Part B, N-(1-tert-butoxycarbonyl-6-indolyl)-2-[1-(4-pyridyl)-piperidin-4 ylcarbonylamino]-4-nitrobenzamide (0.65 mmol) was reacted to yield 236 mg (65%) of the title compound as a solid.

$^1$H-NMR(300 MHz, DMSO-$d_6$): δ11.72(s, 1H); 10.04(s, 1H); 8.58(s, 1H); 8.09(d, J=5.7 Hz, 2H); 7.76(s, 1H); 7.66(d, J=8.7 Hz, 1H); 7.58(d, J=3.6 Hz, 1H); 7.51(d, J=8.4 Hz, 1H); 7.43(d, J=8.4 Hz, 1H); 6.78(d, J=6.0 Hz, 2H); 6.63(d, J=3.6 Hz, 1H); 6.28(d, J=8.7 Hz, 1H); 5.91(s, 2H); 3.93(d, J=12.3 Hz, 2H); 2.88(m, 2H); 2.48(m, 1H); 1.90–1.85(m, 4H); 1.61(s, 1H); MS-FD m/e: 554.9 (p+1).

Analysis for $C_{31}H_{34}N_6O_4$: Calc: C, 67.13; H, 6.18; N, 15.15; *Found: C, 65.96; H, 5.74; N, 17.01.

C) N-(1-tert-butoxycarbonyl-6-indolyl)-2-[1-(4-pyridyl)-piperidin-4-ylcarbonylamino]-4-(acetylamino)benzamide

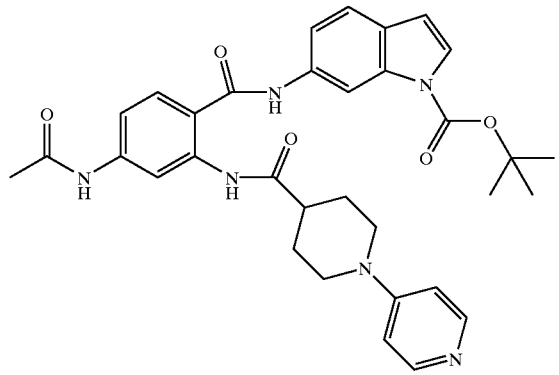

Using the procedure described in Example 24, Part E, N-(1-tert-butoxycarbonyl-6-indolyl)-2-[1-(4-pyridyl)-piperidin-4 ylcarbonylamino]-4-aminobenzamide (0.18 mmol) was reacted with acetyl chloride to yield 83 mg (77%) of the title compound as a white solid.

$^1$H-NMR (300 MHz, DMSO-$d_6$): δ11.09(s, 1H); 10.39(s, 1H); 10.23(s, 1H); 8.63(s, 1H); 8.53(d, J=4.5 Hz, 1H); 8.45(s, 1H); 8.08(d, J=5.4 Hz, 2H); 7.81(d, J=8.7 Hz, 1H); 7.60–7.32(m, 3H); 6.77(d, J=6.0 Hz, 2H); 6.64(d, J=3.3 Hz, 1H); 3.92(d, J=13.2 Hz, 2H); 2.88(m, 2H); 2.48(m, 1H); 1.95(s, 3H); 1.91–1.82(m, 2H); 1.60(s, 4H); FIA-MS m/e: 597.4 (p+1).

D) N-(6-indolyl)-2-[1-(4-pyridyl)piperidin-4-ylcarbonylamino]-4-(acetylamino)benzamide Using the procedure described in Example 41, Part F, N-(1-tert-butoxycarbonyl-6-indolyl)-2-[1-(4-pyridyl)-piperidin-4-ylcarbonylamino]-4-(acetylamino)benzamide was reacted to yield 60 mg (93%) of the title compound as a tan solid.

$^1$H-NMR (300 MHz, DMSO-$d_6$): δ11.22(s, 1H); 11.06(s, 1H); 10.21(s, 2H); 8.48(s, 1H); 8.09(d, J=5.4 Hz, 2H); 7.88(s, 1H); 7.81(d, J=8.7 Hz, 1H); 7.60(d, J=8.7 Hz, 1H); 7.45(d, J=8.4 Hz, 1H); 7.28(s, 1H); 7.17(d, J-8.4 Hz, 1H); 6.78(d, J=6.0 Hz, 2H); 6.35(s, 1H); 3.92(d, J=13.8 Hz, 2H); 2.88(t, J=11.4 Hz, 2H); 2.48(m, 1H); 2.03(s, 3H); 1.88(d, J=11.1 Hz, 2H); 1.58(d, J=14.7 Hz, 2H); FIA-MS m/e: 497.2 (p+1).

Analysis for $C_{28}H_{28}N_6O_3 \cdot 1.5\ H_2O$: Calc: C, 64.24; H, 5.97; N, 16.05; Found: C, 63.92; H, 5.40; N, 15.73.

EXAMPLE 43

Preparation of N-(6-Indolyl)-2-[1-(4-pyridyl)piperidin-4-yl-carbonylamino]-4-(methylsulfonylamino)benzamide

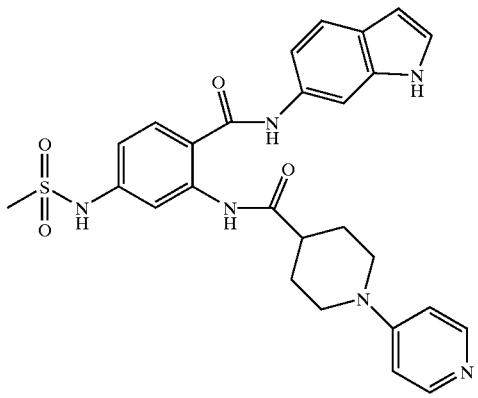

A) N-(1-tert-butoxycarbonyl-6-indolyl)-2-[1-(4-pyridyl)-piperidin-4 ylcarbonylamino]-4-(methylsulfonylamino) benzamide

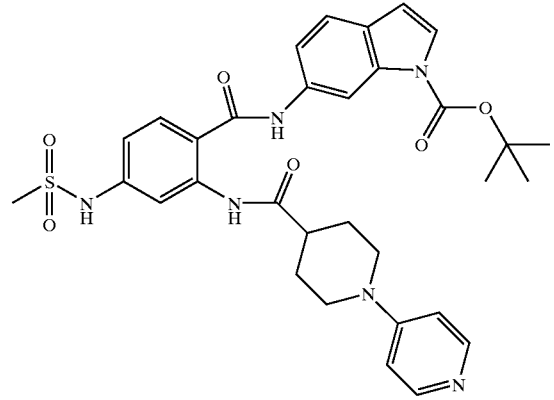

Using the procedure described in Example 24, Part E, N-(1-tert-butoxycarbonyl-6-indolyl)-2-[1-(4-pyridyl)-piperidin-4 ylcarbonylamino]-4-aminobenzamide (0.17 mmol) was reacted to yield 35 mg (65%) of the title compound as a yellow solid.

$^1$H-NMR (300 MHz, DMSO-$d_6$): δ11.33(s, 1H); 10.17(s, 1H); 8.62(s, 1H); 8.53(d, J=3.9 Hz, 1H); 8.08(d, J=5.4 Hz, 2H); 8.02(s, 1H); 7.70(d, J=8.7 Hz Hz, 1H); 7.58(d, J=3.9 Hz Hz, 1H); 7.52(d, J=8.4 Hz, 1H); 7.42(d, J=8.7 Hz, 1H); 7.34(m, 1H); 3.92(d, J=13.8 Hz, 2H); 2.81(m, 2H); 1.88(d, J=11.7 Hz, 4H); 1.61(s, 9H); FIA-MS m/e: 633.2 (p+1).

B) N-(6-Indolyl)-2-[1-(4-pyridyl)piperidin-4-yl-carbonylamino]-4-(methylsulfonylamino)benzamide Using the procedure described in Example 41, Part F, N-(1-tert-butoxycarbonyl-6-indolyl)-2-[1-(4-pyridyl)- piperidin-4-ylcarbonylamino]-4-(methylsulfonylamino) benzamide (0.096 mmol) was reacted to yield 35 mg (68%) of the title compound as a yellow solid.

MS-IS m/e: 533.0 (p+1)

Analysis for $C_{27}H_{28}N_6O_4S.1\ H_2O$: Calc: C, 58.91; H, 5.49; N, 15.26; *Found: C, 58.90; H, 5.35; N, 13.71.

EXAMPLE 44

Preparation of N-(6-Indolyl)-2-[1-(4-pyridyl) piperidin-4-yl-carbonylamino]benzamide

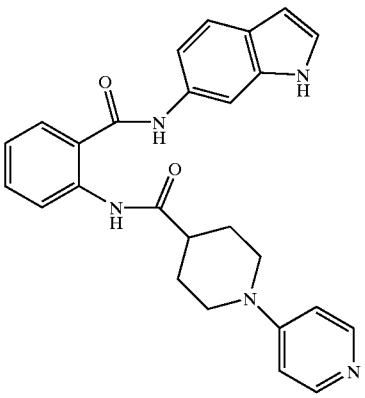

A) N-(6-indolyl)-2-aminobenzamide

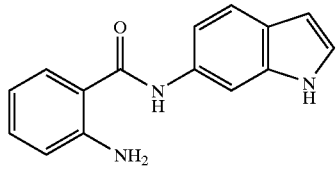

A mixture of isatoic anhydride (5.06 g, 31 mmol), 6-aminoindole (4.103 g, 31 mmol), toluene (300 mL) and DMF (30 mL) was heated to reflux for 18 hours. The reaction was cooled, filtered, and chromatographed to yield 4.103 g (53%) of the title compound as a tan solid.

IR(KBr): 1635, 1521, 1334; $^1$H-NMR (300 MHz, DMSO-$d_6$): 10.98(s, 1H); 9.87(s, 1H); 7.94(s, 1H); 7.59(d, J=7.8 Hz, 1H); 7.41(d, J=8.4 Hz, 1H); 7.24–7.12(m, 3H); 6.71(d, J=8.4 Hz, 1H); 6.55(t, J=7.4 Hz, 1H); 6.33(s, 1H); 6.25(s, 2H); MS-IS m/e: 252.2 (p+1).

Analysis for $C_{15}H_{13}N_3O$: Calc: C, 71.70; H, 5.22; N, 16.72; Found: C, 71.63; H, 5.18; N, 16.68.

B) N-(1-tert-butoxycarbonyl-6-indolyl)-2-aminobenzamide

Using the procedure described in Example 1, Part A, N-(6-indolyl)-2-aminobenzamide (2 mmol) was reacted to yield 281 mg (40%) of the title compound as a white solid.

C) N-(1-tert-butoxycarbonyl-6-indolyl)-2-[1-(4-pyridyl)-piperidin-4-ylcarbonylamino]benzamide

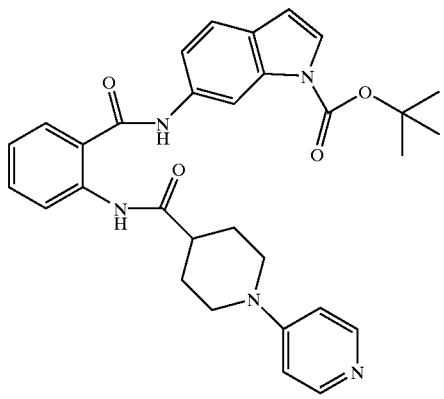

Using the procedure described in Example 38, Part A, N-(1-tert-butoxycarbonyl-6-indolyl)-2-aminobenzamide (0.74 mmol) was reacted to yield 343 mg (86%) of the title compound as a white solid.

IR(CHCl$_3$): 1729, 1597, 1511, 1431, 1347; $^1$H-NMR (300 MHz, DMSO-$d_6$): 10.65(s, 1H); 10.49(s, 1H); 8.68(s, 1H); 8.16(d, J=8.1 Hz, 2H); 8.07(s, 2H); 7.79(d, J=7.5 Hz, 1H); 7.60–7.44(m, 3H); 7.20(t, J=7.4 Hz, 1H); 6.78(s, 2H); 6.64 (s, 1H); 3.92(d, J=13.2 Hz, 2H); 2.89(t, J=11.6 Hz, 2H); 2.60(m, 1H); 1.87(d, J=13.5 Hz, 2H); 1.61(s, 1H); MS-IS m/e: 540.4 (p+1).

Analysis for $C_{31}H_{33}N_5O_4$: Calc: C, 69.00; H, 6.16; N, 12.98; Found: C, 69.15; H, 6.34; N, 12.72.

D) N-(6-indolyl)-2-[1-(4-pyridyl)piperidin-4-yl-carbonylamino]benzamide

Using the procedure described in Example 41, Part F, N-(1-tert-butoxycarbonyl-6-indolyl)-2-[1-(4-pyridyl)-piperidin-4-ylcarbonylamino]benzamide (0.56 mmol) was reacted to yield 232 mg (94%) of the title compound as a tan solid.

IR(CHCl$_3$): 1601, 1510, 1448; $^1$H-NMR (300 MHz, DMSO-$d_6$): 11.06(s, 1H); 10.79(s, 1H); 10.33(s, 1H); 8.23 (d, J=8.4 Hz, 1H); 8.08(d, J=4.8 Hz, 2H); 7.94(s, 1H); 7.80(d, J=7.8 Hz, 1H); 7.45(d, J=8.4, 2H); 7.28(s, 1H); 7.21–7.17(m, 2H); 6.77(d, J=5.7 Hz, 2H); 6.36(s, 1H); 3.91(d, J=13.2 Hz, 2H); 2.87(t, J=11.6 Hz, 2H); 2.60(m, 1H); 1.86(m, 2H); 1.55(m, 2H); MS-IS m/e: 440.2 (p+1).

Analysis for $C_{26}H_{25}N_5O_2$: Calc: C, 71.05; H, 5.73; N, 15.93; Found: C, 70.96; H, 5.89; N, 15.67.

EXAMPLE 45

Preparation of N-(6-Indolyl)-2-[1-(4-pyridyl) piperidin-4-yl-carbonylamino]-5-(methylsulfonylamino)benzamide

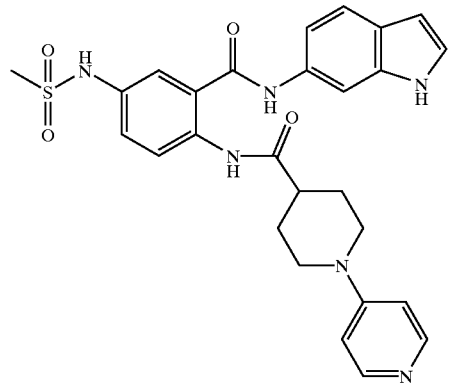

A) N-(6-indolyl)-2-amino-5-nitrobenzamide

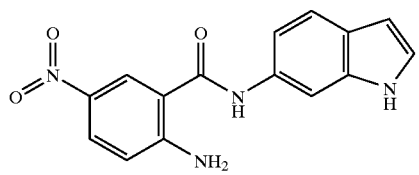

Using the procedure described in Example 4, Part A, 5-nitroisatoic anhydride (34 mmol) was reacted to yield 11.89 g (64%) of the title compound as a yellow solid.

$^1$H-NMR (300 MHz, DMSO-$d_6$): δ11.04(s, 1H); 10.33(s, 1H); 8.57(s, 1H); 8.04(d, J=9.0 Hz, 1H); 7.91(s, 1H); 7.60(s, 2H); 7.44(d, J=8.4 Hz, 1H); 7.27(s, 1H); 7.19(d, J=8.4 Hz, 1H); 6.82(d, J=9.0 Hz, 1H); 6.35(s, 1H); MS-FD m/e: 296.0 (p).

B) N-(1-tert-butoxy-6-indolyl)-2-amino-5-nitrobenzamide

Using the procedure described in Example 1, Part A, N-(6-indolyl)-2-amino-5-nitrobenzamide (6.77 mmol) was reacted to yield 1.287 g (48%) of the title compound as a yellow solid.

C) N-(1-tert-butoxycarbonyl-6-indolyl)-2-[1-(4-pyridyl)-piperidin-4-ylcarbonylamino]-5-nitrobenzamide

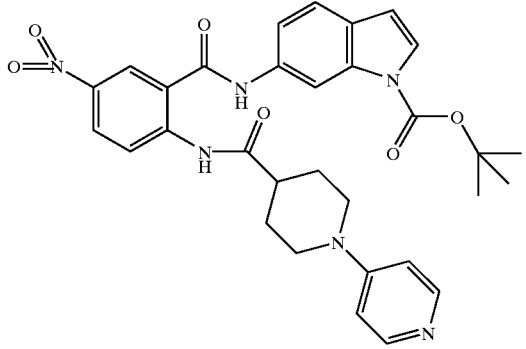

Using the procedure described in Example 38, Part A, N-(1-tert-butoxycarbonyl-6-indolyl)-2-amino-5-nitrobenzamide (2.42 mmol) was reacted to yield 1.125 g (80%) of the title compound as a yellow solid.

IR(CHCl$_3$): 1508, 1345, 1156; $^1$H-NMR (300 MHz, DMSO-$d_6$): δ11.09(s, 1H); 10.85(s, 1H); 8.66(s, 1H); 8.48–8.36(m, 2H); 8.12(d, J=5.4 Hz, 2H); 7.62(d, J=3.6 Hz, 1H); 7.59–7.47(m, 2H); 6.95(d, J=6.0 Hz, 2H); 6.66(d, J=3.6 Hz, 1H); 4.05(d, J=13.8 Hz, 2H); 3.05(t, J=11.6 Hz, 2H); 2.77(m, 1H); 1.94(d, J=10.8 Hz, 2H); 1.61(s, 9H); MS-FD m/e: 585.1 (p+1).

Analysis for C31H32N$_6$O$_6$.1 H$_2$O: Calc: C, 61.78; H, 5.69; N, 13.94; *Found: C, 62.15; H, 5.83; N, 13.04.

D) N-(1-tert-butoxycarbonyl-6-indolyl)-2-[(1-(4-pyridyl)-piperidin-4-ylcarbonyl)amino]-5-aminobenzamide

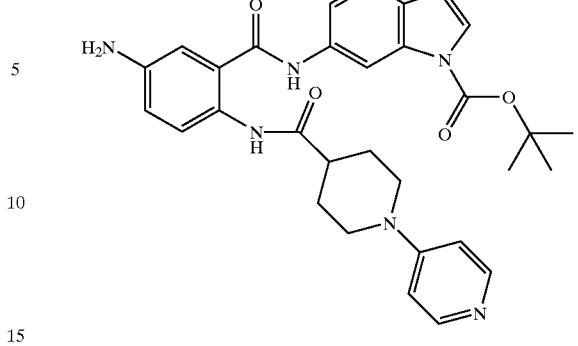

Using the procedure described in Example 2, Part B, N-(1-tert-butoxycarbonyl-6-indolyl)-2-[1-(4-pyridyl)-piperidin-4-ylcarbonyl)amino]-5-nitrobenzamide (1.86 mmol) was reacted to yield 1.11 g (100%) of the title compound as a yellow solid.

IR(CHCl$_3$): 1729, 1596, 1517, 1431, 1346; $^1$H-NMR (300 MHz, DMSO-$d_6$): δ10.28(s, 1H); 9.78(s, 1H); 8.69(s, 1H); 8.05(d, J=5.7 Hz, 2H); 7.59–7.42,(m, 4H); 6.85(s, 2H); 6.7(d, J=6.0 Hz, 1H); 6.66–6.62(m, 2H); 5.17(s, 2H); 3.89(d, J=13.5 Hz, 2H); 2.82(t, J=13.5 Hz, 2H); 2.46(m, 1H); 1.79(d, J=13.8 Hz, 2H); 1.60(s, 9H); 1.56(m, 2H); MS-FD m/e: 454.2 (p-BOC).

Analysis for C$_{31}$H$_{34}$N$_6$O$_4$.3.5 H$_2$O: Calc: C, 60.28; H, 6.69; N, 13.60; *Found: C, 59.96; H, 5.94; N, 12.71.

E) N-(1-tert-butoxycarbonyl-6-indolyl)-2-[1-(4-pyridyl)-piperidin-4-ylcarbonylamino]-5-methylsulfonylaminobenzamide

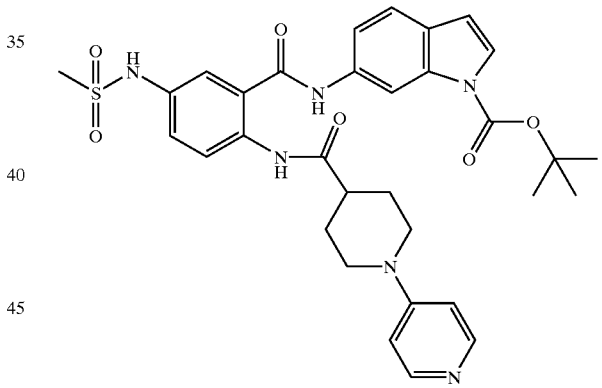

Using the procedure described in Example 24, Part E, N-(1-tert-butoxycarbonyl-6-indolyl)-2-[1-(4-pyridyl)-piperidin-4-ylcarbonylamino]-5-aminobenzamide (0.98 mmol) was reacted to yield 442 mg (71%) of the title compound as a white solid.

IR(KBr): 1733, 1646, 1546, 1345, 1151; $^1$H-NMR (300 MHz, DMSO-$d_6$): δ10.50(s, 1H); 10.16(s, 1H); 9.81(s, 1H); 8.63(s, 1H); 8.14(d, J=6.9 Hz, 2H); 7.84(d, J=8.7 Hz, 1H); 7.59–7.42(m, 4H); 7.31(d, J=8.4 Hz, 1H); 7.11(d, J=6.9 Hz, 2H); 6.64(s, 1H); 4.14(d, J=13.5 Hz, 2H); 3.22(m, 2H); 3.01(s, 3H); 2.74(m, 1H); 1.92(d, J=6.0 Hz, 2H); 1.60(s, 11H); MS-IS m/e: 633.2 (p+1).

Analysis for C$_{32}$H$_{36}$N$_6$O$_6$S.6.5 H$_2$O: Calc: C, 51.26; H, 6.59; N, 11.21; *Found: C, 51.19; H, 4.96; N, 11.10.

F) N-(6-indolyl)-2-[1-(4-pyridyl)piperidin-4-ylcarbonylamino]-5-(methylsulfonylamino)benzamide Using the procedure described in Example 41, Part F, N-(1-tert-butoxycarbonyl-6-indolyl)-2-[1-(4-pyridyl)- piperidin-4-ylcarbonylamino]-5-methylsulfonylaminobenzamide (0.63 nm mol) was reacted to yield 312 mg (93%) of the title compound as a tan solid.

IR(KBr): 1645, 1542, 1151, 981; $^1$H-NMR (300 MHz, DMSO-$d_6$): δ11.07(s, 1H); 10.34(s, 1H); 10.23(s, 1H); 9.80 (s, 1H); 8.14(d, J=7.2 Hz, 2H); 7.93(s, 1H); 7.91(d, J=10.8 Hz, 2H); 7.49(s, 1H); 7.43(d, J=8.4 Hz, 1H); 7.32–7.26(m, 3H); 7.16(d, J=9.0 Hz, 1H); 7.11(d, J=7.2 Hz, 2H); 6.35(s, 1H); 4.15(d, J=13.5 Hz, 2H); 3.20(m, 2H); 3.01(s, 3H); 2.97(m, 1H); 1.91(d, J=13.5 Hz, 2H); 1.60(m, 2H); MS-IS m/e: 533.2 (p+1).

Analysis for $C_{27}H_{28}N_6O_4S \cdot 6.5\ H_2O$: Calc: C, 49.91; H, 6.36; N, 12.93; *Found: C, 50.03; H, 4.84; N, 12.61.

EXAMPLE 46

Preparation of $N^2$-(1-Benzylpiperidin-4-ylcarbonyl)-4-hydroxy-$N^1$-(6-indolylcarbonyl)-1,2-benzenediamine

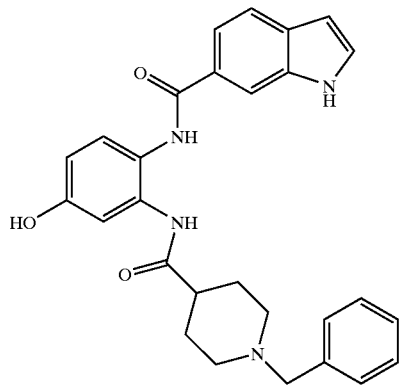

A) N-(1-benzylpiperidin-4-ylcarbonyl)-5-t-butyldimethylsilyloxy-2-(phthalimido)aniline A solution of N-benzylpiperidine-4-carboxylic acid (298 mg, 1.36 mmol) in 1 mL thionyl chloride was refluxed for 30 min. The mixture was concentrated in vacuo and the residue dissolved in 4 mL methylene chloride and 1 mL pyridine. The aniline (500 mg, 1.36 mmol) from Example 32, Part C was added all at once. The mixture was stirred 1 h then partitioned between methylene chloride and saturated sodium hydrogen carbonate. The organic portion was dried over magnesium sulfate, filtered and concentrated in vacuo. The residue was purified on silica gel, eluting 500 mL methylene chloride then 300 mL 9:1 methylene chloride/methanol. Appropriate fractions were combined and concentrated in vacuo and the residue crystallized from methylene chloride/hexane to yield 350 mg (46%) of the title compound.

FD-MS m/e: 569(p), 368.

B) $N^2$-(1-benzylpiperidin-4-ylcarbonyl)-4-hydroxy-$N^1$-(6-indolylcarbonyl)-1,2-benzenediamine The above aniline (310 mg, 0.54 mmol) was dissolved in 2 mL hot 1M hydrazine in methanol and warmed for 1 h during which time a white precipitate formed. The mixture was allowed to cool, then slurried with methylene chloride and filtered. The concentration of the filtrate in vacuo yielded 235 mg (99%) of the crude aniline as an orange solid.

The crude aniline (229 mg, 0.52 mmol), indole-6-carboxylic acid (168 mg, 1.04 mmol), bromo-tris-pyrrolidinophosphonium hexafluorophosphate (485 mg, 1.04 mmol) and diisopropylethylamine (362 AL, 2.08 mmol) were combined 3 mL methylene chloride, 2 mL tetrahydrofuran and 2 mL dimethylformamide. The resultant mixture was allowed to shake at 275 rpm on a platform shaker for 3 days then stand an additional 3 days. The mixture was filtered then purified on Aldrich $C_{18}$ silica eluting with a step gradient of 20–30–40% acetonitrile/water. Appropriate fractions were combined and concentrated in vacuo to yield 102 mg (34%) of the intermediate bisamide.

The bisamide (102 mg, 0.18 mmol) was dissolved in 3 mL 2:1 tetrahydrofuran/5N HCl and allowed to stand overnight. Volatile solvent was removed in vacuo end the residue neutralized with saturated sodium hydrogen carbonate causing a precipitate to form. The mixture was sonicated in the presence of ether/hexane for 5–10 min and filtered. The collected solid was dried under vacuum for 60 h to yield 59 mg (72%) of the title compound.

MS, FD+, m/e: 468(p).

What is claimed is:

1. A method of inhibiting factor Xa in a mammal comprising administering to the mammal in need thereof an effective amount of a factor Xa inhibiting compound of formula I

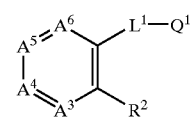

wherein $A^3, A^4, A^5$ and $A^6$, together with the two carbons to which they are attached, complete a substituted heteroaromatic ring in which two adjacent residues of $A^3, A^4, A^5$ and $A^6$ together form S, and each of the others is $CR^3$, $CR^4$, $CR^5$ or $CR^6$, respectively; wherein each of $R^3$, $R^4$, $R^5$ and $R^6$ is hydrogen, or one or two of $R^3$, $R^4$, $R^5$ and $R^6$ is independently chloro, bromo or methyl and the others are hydrogen;

$L^1$ is —NH—CO— or —CO—NH— such that —$L^1$—$Q^1$ is —NH—CO—$Q^1$ or —CO—NH—$Q^1$;

$Q^1$ is

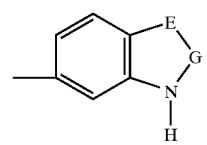

wherein

—E—G—NH— is —$CH_2$—$CH_2$—NH—, —C($R^a$)=CH—NH—, —C($R^a$)=N—NH—, —N=CH—NH— or —N=N—NH— in which $R^a$ is hydrogen, fluoro, chloro, bromo or methyl;

$R^2$ is —$L^{2A}$—$Q^{2A}$, —$L^{2B}$—$Q^{2B}$, —$L^{2C}$—$Q^{2C}$ or —$L^{2D}$—$Q^{2D}$ wherein $L^{2A}$ is a direct bond; and $Q^{2A}$ is in which
- D is carbonyl or —CHR$^k$— in which R$^k$ is hydrogen, hydroxy, (1–6C)alkoxy or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;
- L$^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$—O—Q$^{2B}$ or —O—CH$_2$—Q$^{2B}$; and
- Q$^{2B}$ is in which
- R$^o$ is hydrogen, halo, (1–6C)alkyl, (1–4C)alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxo, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl;
- L$^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —L$^{2C}$—Q$^{2C}$ is —NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—, —NR$^w$—CH$_2$—, —O—, —O—CH$_2$— or —S—CH$_2$—; Y is —NR$^w$—CH$_2$— or —O—CH$_2$—; each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and
- Q$^{2C}$ is 1-(4-pyridyl)piperidin-4-yl, 1-(4-pyridyl)piperidin-3-yl or 1-(4-pyridyl)pyrrolidin-3-yl in which the pyridyl may bear a substituent at its 2-position selected from cyano, aminomethyl, carboxy, hydroxymethyl and (1–2C)alkyl;
- L$^{2D}$ is —NH—CO— such that —L$^{2D}$—Q$^{2D}$ is —NH—CO—Q$^{2D}$; and
- Q$^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl or 3,4-didehydropiperidin-4-yl (either one bearing a substituent at the 1-position selected from methylsulfonyl, phenylsulfonyl, (1–5C)alkyl, (4–7C)cycloalkyl, tetrahydropyran-4-yl, 4-thiacyclohexyl and —CH$_2$—R$^z$ in which R$^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent);

or a prodrug of the compound of formula I;

or a pharmaceutically acceptable salt of the compound of formula I or prodrug thereof.

2. The method of claim 1 in which the factor Xa inhibiting compound is one wherein A$^3$, A$^4$, A$^5$ and A$^6$, together with the two carbons to which they are attached, complete a substituted heteroaromatic ring in which two adjacent residues of A$^3$, A$^4$, A$^5$ and A$^6$ together form S, and each of the others is CR$^3$, CR$^4$, CR$^5$ or CR$^6$, respectively; wherein each of R$^3$, R$^4$, R$^5$ and R$^6$ is hydrogen, or one or two of R$^3$, R$^4$, R$^5$ and R$^6$ is independently chloro, bromo or methyl and the others are hydrogen;

L$^1$ is —NH—CO— or —CO—NH— such that —L$^1$—Q$^1$ is —NH—CO—Q$^1$ or —CO—NH—Q$^1$;

Q$^1$ is wherein

—E—G—NH— is —CH$_2$—CH$_2$—NH—, —C(R$^a$)=CH—NH—, —C(R$^a$)=N—NH—, —N=CH—NH— or —N=N—NH— in which R$^a$ is hydrogen, fluoro, chloro, bromo or methyl;

R$^2$ is —L$^{2A}$—Q$^{2A}$, —L$^{2B}$—Q$^{2B}$, —L$^{2C}$—Q$^{2C}$ or —L$^{2D}$—Q$^{2D}$ wherein L$^{2A}$ is a direct bond; and Q$^{2A}$ is in which
- D is carbonyl or —CHR$^k$— in which R$^k$ is hydrogen, hydroxy, (1–6C)alkoxy or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;
- L$^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$—O—Q$^{2B}$ or —O—CH$_2$—Q$^{2B}$; and $Q^{2B}$ is

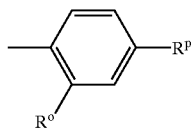

in which
  $R^o$ is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —S(O)$_q$— (wherein q is 0, 1 or 2), or —NR$^r$— (wherein $R^r$ is hydrogen or methyl); and $R^q$ is (1–6C)alkyl, phenyl, 3-pyridyl or 4-pyridyl;
  $L^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —$L^{2C}$—$Q^{2C}$ is —NR$^v$—CO—X—$Q^{2C}$, —NR$^v$—CS—Y—$Q^{2C}$, —CH$_2$—CO—NR$^w$—CH$_2$—$Q^{2C}$, —O—CO—$Q^{2C}$, —O—CH$_2$—$Q^{2C}$, —S—CH$_2$—$Q^{2C}$ or —CH$_2$—NR$^x$—CH$_2$—$Q^{2C}$ in which X is —(CH$_2$)$_x$— (wherein x is 0, 1 or 2), —NR$^w$—CH$_2$—, —O—CH$_2$— or —S—CH$_2$—; Y is —NR$^w$—CH$_2$— or —O—CH$_2$—; each of $R^v$ and $R^w$ is independently hydrogen, benzyl or (1–6C)alkyl which is not branched at the α-position; and $R^x$ is hydrogen, benzyloxycarbonyl or [(1–4C)alkoxy]carbonyl; and
  $Q^{2C}$ is 1-(4-pyridyl)piperidin-4-yl in which the pyridyl may bear a substituent at its 2-position selected from cyano, aminomethyl, carboxy, hydroxymethyl and (1–2C)alkyl;
  $L^{2D}$ is —NH—CO— such that —$L^{2D}$—$Q^{2D}$ is —NH—CO—$Q^{2D}$; and
  $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —CH$_2$—$R^z$ in which $R^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent;
or a prodrug of the compound of formula I;
or a pharmaceutically acceptable salt of the compound of formula I or prodrug thereof.

3. The method of claim 1 or 2 wherein for an alkyl group or the alkyl portion of an alkyl containing group, (1–2C)alkyl is methyl or ethyl; (1–4C)alkyl is methyl, ethyl, propyl, isopropyl, butyl, isobutyl, or t-butyl; (1–6C)alkyl is methyl, ethyl, propyl, butyl, pentyl or hexyl; and halo is bromo or chloro.

4. The method of claim 3 wherein for an alkyl group or the alkyl portion of an alkyl containing group, (1–2C)alkyl is methyl; (1–4C)alkyl is methyl, isopropyl, butyl or t-butyl; (1–6C)alkyl is methyl, butyl or hexyl; and halo is chloro.

5. The method of claim 3 wherein the compound of formula I is one in which two adjacent residues of $A^3$, $A^4$, $A^5$ and $A^6$ together form S, and each of the others is CH.

6. The method of claim 3 wherein $Q^1$ is 6-indolyl or 6-indazolyl.

7. The method of claim 3 wherein $R^2$ is (4-t-butylbenzoyl)amino, (4-methoxybenzoyl)amino, or [1-(4-pyridyl)piperidin-4-yl]methoxycarbonylamino.

8. The method of claim 3 wherein $L^1$—$Q^1$ is —NH—CO—$Q^1$.

9. The method of claim 3 wherein $L^1$—$Q^1$ is —CO—NH—$Q^1$.

10. A compound of formula I

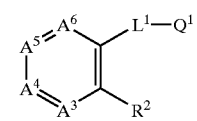

wherein
  $A^3$, $A^4$, $A^5$ and $A^6$, together with the two carbons to which they are attached, complete a substituted heteroaromatic ring in which two adjacent residues of $A^3$, $A^4$, $A^5$ and $A^6$ together form S, and each of the others is C$R^3$, C$R^4$, C$R^5$ or C$R^6$, respectively; wherein
  each of $R^3$, $R^4$, $R^5$ and $R^6$ is hydrogen, or one or two of $R^3$, $R^4$, $R^5$ and $R^6$ is independently chloro, bromo or methyl and the others are hydrogen;
  $L^1$ is —NH—CO— or —CO—NH— such that —$L^1$—$Q^1$ is —NH—CO—$Q^1$ or —CO—NH—$Q^1$;
  $Q^1$ is

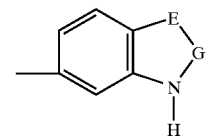

wherein
  —E—G—NH— is —CH$_2$—CH$_2$—NH—, —C($R^a$)=CH—NH—, —C($R^a$)=N—NH—, —N=CH—NH— or —N=N—NH— in which $R^a$ is hydrogen, fluoro, chloro, bromo or methyl;
  $R^2$ is —$L^{2A}$—$Q^{2A}$, —$L^{2B}$—$Q^{2B}$, —$L^{2C}$—$Q^{2C}$ or —$L^{2D}$—$Q^{2D}$ wherein
  $L^{2A}$ is a direct bond; and
  $Q^{2A}$ is

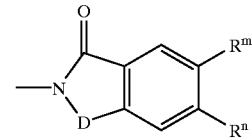

in which
  D is carbonyl or —CHR$^k$— in which $R^k$ is hydrogen, hydroxy, (1–6C)alkoxy or —CH$_2$—$R^j$ in which $R^j$ is carboxy, [(1–4C)alkoxy]carbonyl or carbamoyl which may bear one or two (1–2C)alkyl substituents on the nitrogen; and one of $R^m$ and $R^n$ is hydrogen and the other is amino, bromo, (1–4C)alkyl or (1–4C)alkoxy, or $R^m$ and $R^n$ together form a benz ring;
  $L^{2B}$ is —NH—CO—, —O—CO—, —CH$_2$—O— or —O—CH$_2$— such that —$L^{2B}$—$Q^{2B}$ is —NH—CO—$Q^{2B}$, —O—CO—$Q^{2B}$, —CH$_2$—O—$Q^{2B}$ or —O—CH$_2$—$Q^{2B}$; and

71

$Q^{2B}$ is

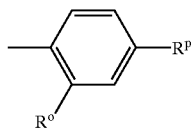

in which
R° is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —S(O)$_q$— (wherein q is 0, 1 or 2), or —NR$^r$— (wherein $R^r$ is hydrogen or methyl); and $R^q$ is (1–6C)alkyl, phenyl, 3-pyridyl or 4-pyridyl;

$L^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —$L^{2C}$—$Q^{2C}$ is —NR$^v$—CO—X—$Q^{2C}$, —NR$^v$—CS—Y—$Q^{2C}$, —CH$_2$—CO—NR$^w$—CH$_2$—$Q^{2C}$, —O—CO—$Q^{2C}$, —O—CH$_2$—$Q^{2C}$, —S—CH$_2$—$Q^{2C}$ or —CH$_2$—NR$^x$—CH$_2$—$Q^{2C}$ in which X is —(CH$_2$)$_x$— (wherein x is 0, 1 or 2), —NR$^w$—, —NR$^w$—CH$_2$—, —O—, —O—CH$_2$— or —S—CH$_2$—; Y is —NR$^w$—CH$_2$— or —O—CH$_2$—; each of $R^v$ and $R^w$ is independently hydrogen, benzyl or (1–6C)alkyl which is not branched at the α-position; and $R^x$ is hydrogen, benzyloxycarbonyl or [(1–4C)alkoxy]carbonyl; and $Q^{2C}$ is 1-(4-pyridyl)piperidin-4-yl, 1-(4-pyridyl)-piperidin-3-yl or 1-(4-pyridyl)pyrrolidin-3-yl in which the pyridyl may bear a substituent at its 2-position selected from cyano, aminomethyl, carboxy, hydroxymethyl and (1–2C)alkyl;

$L^{2D}$ is —NH—CO— such that —$L^{2D}$—$Q^{2D}$ is —NH—CO—$Q^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl or 3,4-didehydropiperidin-4-yl (either one bearing a substituent at the 1-position selected from methylsulfonyl, phenylsulfonyl, (1–5C)alkyl, (4–7C)cycloalkyl, tetrahydropyran-4-yl, 4-thiacyclohexyl and —CH$_2$—$R^z$ in which $R^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent);

or a prodrug of the compound of formula I;
or a pharmaceutically acceptable salt of the compound of formula I or prodrug thereof.

11. The compound of claim 10 wherein
$A^3$, $A^4$, $A^5$ and $A^6$, together with the two carbons to which they are attached, complete a substituted heteroaromatic ring in which two adjacent residues of $A^3$, $A^4$, $A^5$ and $A^6$ together form S, and each of the others is $CR^3$, $CR^4$, $CR^5$ or $CR^6$, respectively; wherein
each of $R^3$, $R^4$, $R^5$ and $R^6$ is hydrogen, or one or two of $R^3$, $R^4$, $R^5$ and $R^6$ is independently chloro, bromo or methyl and the others are hydrogen;

72

$L^1$ is —NH—CO— or —CO—NH— such that —$L^1$—$Q^1$ is —NH—CO—$Q^1$ or —CO—NH—$Q^1$;
$Q^1$ is

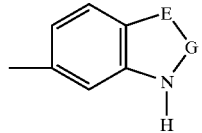

wherein
—E—G—NH— is —CH$_2$—CH$_2$—NH—, —C($R^a$)=CH—NH—, —C($R^a$)=N—NH—, —N=CH—NH— or —N=N—NH— in which $R^a$ is hydrogen, fluoro, chloro, bromo or methyl;

$R^2$ is —$L^{2A}$—$Q^{2A}$, —$L^{2B}$—$Q^{2B}$, —$L^{2C}$—$Q^{2C}$ or —$L^{2D}$—$Q^{2D}$ wherein
$L^{2A}$ is a direct bond; and
$Q^{2A}$ is

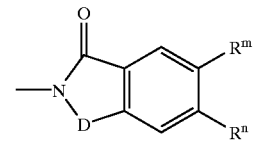

in which
D is carbonyl or —CHR$^k$— in which $R^k$ is hydrogen, hydroxy, (1–6C)alkoxy or —CH$_2$—$R^j$ in which $R^j$ is carboxy, [(1–4C)alkoxy]carbonyl or carbamoyl which may bear one or two (1–2C)alkyl substituents on the nitrogen; and one of $R^m$ and $R^n$ is hydrogen and the other is amino, bromo, (1–4C)alkyl or (1–4C)alkoxy, or $R^m$ and $R^n$ together form a benz ring;

$L^{2B}$ is —NH—CO—, —O—CO—, —CH$_2$—O— or —O—CH$_2$— such that —$L^{2B}$—$Q^{2B}$ is —NH—CO—$Q^{2B}$, —O—CO—$Q^{2B}$, —CH$_2$—O—$Q^{2B}$ or —O—CH$_2$—$Q^{2B}$; and
$Q^{2B}$ is

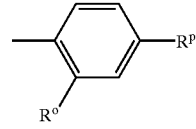

in which
R° is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —S(O)$_q$— (wherein q is 0, 1 or 2), or —NR$^r$— (wherein $R^r$ is hydrogen or methyl); and $R^q$ is (1–6C)alkyl, phenyl, 3-pyridyl or 4-pyridyl;

$L^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —$L^{2C}$—$Q^{2C}$ is —NR$^v$—CO—X—$Q^{2C}$, —NR$^v$—CS—Y—$Q^{2C}$, —CH$_2$—CO—NR$^w$—CH$_2$—$Q^{2C}$, —O—CO—$Q^{2C}$, —O—CH$_2$—$Q^{2C}$, —S—CH$_2$—$Q^{2C}$ or —CH$_2$—NR$^x$—CH$_2$—$Q^{2C}$ in which X is —(CH$_2$)$_x$— (wherein x is 0, 1 or 2), —NR$^w$—CH$_2$—, —O—CH$_2$— or —S—CH$_2$—; Y is —NR$^w$—CH$_2$— or —O—CH$_2$—; each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and Q$^{2C}$ is 1-(4-pyridyl)piperidin-4-yl in which the pyridyl may bear a substituent at its 2-position selected from cyano, aminomethyl, carboxy, hydroxymethyl and (1–2C)alkyl;

L$^{2D}$ is —NH—CO— such that —L$^{2D}$—Q$^{2D}$ is —NH—CO—Q$^{2D}$; and

Q$^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —CH$_2$—R$^z$ in which R$^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent;

or a prodrug of the compound of formula I;

or a pharmaceutically acceptable salt of the compound of formula I or prodrug thereof.

12. The compound of claim 10 or 11 wherein for an alkyl group or the alkyl portion of an alkyl containing group, (1–2C)alkyl is methyl or ethyl; (1–4C)alkyl is methyl, ethyl, propyl, isopropyl, butyl, isobutyl, or t-butyl; (1–6C)alkyl is methyl, ethyl, propyl, butyl, pentyl or hexyl; and halo is bromo or chloro.

13. The compound of claim 12 wherein for an alkyl group or the alkyl portion of an alkyl containing group, (1–2C)alkyl is methyl; (1–4C)alkyl is methyl, isopropyl, butyl or t-butyl; (1–6C)alkyl is methyl, butyl or hexyl; and halo is chloro.

14. The compound of claim 12 wherein the compound of formula I is one in which two adjacent residues of A$^3$, A$^4$, A$^5$ and A$^6$ together form S, and each of the others is CH.

15. The compound of claim 12 wherein Q$^1$ is 6-indolyl or 6-indazolyl.

16. The compound of claim 12 wherein R$^2$ is (4-t-butylbenzoyl)amino, (4-methoxybenzoyl)amino, or [1-(4-pyridyl)piperidin-4-yl]methoxycarbonylamino.

17. The compound of claim 12 wherein —L$^1$—Q$^1$ is —NH—CO—Q$^1$.

18. The compound of claim 12 wherein —L$^1$—Q$^1$ is —CO—NH—Q$^1$.

19. A pharmaceutical composition comprising a compound of formula I, or prodrug or pharmaceutically acceptable salt thereof, as claimed in claim 10 in association with a pharmaceutically acceptable carrier, excipient or diluent.

20. A process for preparing a compound of formula I (or a pharmaceutically acceptable salt thereof) as provided in claim 10 comprising the step selected from (A) for a compound of formula I in which the linkage of R$^2$ to the ring terminates in —NH—CO—, —NR$^v$—CO— or —NR$^v$—CS—, acylating an amine of formula II,

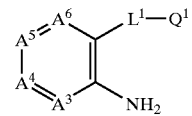

or a corresponding amine in which the nitrogen bears the group R$^v$, using a corresponding acid which terminates with the group HO—CO— or HO—CS—, or an activated derivative thereof;

(B) for a compound of formula I in which —L$^1$—Q$^1$ is —NH—CO—Q$^1$, acylating an amine of formula III

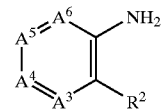

using an acid of formula HO—CO—Q$^1$, or an activated derivative thereof;

(C) for a compound of formula I in which —L$^1$—Q$^1$ is —CO—NH—Q$^1$ and R$^2$ is of the form —NH—CO—Q$^2$, acylating an amine of formula H$_2$N—Q$^1$ using a [1,3]oxazine of formula IV,

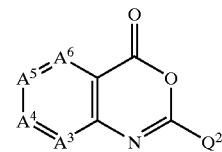

wherein Q$^2$ represents Q$^{2B}$, Q$^{2C}$ or Q$^{2D}$;

(D) for a compound of formula I in which R$^2$ is —L$^{2A}$—Q$^{2A}$ and D is carbonyl, diacylating a compound of formula II using an anhydride of formula V;

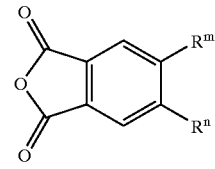

(E) for a compound of formula I in which R$^2$ is —O—CO—Q$^{2B}$, acylating an alcohol of formula VI

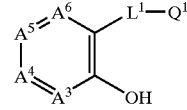

using an acid of formula HO—CO—Q$^{2B}$, or an activated derivative thereof; and (F) for a compound of formula I is which —E—G—NH— is —CH$_2$—CH$_2$—NH—, reducing the double bond of a corresponding compound of formula I in which —E—G—NH— is —CH=CH—NH—; and whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure; and wherein, unless otherwise specified above in this claim, $L^1$, $Q^1$, $R^2$, $R^m$, $R^n$, $A^3$, $A^4$, $A^5$ and $A^6$ have any of the values defined in claim 10.

21. The compound of claim 12 wherein two adjacent residues of $A^3$, $A^4$, $A^5$ and $A^6$ together form S, and each of the others is CH; $Q^1$ is 6-indolyl or 6-indazolyl; $R^2$ is (4-t-butylbenzoyl)amino, (4-methoxybenzoyl)amino, or [1-(4-pyridyl)piperidin-4-yl]methoxycarbonylamino; and —$L^1$—$Q^1$ is —NH—CO—$Q^1$.

22. The compound of claim 12 wherein two adjacent residues of $A^3$, $A^4$, $A^5$ and $A^6$ together form S, and each of the others is CH; $Q^1$ is 6-indolyl or 6-indazolyl; $R^2$ is (4-t-butylbenzoyl)amino, (4-methoxybenzoyl)amino, or [1-(4-pyridyl)piperidin-4-yl]methoxycarbonylamino; and —$L^1$—$Q^1$ is —CO—NH—$Q^1$.

23. The compound of claim 10 which is 3-[(4-t-butylbenzoyl)amino]-N-(6-indazolyl)-2-thiophene-caboxamide.

* * * * *